(12) United States Patent
Low

(10) Patent No.: US 11,690,557 B2
(45) Date of Patent: Jul. 4, 2023

(54) AUTOMATED DETECTION OF SLEEP AND WAKING STATES

(71) Applicant: The Salk Institute For Biological Studies Intellectual Property And Technology Transfer, San Diego, CA (US)

(72) Inventor: Philip Low, Moffett Field, CA (US)

(73) Assignee: The Salk Institute For Biological Studies Intellectual Property And Technology Transfer, San Diego, CA (US)

(*) Notice: Subject to any disclaimer, the term of this patent is extended or adjusted under 35 U.S.C. 154(b) by 224 days.

(21) Appl. No.: 16/527,705

(22) Filed: Jul. 31, 2019

(65) Prior Publication Data

US 2020/0167560 A1 May 28, 2020

Related U.S. Application Data

(63) Continuation of application No. 13/270,099, filed on Oct. 10, 2011, now abandoned, which is a
(Continued)

(51) Int. Cl.
*A61B 5/374* (2021.01)
*A61B 5/00* (2006.01)

(52) U.S. Cl.
CPC ............ *A61B 5/374* (2021.01); *A61B 5/4812* (2013.01); *A61B 5/4815* (2013.01);
(Continued)

(58) Field of Classification Search
None
See application file for complete search history.

(56) References Cited

U.S. PATENT DOCUMENTS

| 4,026,630 A | | 5/1977 | Wollenmann | |
|---|---|---|---|---|
| 5,083,571 A | * | 1/1992 | Prichep | A61B 5/377 600/544 |

(Continued)

FOREIGN PATENT DOCUMENTS

WO  02/32305 A1  4/2002

OTHER PUBLICATIONS

Salinsky et al., Representation of sleep stages by color density spectral array, 1987: Electroencephalography and clinical Neurophysiology, 66: 579-582. (Year: 1987).*

(Continued)

*Primary Examiner* — Michael R Bloch
(74) *Attorney, Agent, or Firm* — Kilpatrick Townsend & Stockton LLP

(57) ABSTRACT

Determining low power frequency range information from spectral data. Raw signal data can be adjusted to increase dynamic range for power within low power frequency ranges as compared to higher-power frequency ranges to determine adjusted source data valuable for acquiring low power frequency range information. Low power frequency range information can be used in the analysis of a variety of raw signal data. For example, low power frequency range information within electroencephalography data for a subject from a period of sleep can be used to determine sleep states. Similarly, automated full-frequency spectral electroencephalography signal analysis can be useful for customized analysis including assessing sleep quality, detecting pathological conditions, and determining the effect of medication on sleep states.

15 Claims, 35 Drawing Sheets

Related U.S. Application Data continuation of application No. 11/431,425, filed on May 9, 2006, now Pat. No. 8,073,534.

(60) Provisional application No. 60/679,951, filed on May 10, 2005.

(52) U.S. Cl.
CPC .......... *A61B 5/7264* (2013.01); *A61B 5/7203* (2013.01); *A61B 5/726* (2013.01); *A61B 5/7267* (2013.01); *G06F 2218/12* (2023.01)

(56) References Cited

U.S. PATENT DOCUMENTS

| | | | | |
|---|---|---|---|---|
| 5,154,180 | A * | 10/1992 | Blanchet | A61B 5/374 600/544 |
| 5,813,993 | A | 9/1998 | Kaplan et al. | |
| 5,819,007 | A | 10/1998 | Elghazzawi | |
| 5,846,208 | A | 12/1998 | Pichlmayr et al. | |
| 6,070,098 | A | 5/2000 | Moore-Ede et al. | |
| 6,549,804 | B1 | 4/2003 | Osorio et al. | |
| 6,731,975 | B1 * | 5/2004 | Viertio-Oja | A61B 5/389 600/544 |
| 2002/0082513 | A1 * | 6/2002 | Ennen | A61B 5/369 600/544 |
| 2004/0010203 | A1 * | 1/2004 | Bibian | A61B 5/726 600/544 |
| 2004/0092809 | A1 | 5/2004 | DeCharms | |
| 2004/0181162 | A1 | 9/2004 | Wilson | |
| 2004/0254493 | A1 | 12/2004 | Chervin et al. | |
| 2005/0043652 | A1 | 2/2005 | Lovett et al. | |
| 2005/0080828 | A1 * | 4/2005 | Johnson | A61B 5/374 708/160 |
| 2006/0217628 | A1 * | 9/2006 | Huiku | A61B 5/4839 600/544 |

OTHER PUBLICATIONS

Altman et al. Psychon. Sci. 26 (1972), pp. 152-154.
Amzica & Steriade. Neuroscience. Feb. 1998;82(3):671-86.
Ayala-Guerrero et al. Physiol Behav. 1988;43(5):585-9.
Buzsaki. Neuroscience. 1989;31 (3):551-70.
Cantero et al. Neuroimage. Jul. 2004;22(3):1271-80.
Dave & Margoliash. Science. Oct. 27, 2000;290(5492):812-6.
Destexhe etal.: Jun. 1, 1999;19(11):4595-608.
Fen et al. Nature. Oct. 9, 2003;425(6958):614-6.
Gervasoni et al. J Neurosci. Dec. 8, 2004;24(49):11137-47.
Glin et al. Physiol Behav. Nov. 1991;50(5):951-3.
Gottesmann et al. J Physiol (Paris). 1984;79(5):365-72.
Hahnloser et al. Nature. Sep. 5, 2002;419(6902):65-70.
International Search Report dated Sep. 24, 2007 regarding PCT/US2006/018120.
Kami et al. Science. Jul. 29, 1994; 265(5172):679-682.
Karten. Proc Natl Acad Sci U S A. Apr. 1, 1997;94(7):2800-4.
Khazipov et al. Society for Neuroscience Abstracts 2004.
Kirov & Moyanova. Neurosci Lett. Apr. 5, 2002;322(2):134-6.
Louie & Wilson. Neuron. Jan. 2001;29(1):145-56.
Lyamin et al. Behav Brain Res. Feb. 1, 2002;129(1-2):125-9.
Maloney et al. Neuroscience. Jan. 1997;76(2):541-55.
Mednick et al. Nat Neurosci. Jul. 2002;5(7):677-81.
Mednick et al. Nat Neurosci. Jul. 2003;6(7):697-8.
Mintz et al. Neurosci Lett. Dec. 18, 1998;258(2):61-4.
Mukhametov et al. Zh Vyssh New Deiat Im I P Pavlova. Mar.-Apr. 1984;34(2):259-64.
Mukhametov. Neurosci Lett. Aug. 18, 1987;79(1-2):128-32
Nick & Konishi. Proc Natl Acad Sci U S A. Nov. 20, 2001;98(24):14012-6.
Rattenborg et al. Behav Brain Res. Nov. 15, 1999;105(2):163-72.
Rattenborg et al. PLoS Biol. Jul. 2004;2(7):0924-36.
Rowan & Tolusnky. "Primer of EEG". Butterworth Heinemann. Elsevier Science 2003.
Salinsky et al., Representation of sleep stages by color density spectral array, 1987. Electroencephalography and clinical Neurophysiology, 66: 579-582.
Siegel et al. Neuroscience. 1999;91(1):391-400.
Szymczak et al. Physiol Behav. Jun. 1993;53(6):1201-10.
Szymczak et al. Physiol Behav. Oct. 1996,60(4):1115-20.
Tchernichovski et al. Science. Mar. 30, 2001;291(5513):2564-9.
Thomson, Proceedings of the IEEE, vol. 70 (1982), pp. 1055-1096.
Wilson & McNaughton. Science. Aug. 20, 1993;261(5124):1055-8.

* cited by examiner

AUTOMATED DETECTION OF SLEEP AND WAKING STATES

CROSS-REFERENCE TO RELATED APPLICATIONS

This application is a continuation of proper U.S. patent application Ser. No. 13/270,099, filed Oct. 10, 2011; which is a continuation of prior U.S. patent application Ser. No. 11/431,425, filed May 9, 2006, now issued as U.S. Pat. No. 8,073,534; which claims the benefit of U.S. Provisional Application Ser. No. 60/679,951, filed May 10, 2005. The disclosure of the prior applications is considered part of (and is incorporated by reference in) the disclosure of this application.

BACKGROUND OF THE INVENTION

Sleep states and other brain activity have been commonly analyzed via electroencephalography or EEG signals. As a person falls asleep, the brain activity is modulated, representing different depths and phases of sleep. In a typical person, the sleep states transition over time, starting at a first sleep state known as slow wave sleep or SWS. SWS has low frequency high power EEG activity. The sleep may lighten into so-called intermediate sleep states. Other sleep states known as rapid eye movement sleep are characterized by a lower power EEG activity.

EEG signals follow a distribution where higher frequency signals have lower amplitudes and therefore lower power. This so-called 1/f distribution means that the highest amplitudes are present at the lowest frequencies.

EEG signals for sleep stage determination are conventionally analyzed using the Rechtschaffen-Kales method. This method can rely on manually scoring sleep EEG signals due to the low power frequency limitations of automated signal analysis techniques. The Rechtschaffen-Kales method can be both highly unreliable and time consuming because statistically significant shifts at high frequencies are usually not detectable by a human scorer due to the very low amplitudes. Further, the Rechtschaffen-Kales method tends to have poor temporal and spatial resolution, does not make all of its variables known, and commonly leads to low inter-user agreement rates across both manual as well as automated scorers. Unfortunately, alternative sleep state determination methods, including artificial neural network classifiers, usually rely on multiple channels and tend to emulate human performance, thereby improving the time of determination without drastically improving quality.

SUMMARY OF THE INVENTION

The present application describes normalizing data indicative of brainwave activity to increase the dynamic range of information within the data.

The embodiments explain using this information to determine sleep states automatically. Other applications are described which automatically assess sleep quality, pathological conditions, and medication effects.

DETAILED DESCRIPTION OF THE INVENTION

One important recognition of the present system is that the low frequency ranges in EEG signals often have the most energy, and hence have mistakenly led many researchers to overanalyze that low frequency range. However, one reason found for the increased power in those lower frequencies, was found by the inventors to be the low-pass characteristic of the skull. Other reasons may also contribute to the increased power in lower frequencies.

Obtained EEG signals are low-power frequency signals and follow a 1/f distribution, whereby the power in the signal is inversely related, e.g., inversely proportional, to the frequency.

EEG signals have typically been examined in time in series increments called epochs. For example, when the EEG signal is used for analyzing sleep, sleep may be segmented into one or more epochs to use for analysis. The epochs can be segmented into different sections using a scanning window, where the scanning window defines different sections of the time series increment. The scanning window can move via a sliding window, where sections of the sliding window have overlapping time series sequences. An epoch can alternatively span an entire time series, for example.

According to the present application, different forms of sleep state may be monitored. A sleep state is described as any distinguishable sleep or wakefulness that is representative of behavioral, physical or signal characteristics. Sleep states which are referred to in this application include slow wave sleep or SWS, rapid eye movement sleep or REM, intermediate sleep states also called inter or IS states, and awake states. Awake states may actually be part of the sleep state, and the awake states can be characterized by vigilance into attentiveness or levels of alertness. The intermediate sleep can also be characterized as intermediate-1 sleep and intermediate-2 sleep.

An artifact may also be obtained during acquisition of an EEG. An artifact is data that misrepresents the EEG. For example, movement within a user that registers on the EEG may be an artifact. Example artifacts include muscle twitches and the like.

Example 1—Exemplary Source Data

In any of the embodiments described herein, a variety of source data can be analyzed including electroencephalography (EEG) data, electrocardiography data (EKG), electrooculography data (EOG), electromyography data (EMG), local field potential (LFP) data, spike train data, wave data including sound and pressure waves, and any data exhibiting where there are differences in dynamic range of power for various frequencies across a frequency spectrum of the data e.g., a 1/f distribution. Source data can include encoded data stored at low power frequency within source data.

Figure 1:
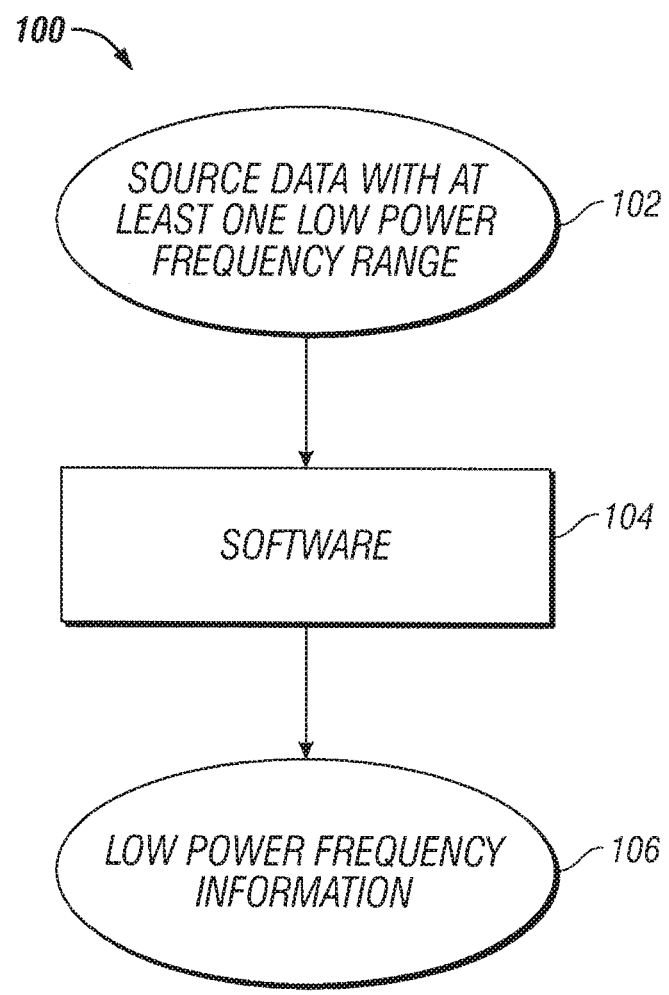
FIG. 1 is a block diagram of an exemplary system for determining low power frequency information from source data with at least one low power frequency range.

Example 2—Exemplary System for Determining Low Power Frequency Information from Source Data with at Least One Low Power Frequency Range FIG. 1 shows an exemplary system 100 for determining low power frequency information from source data with at least one low power frequency range.

Source data with at least one low power frequency range 102 is obtained and input into software 104 to determine low power frequency information 106.

The software 104 can employ any combination of technologies, such as those described herein, to determine low power frequency information 106 for the source data.

Methods for determining low power frequency information from source data with at least one low power frequency range are described in detail below.

Example 3—Exemplary Method for Adjusting Source Data

Figure 2:
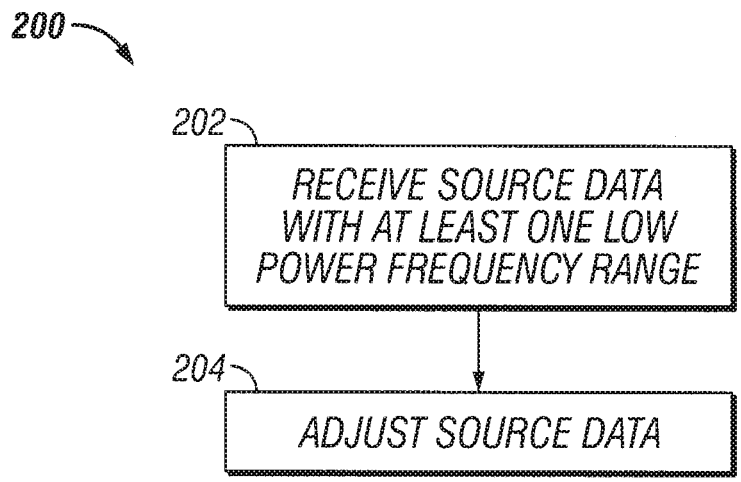
FIG. 2 is a flowchart showing an exemplary method for adjusting source data.

FIG. 2 shows an exemplary method 200 for adjusting source data. For example, the method 200 can be implemented within system 100 of FIG. 1.

At 202, source data with at least one low power frequency range is received. For example, electroencephalography source data for a subject can be received. Source data can be received via a single channel or multiple channels.

At 204, source data is adjusted to increase the dynamic range for power within at least one low power frequency range of the frequency spectrum of the source data as compared to a second higher power frequency range. A number of adjustment techniques described herein, including normalization and frequency weighting can be used. In an embodiment, electroencephalography source data is normalized to increase the low power, higher frequency range data relative to the higher power, lower frequency range data or, more generally, to normalize the powers of the different signal parts.

After the source data is adjusted, various other processing can be done. For example, a visualization of the adjusted source data can be presented. Further, low power frequency information can be extracted from the adjusted source data.

For example, low power frequency information can be extracted from adjusted electroencephalography source data. Higher power frequency information can also be extracted from the adjusted source data.

The method described in this or any of the other examples can be a computer-implemented method performed via computer-executable instructions in one or more computer-readable media. Any of the actions shown can be performed by software incorporated within a signal processing system or any other signal data analyzer system.

Figure 3:
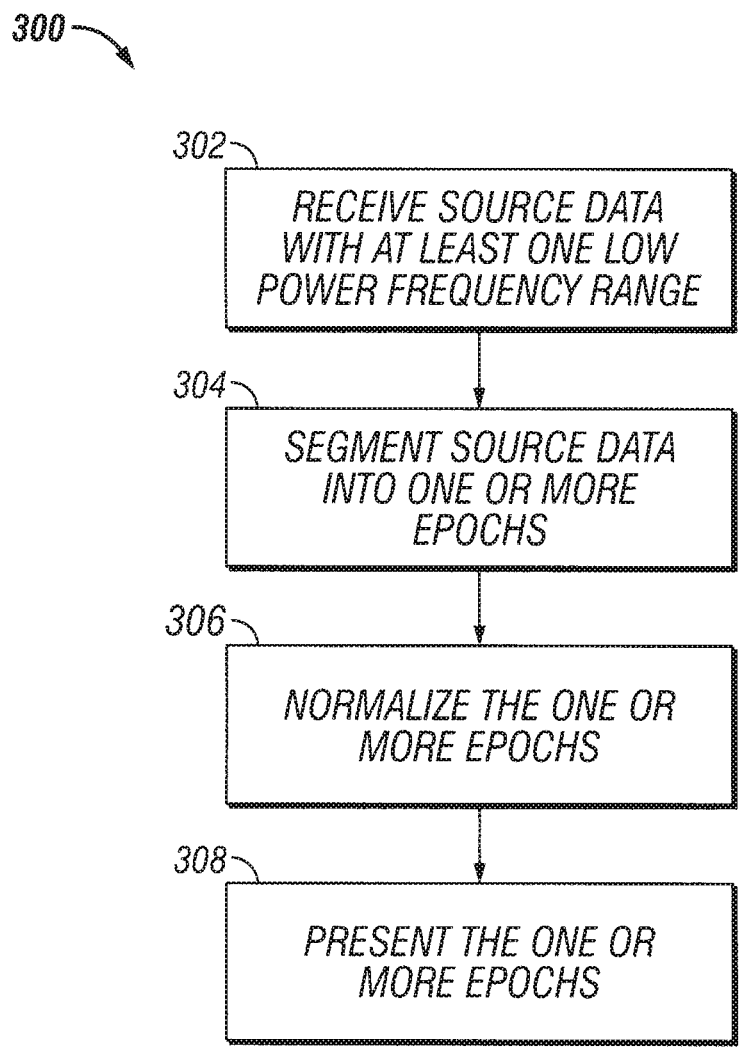
FIG. 3 is a flowchart showing an exemplary method for adjusting source data to account for differences in power over a spectrum of frequencies over time.

Example 4—Exemplary Method for Adjusting Source Data to Account for Differences in Power Over a Spectrum of Frequencies Over Time FIG. 3 shows an exemplary method 300 for adjusting source data to account for differences in power over a spectrum of frequencies over time. For example, the method 300 can be implemented within system 100 of FIG. 1.

At 302, source data with at least one low power frequency range is received. For example, electroencephalography data with at least one low power frequency range can be received. Artifacts in the data can be removed from the source data. For example, artifact data can be manually removed from the source data or automatically filtered out of source data via a filtering (e.g., DC filtering) or data smoothing technique. The source data can also be pretreated with component analysis.

At 304, the source data is segmented into one or more epochs; where each epoch is a portion of data from the series. For example, the source data can be segmented into a plurality of time segments via a variety of separating techniques. Scanning windows and sliding windows can be used to separate the source data into time series increments.

At 306, the one or more epochs are normalized for differences in power of the one or more epochs across time. For example, the power of each epoch at one or more frequencies can be normalized across time to determine appropriate frequency windows for extracting information. Such normalization can reveal low power, statistically significant shifts in power at one or more frequencies (e.g., Delta, Gamma, and the like). Any frequency range can be revealed and utilized for analysis. Information can be calculated for each of the one or more epochs after appropriate frequency windows have been established. Such information can include low frequency power (e.g., Delta power), high frequency power (e.g., Gamma power), standard deviation, maximum amplitude (e.g., maximum of the absolute value of peaks) and the sort. Further calculations can be done on the information calculated for each of the one or more epochs creating information such as Gamma power/Delta power, time derivative of Delta, time derivative of Gamma power/Delta power and the like. Time derivatives can be computed over preceding and successive epochs. After calculating the information, that information can then be normalized across the one or more epochs. A variety of data normalization techniques can be conducted including z-scoring and other similar techniques.

At 308, results of the adjustment of source data to account for differences in power over a spectrum of frequencies over time can be presented as one or more epochs of data. For example, frequency weighted epochs can be presented as adjusted source data.

Figure 4:
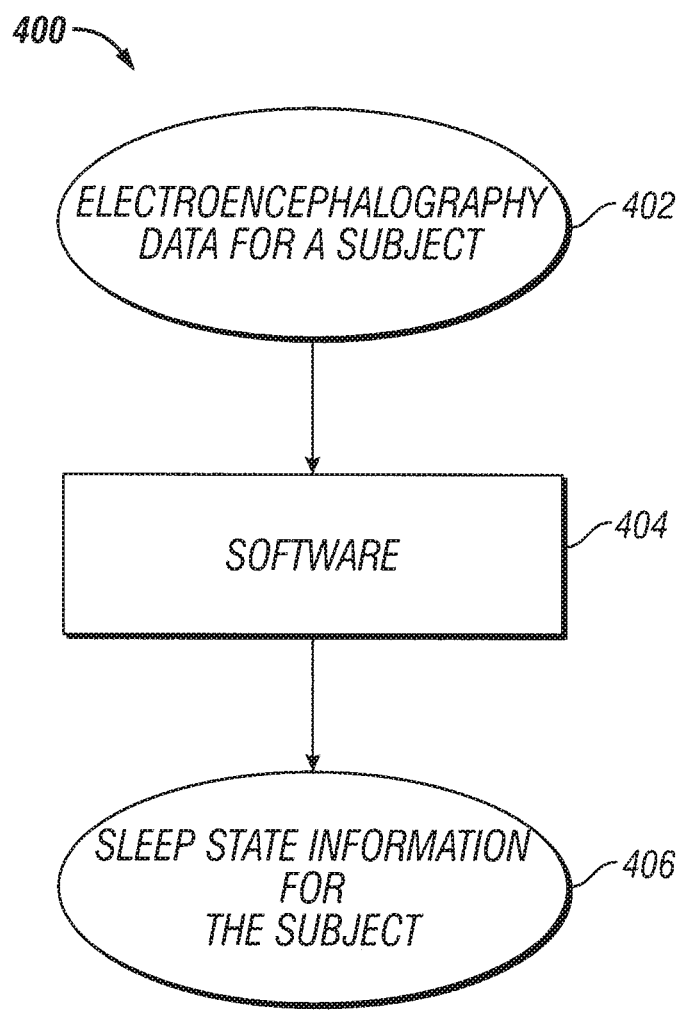
FIG. 4 is a block diagram of an exemplary system for determining sleep state information for a subject.

Example 5—Exemplary System for Determining Sleep State Information for a Subject FIG. 4 shows an exemplary system 400 for determining sleep state information for a subject. Electroencephalography data for a subject 402 is obtained and input into software 404 to determine sleep state information for the subject 406.

The software 404 can employ any combination of technologies, such as those described herein, to determine sleep state information for the subject 406.

Methods for determining sleep state information for a subject are described in detail below.

Figure 5:
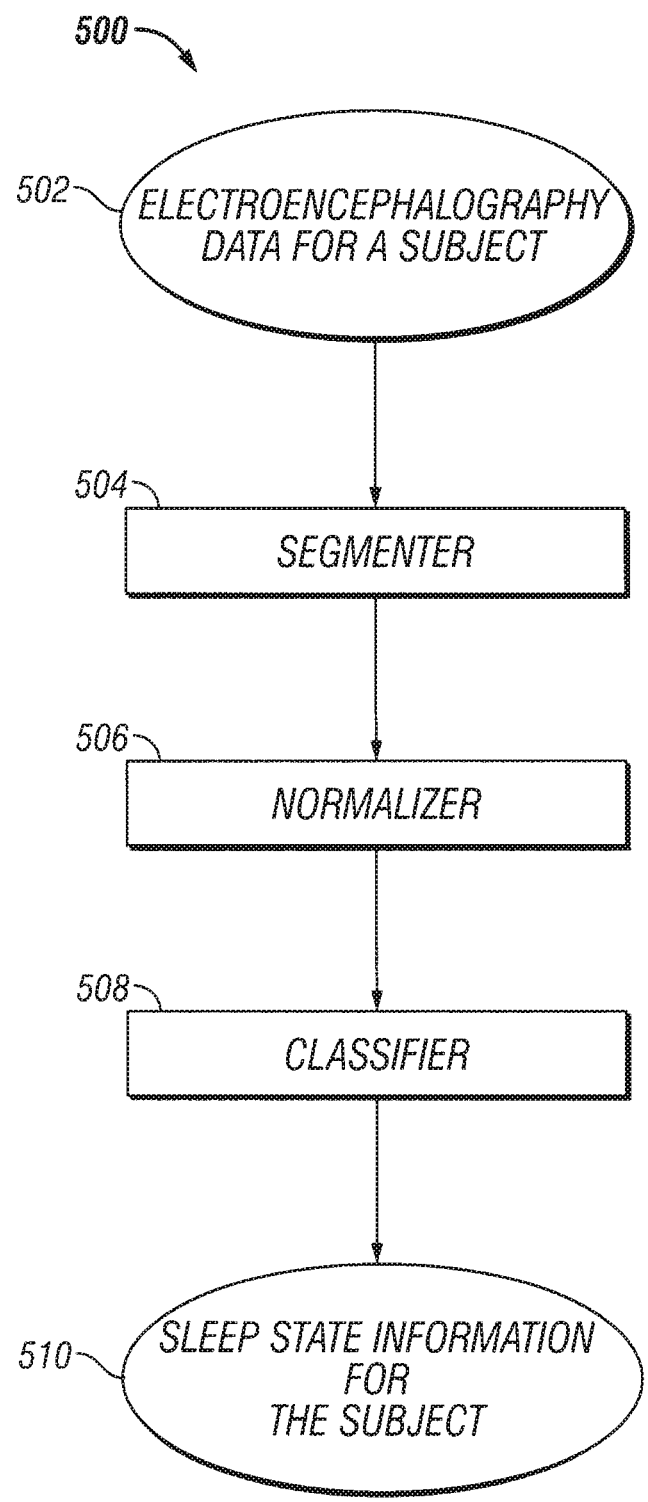
FIG. 5 is a block diagram of another exemplary system for determining sleep state information for a subject.

Example 6—Another Exemplary System for Determining Sleep State Information for a Subject FIG. 5 shows an exemplary system 500 for determining sleep state information for a subject.

Electroencephalography data for a subject 502 is obtained and input into segmenter 504 to segment the data into one or more epochs. In practice, epochs are of similar (e.g., the same) length. Epoch length can be adjusted via a configurable parameter. The one or more epochs, in turn, are input into normalizer 506 to normalize frequency data in the one or more epochs across time, thereby frequency weighting the one or more epochs of electroencephalography data. The one or more frequency weighted epochs are then input into classifier 508 to classify the data into sleep states, thereby generating sleep state information for the subject 510.

Methods for determining sleep state information for a subject are described in detail below.

Example 7—Exemplary Method for Determining Sleep States in a Subject

Figure 6:
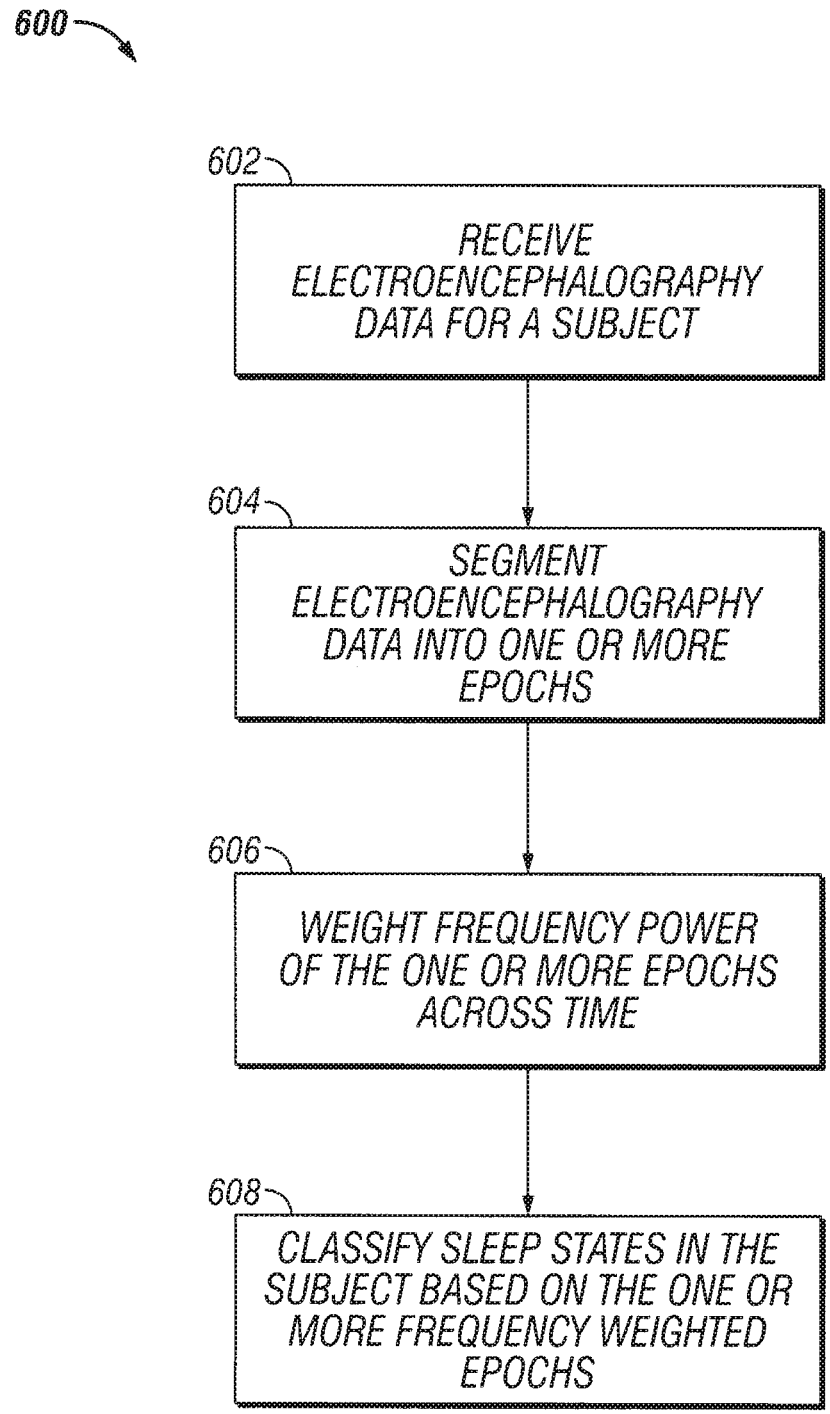
FIG. 6 is a flowchart showing an exemplary method for determining sleep states in a subject.

FIG. 6 shows an exemplary method 600 for determining sleep states in a subject. For example, the method 600 can be implemented within system 500 of FIG. 5 or system 400 of FIG. 4.

At 602, electroencephalography (EEG) data for a subject is received. For example, electroencephalography data, which exhibits lower dynamic range for power in at least one low power first frequency range in a frequency spectrum as compared to a second frequency range in the frequency spectrum, can be received.

At 604, the electroencephalography data for the subject is segmented into one or more epochs. For example, the EEG data can be segmented into one or more epochs via a variety of separating techniques. Scanning windows and sliding windows can be used to separate the EEG data into one or more epochs. The source data can also be filtered via direct current filtering during, prior to, or after segmenting. The source data can also be pretreated with component analysis (e.g., principle or independent component analysis).

Figure 11:
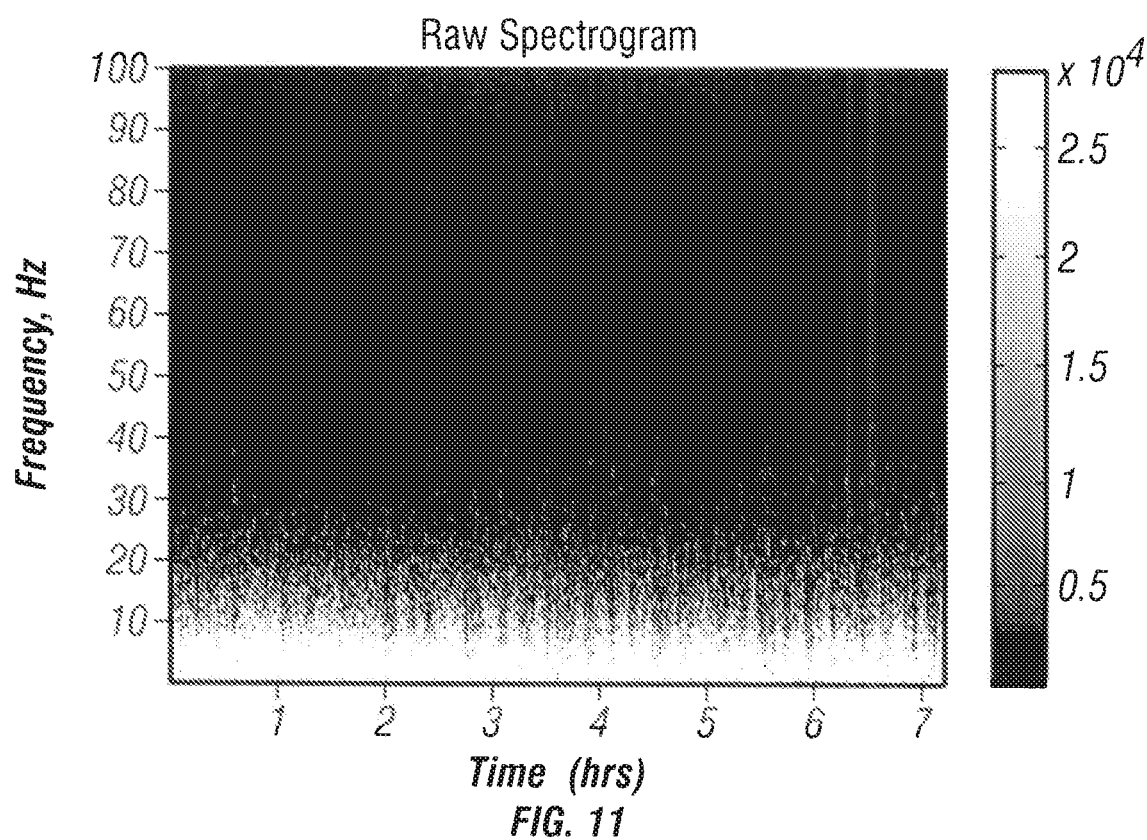
FIG. 11 is a screen shot of an exemplary whole night EEG source data frequency power spectrogram.
Figure 37:
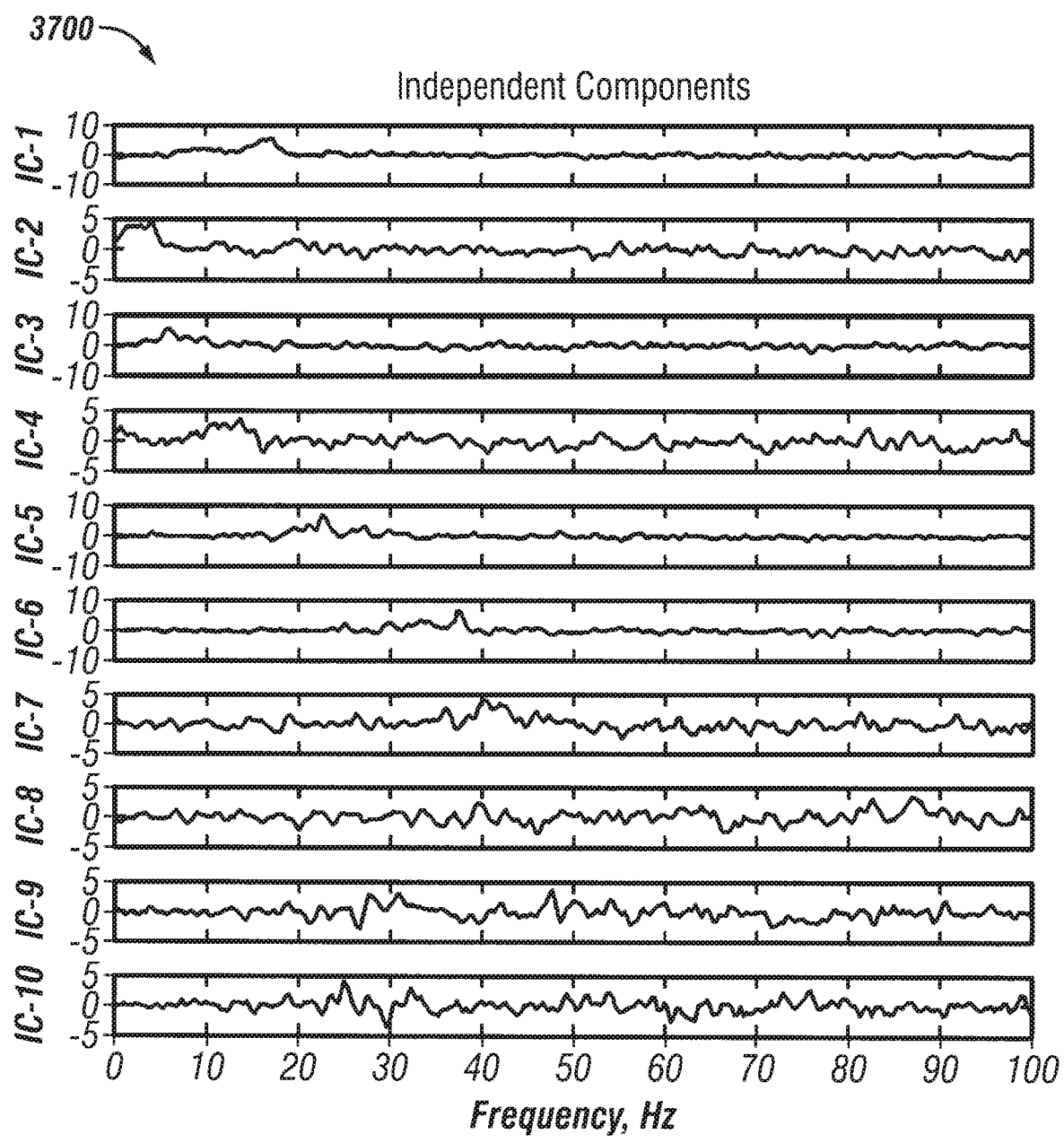
FIG. 37 is a screen shot of an exemplary visualization of independent component analysis applied on a normalized spectrogram to further determine appropriate frequency windows for extracting information.
Figure 38:
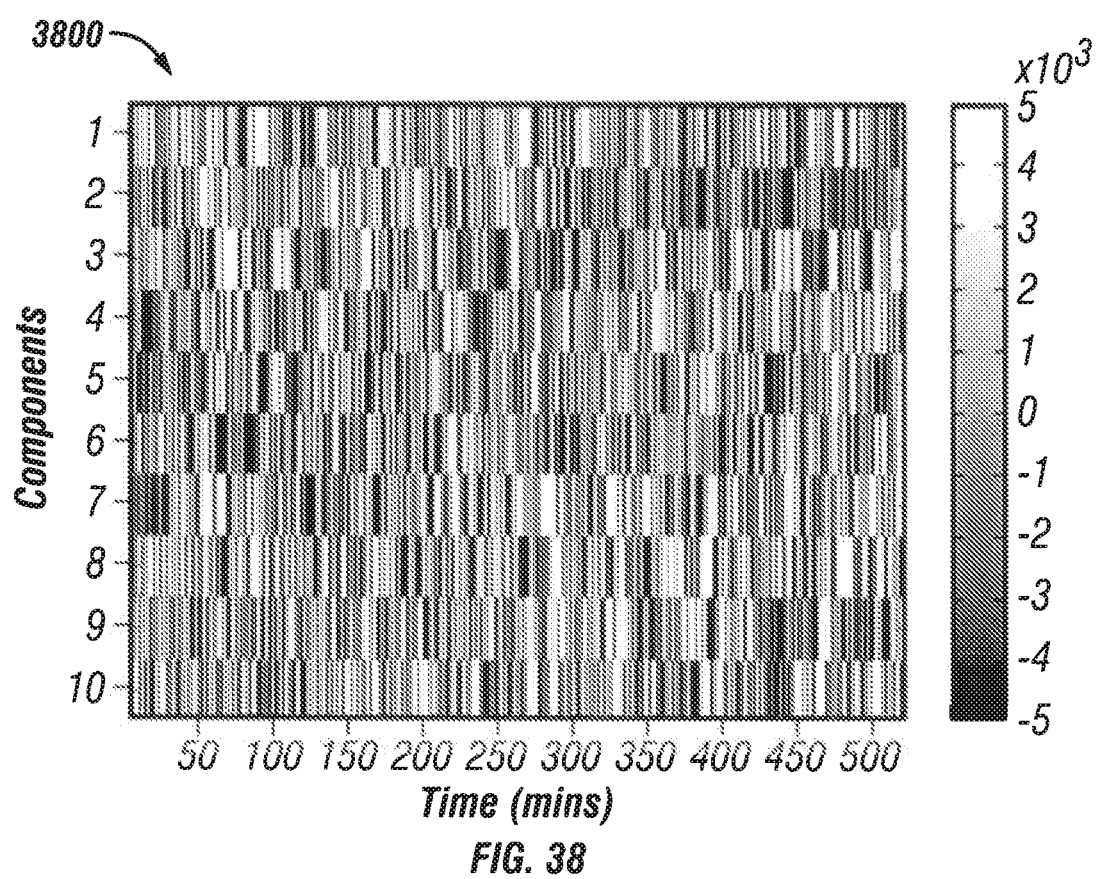
FIG. 38 is a screen shot of an exemplary visualization of independent components of FIG. 37 throughout time.
Figure 39:
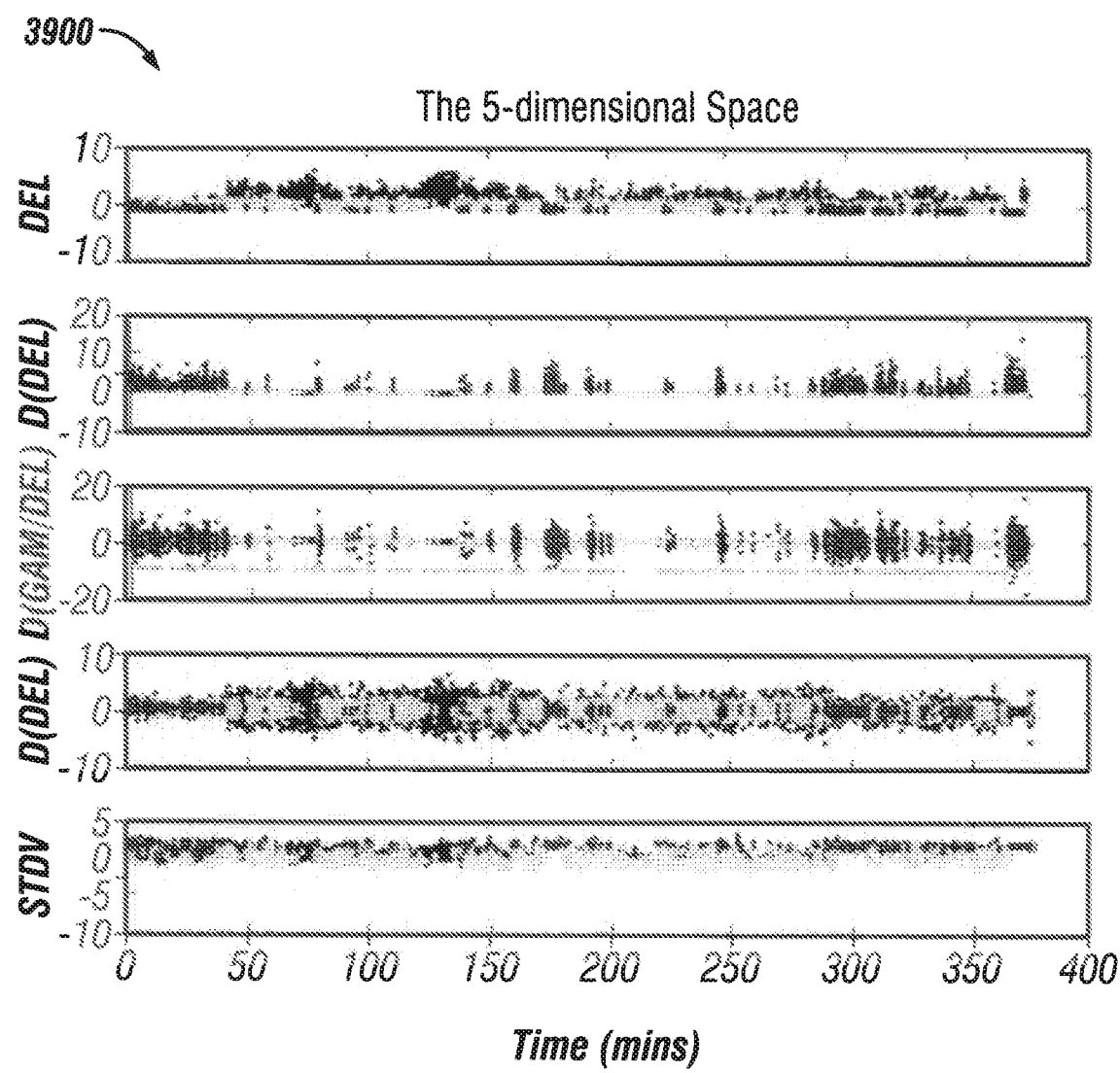
FIG. 39 is a screen shot of a six and a half hour time frame of an exemplary five-dimensional parameter space visualization of frequency bands of the whole night EEG visualization from a human subject with Alzheimer's.

FIG. 11 is a screen shot of an exemplary whole night EEG source data frequency power spectrogram for a subject that has been segmented over three second epochs spaced in 1 second increments. Power range is indicated in the shading, where white shaded regions are higher in power than dark shaded regions. The higher frequencies (e.g., Gamma) therefore At 606, frequency power of the one or more epochs is weighted across time. For example, the power of each epoch at one or more frequencies can be normalized across time to determine appropriate frequency windows for extracting information. Such normalization can reveal low power, statistically significant shifts in power at one or more frequencies (e.g., Delta, Gamma, and the like). Additionally, each epoch can be represented by the frequency with the highest relative power over time to determine appropriate frequency windows for extracting information. Alternatively, component analysis (e.g., principle component analysis (PCA) or independent component analysis (ICA)) can be utilized after normalization to further determine appropriate frequency windows for extracting information. For example, FIGS. 37 and 38 are screen shots of component analysis utilized after normalization to suggest filters (e.g., screen shot 3700) and express independent components throughout time (e.g., screen shot 3800). Any frequency range can be revealed and utilized for analysis.

Information can be calculated for each of the one or more epochs after appropriate frequency windows have been established (e.g., after weighting frequency). Such information can include low frequency power (e.g., Delta power), high frequency power (e.g., Gamma power), standard deviation, maximum amplitude (e.g., maximum of the absolute value of peaks) and the sort. Further calculations can be done on the information calculated for each of the one or more epochs creating information such as Gamma power/Delta power, time derivative of Delta, time derivative of Gamma power/Delta power and the like. Time derivatives can be computed over preceding and successive epochs. After calculating the information, it can then be normalized across the one or more epochs. A variety of data normalization techniques can be conducted including z-scoring and the like.

Figure 12:
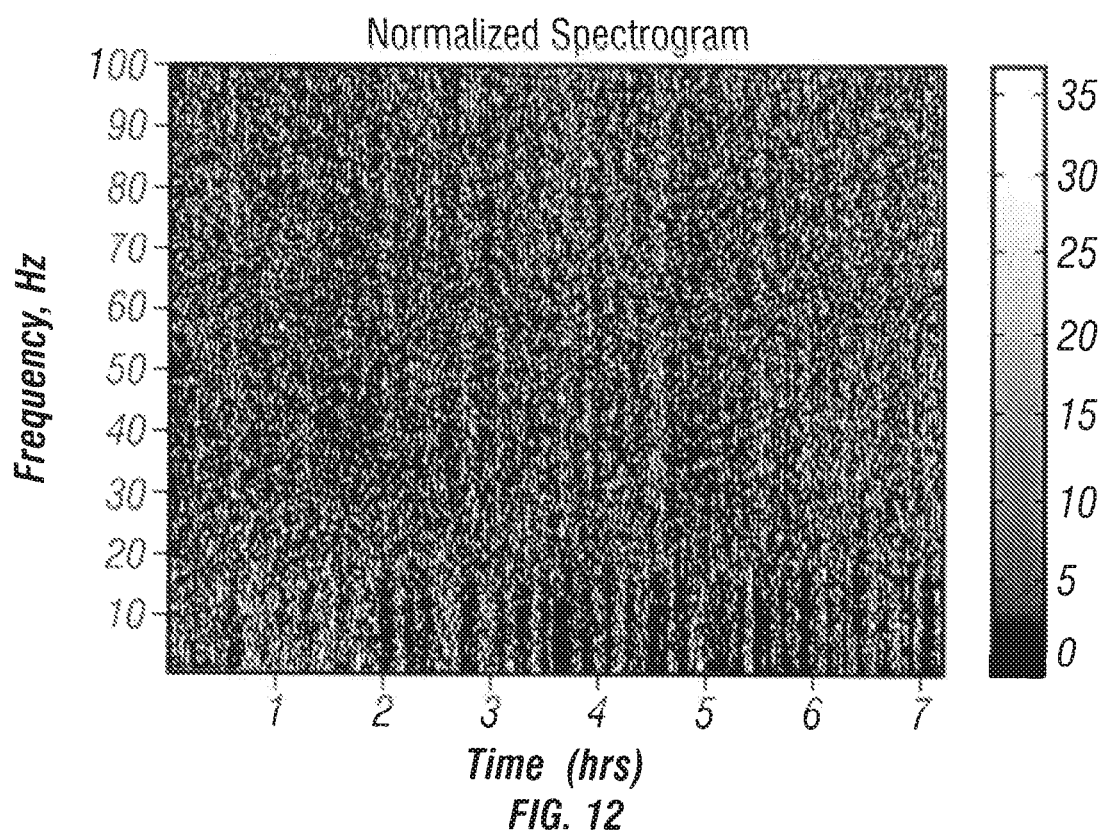
FIG. 12 is a screen shot of the exemplary whole night EEG source data shown in FIG. 11 after an exemplary adjustment technique has been applied.
Figure 13:
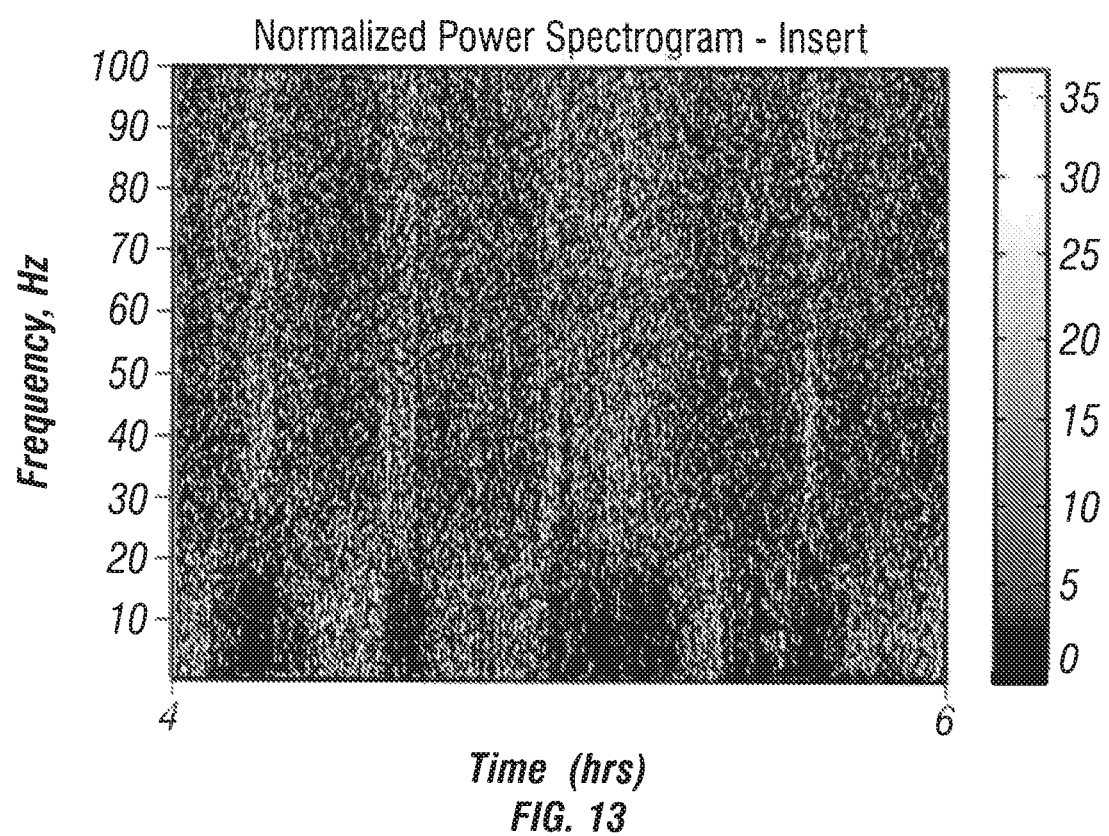
FIG. 13 is a screen shot of a two hour time frame of the exemplary adjusted whole night EEG source data shown in FIG. 12.
Figure 14:
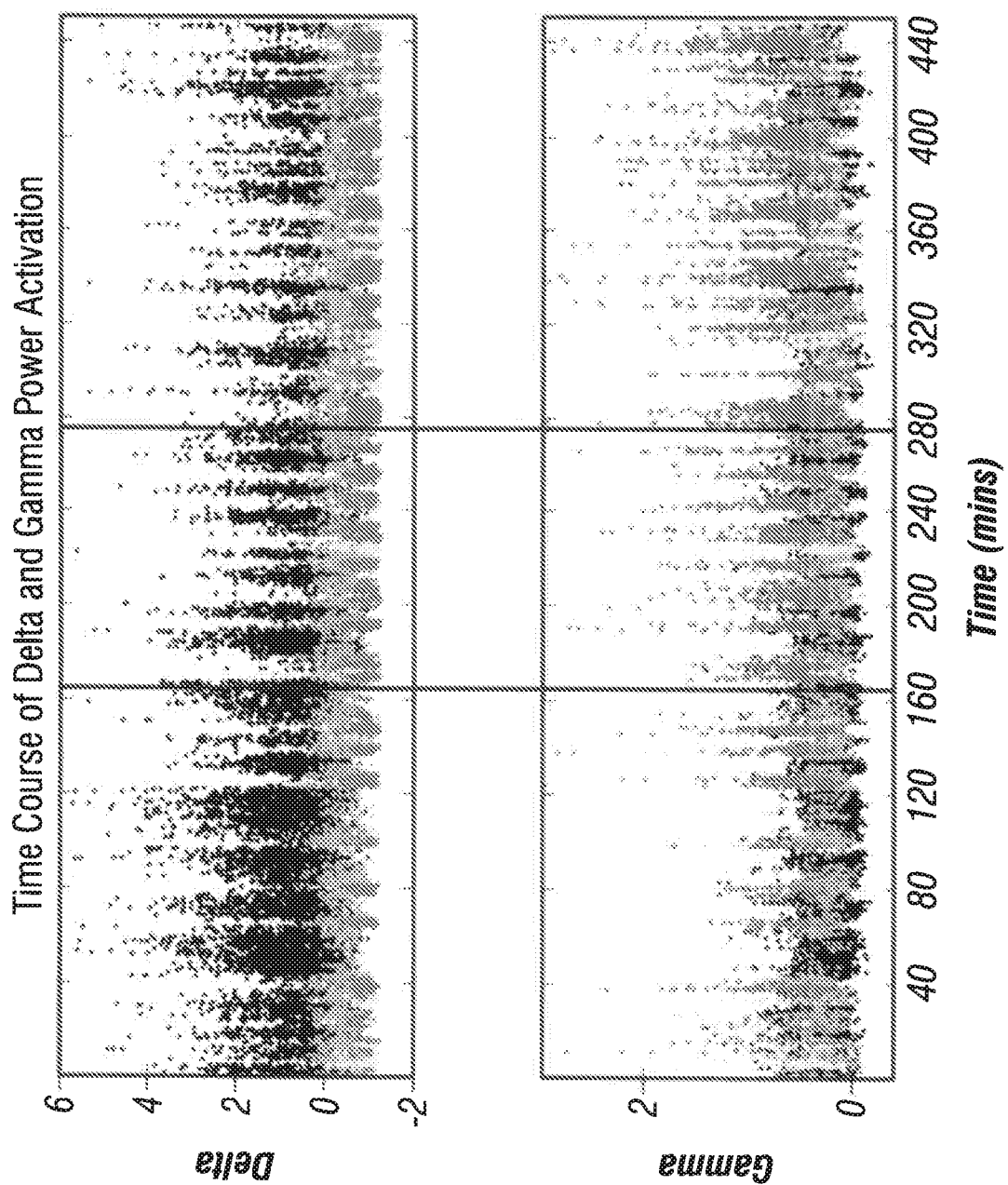
FIG. 14 is a screen shot of an exemplary visualization of high and low power frequency bands within the whole night EEG spectrogram shown in FIG. 12.
Figure 15:
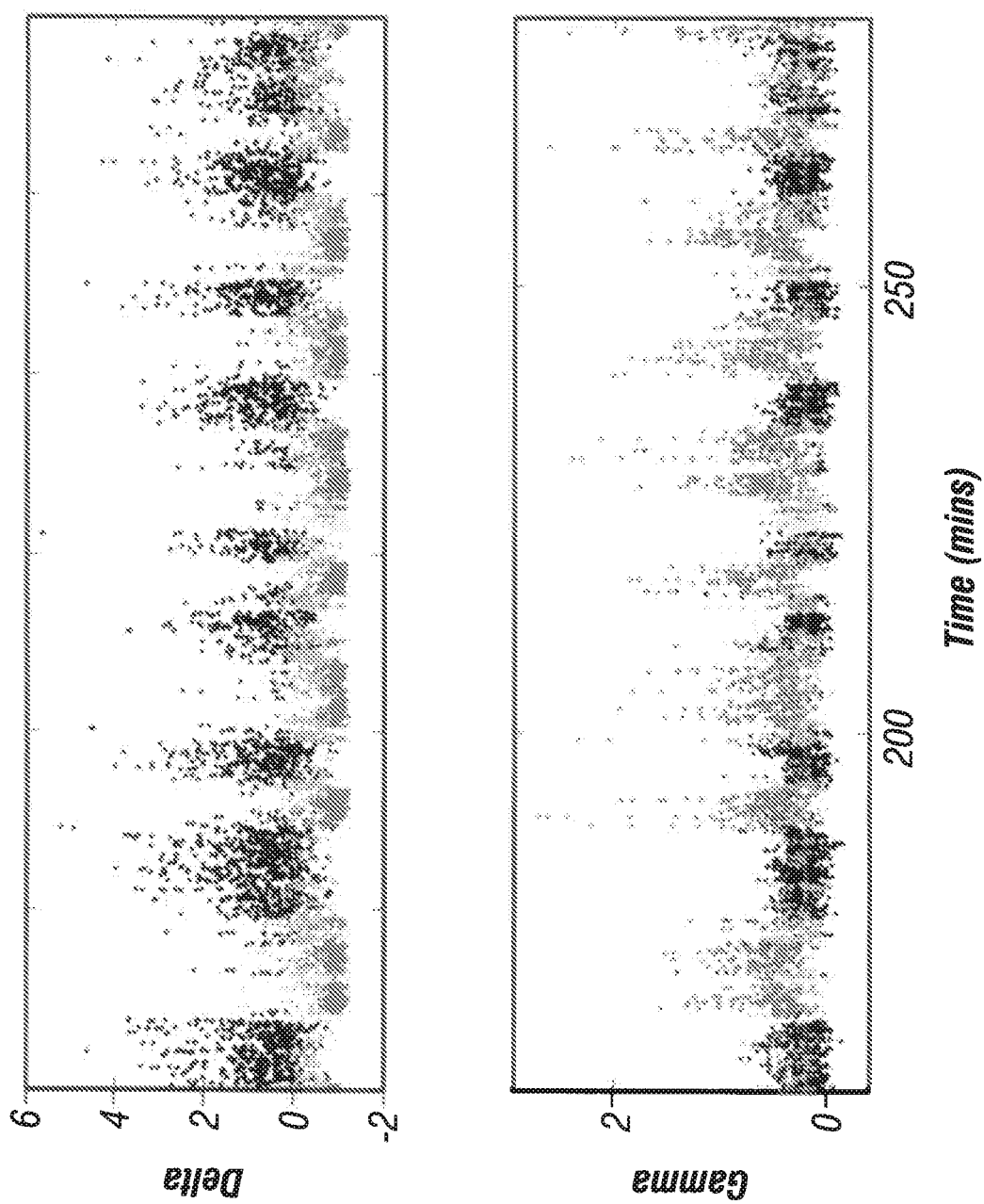
FIG. 15 is a screen shot of a two hour and forty minutes time frame of the exemplary visualization of high and low power frequency bands within the whole night spectrogram shown in FIG. 14.

FIG. 12 is a screen shot of the exemplary whole night EEG source data shown in FIG. 11 after an exemplary frequency power of the one or more epochs has been weighted across time. The higher frequency data is now more clearly visible. FIG. 13 is a screen shot of a two hour time frame of the exemplary adjusted whole night EEG source data shown in FIG. 12. FIG. 14 is a screen shot of an exemplary visualization of high (e.g., Gamma) and low (e.g., Delta) power frequency bands within the whole night EEG spectrogram shown in FIG. 12. FIG. 15 is a screen shot of a two hour and forty minutes time frame of the exemplary visualization of high and low power frequency bands shown in FIG. 14.

Figure 16:
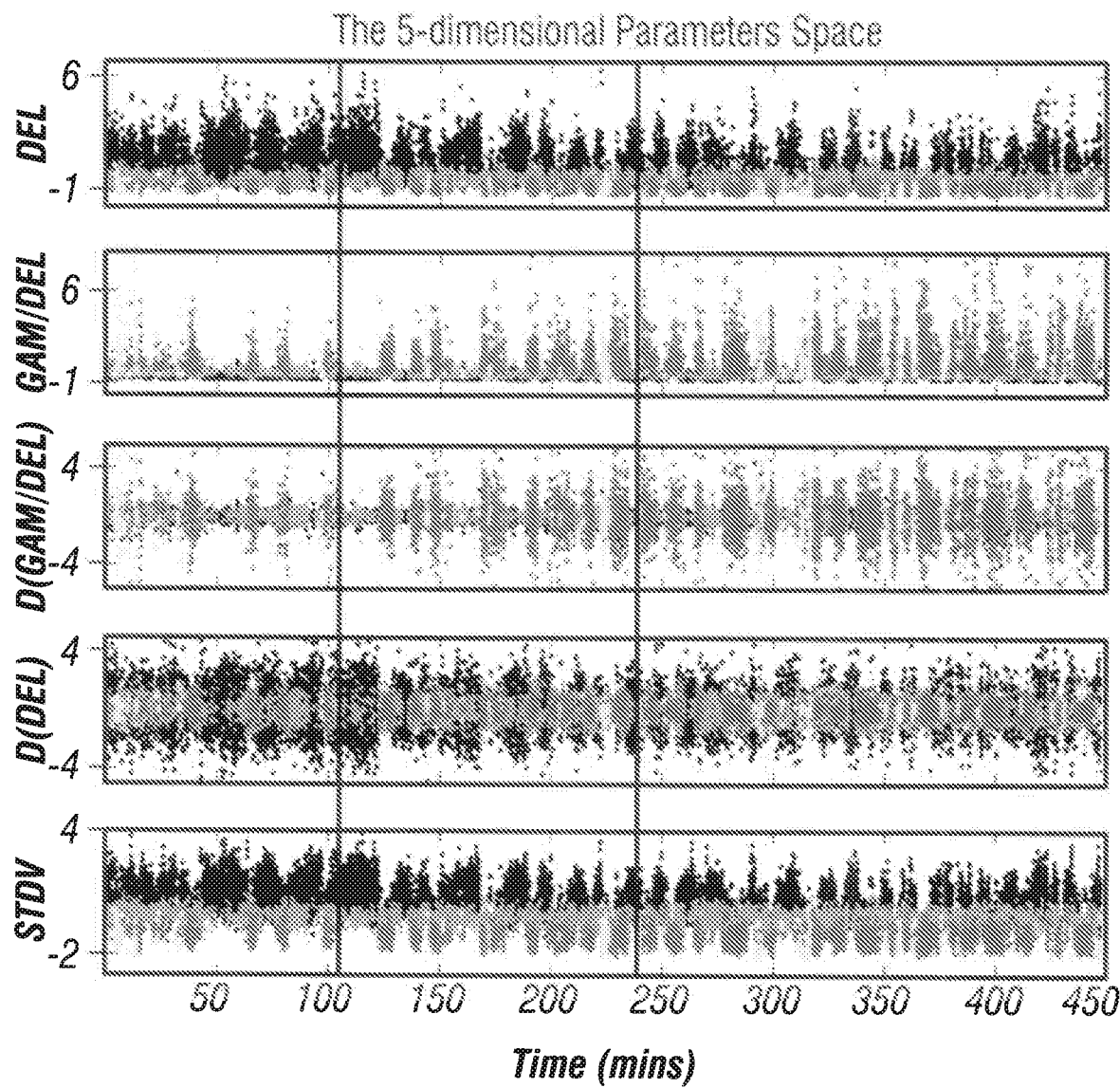
FIG. 16 is a screen shot of an exemplary five-dimensional parameter space visualization of the whole night EEG spectrogram of FIG. 12.
Figure 17:
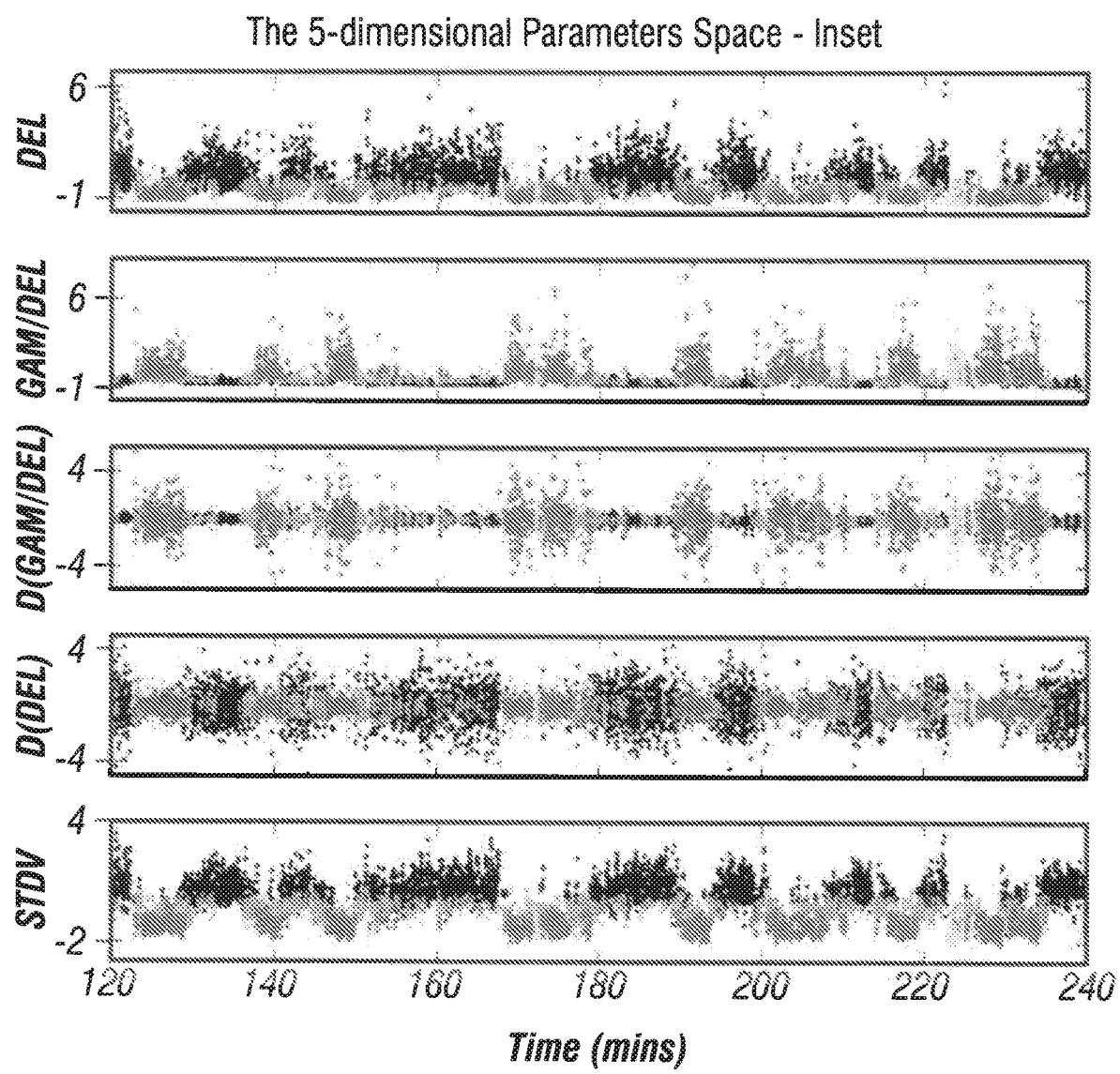
FIG. 17 is a screen shot of a two hour time frame of the exemplary five-dimensional parameter space visualization of the whole night EEG visualization shown in FIG. 16.

FIG. 16 is a screen shot of an exemplary five-dimensional parameter space visualization of the whole night EEG spectrogram of FIG. 12. The five parameters (e.g., variables) are information calculated for each of the one or more epochs after weighting frequency. FIG. 17 is a screen shot of a two hour time frame of the exemplary five-dimensional parameter space visualization of the whole night EEG visualization shown in FIG. 16.

At 608, sleep states in the subject are classified based on the one or more frequency weighted epochs. For example, the one or more frequency weighted epochs can be clustered by any variety of clustering techniques including k-means clustering. The clustering can be done on information calculated from the epochs (e.g., Delta power, Gamma power, standard deviation, maximum amplitude (Gamma/Delta), time derivative of Delta, time derivative of (Gamma/Delta, and the sort). Component analysis (e.g., PCA or ICA) can be used to determine the parameter space (e.g., types of information used) in the clustering.

Subsequent to clustering, sleep state designations can be assigned to the epochs. Sleep state designated epochs can then be presented as representations of sleep states in the subject for the period of time represented by the epoch. Classification can also incorporate manually determined sleep states (e.g., manually determined "awake" versus "sleeping" sleep states). Additionally, artifact information (e.g. movement data, poor signal data, or the like) can be utilized in the classification.

Example 8—Exemplary Sleep State Classification Techniques

Epochs can be classified according to the sleep states they represent. An epoch can be classified according to normalized variables (e.g., information calculated for an epoch) based on high frequency information, low frequency information, or both high and low frequency information. For example, REM sleep state epochs can have higher relative power than SWS at higher frequencies and lower relative power than SWS at lower frequencies. Similarly, SWS sleep state epochs can have lower relative power than REM at higher frequencies and higher relative power than REM at lower frequencies. Additionally, epochs initially classified as both NREM and NSWS sleep (e.g., epochs having low relative power at both higher and lower frequencies) can be classified as intermediate sleep and epochs classified as both REM and SWS sleep (e.g., epochs having high relative power at both higher and lower frequencies) can be classified as outliers. Further, epochs initially classified as both NREM and NSWS sleep can be classified as intermediate stage I sleep and epochs initially classified as both REM and SWS sleep can be classified as intermediate stage II sleep. Additionally, sleep states can be split in the classifying to look for spindles, k-complexes, and other parts. Any group of epochs initially classified as one sleep state can be split into multiple sub-classified sleep states according to increasing levels of classification detail. For example, a group of epochs classified as SWS can be reclassified as two distinct types of SWS.

Example 9—Exemplary Artifact Classification Techniques

Artifact data (e.g. movement data, poor signal data, and the like) can also be used in sleep state classification. For example, artifacts can be used to analyze whether epochs initially assigned a sleep state designation should be reassigned a new sleep state designation due to neighboring artifact data. For example, an epoch assigned a sleep state designation of REM that has a preceding movement artifact or awake epoch can be reassigned a sleep state designation of awake. Further, for example, an artifact epoch that has a succeeding SWS epoch can be reassigned a sleep state designation of SWS because there is a high likelihood that the epoch represents a large SWS sleep epoch rather than a large movement artifact which is more common during wakefulness. In such ways, for example, artifact data can be utilized in a data smoothing technique.

Example 10—Exemplary Smoothing Techniques

Any variety of data smoothing techniques can be used during the assigning of sleep states. For example, numbers (e.g., 0 and 1) can be used to represent designated sleep states. Neighboring epochs' sleep state designation numbers can then be averaged to determine if one of the epochs is inaccurately assigned a sleep state designation. For example, abrupt jumps from SWS-NSWS-SWS (and REM-NREM-REM) are rare in sleep data. Therefore, should a group of epochs be assigned sleep state designations representing abrupt jumps in sleep states, smoothing techniques can be applied to improve the accuracy of the assigning.

For example, in a scenario in which 0 represents SWS, 1 represents NSWS and the following sleep state designations existed for five neighboring epochs, 00100, then an average of the five sleep states would be 0.2. In such an instance, the middle epoch initially assigned a sleep designation of 1 (SWS) would be reassigned a sleep state designation of 0 (NSWS). The same technique could be used for REM versus NREM where a second set of sleep designations for the same five neighboring epochs is determined. For example, 1 can represent REM, 0 can represent NREM, and the following designations can exit for the five neighboring epochs, 00100. Again, the average of the five sleep states would be 0.2. Again, the middle epoch initially assigned a designation of 1 (REM) would be reassigned a sleep state designation of 0 (NREM). Such smoothing techniques can improve the accuracy of assigning sleep state designations.

Example 11—Exemplary Method for Classifying Sleep States in a Subject

Figure 7:
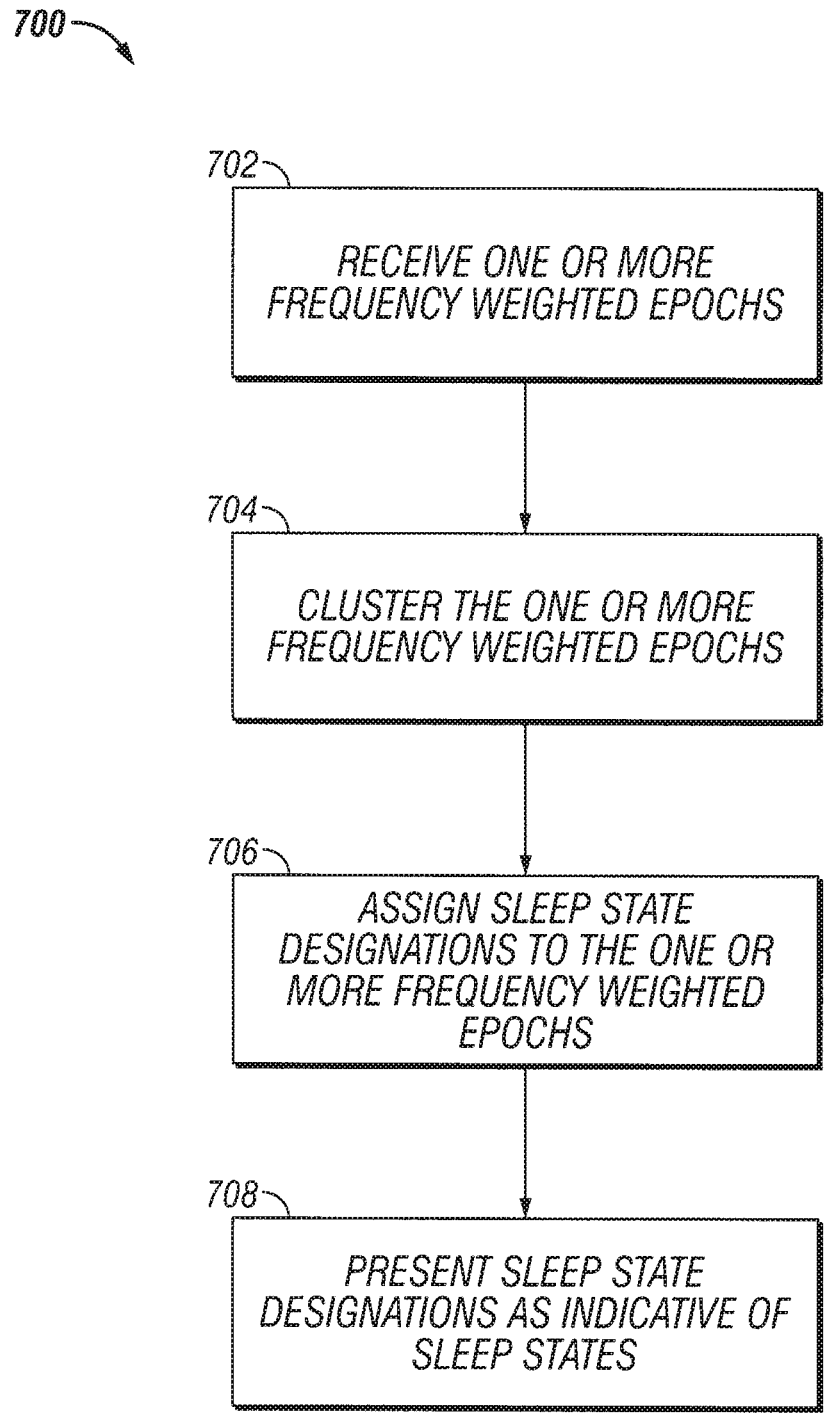
FIG. 7 is a flowchart showing an exemplary method for classifying sleep states in a subject.

FIG. 7 shows in a flowchart an exemplary method 700 for classifying sleep states in a subject. For example, the method 700 can be implemented within system 500 of FIG. 5, system 400 of FIG. 4 or within the classifying 608 of method 600.

At 702, one or more frequency weighted epochs are received. For example, frequency weighted epochs determined from the weighting 606 of method 600 can be received.

Figure 18:
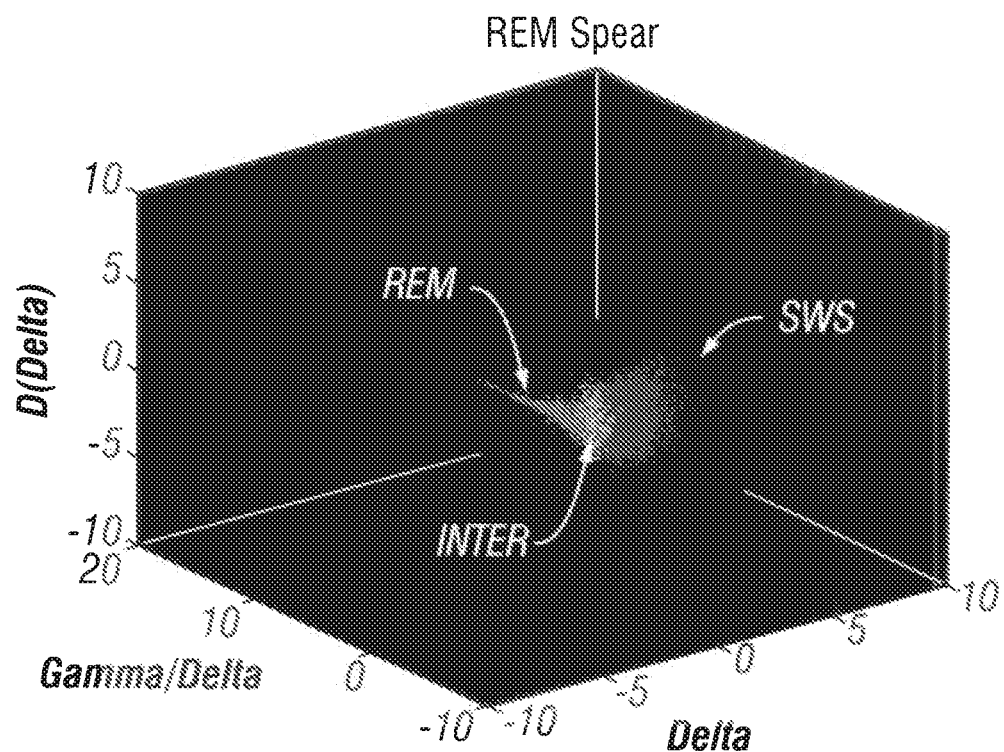
FIG. 18 is a screen shot of an exemplary-visualization of classified sleep states based on EEG spectrogram data.
Figure 19:
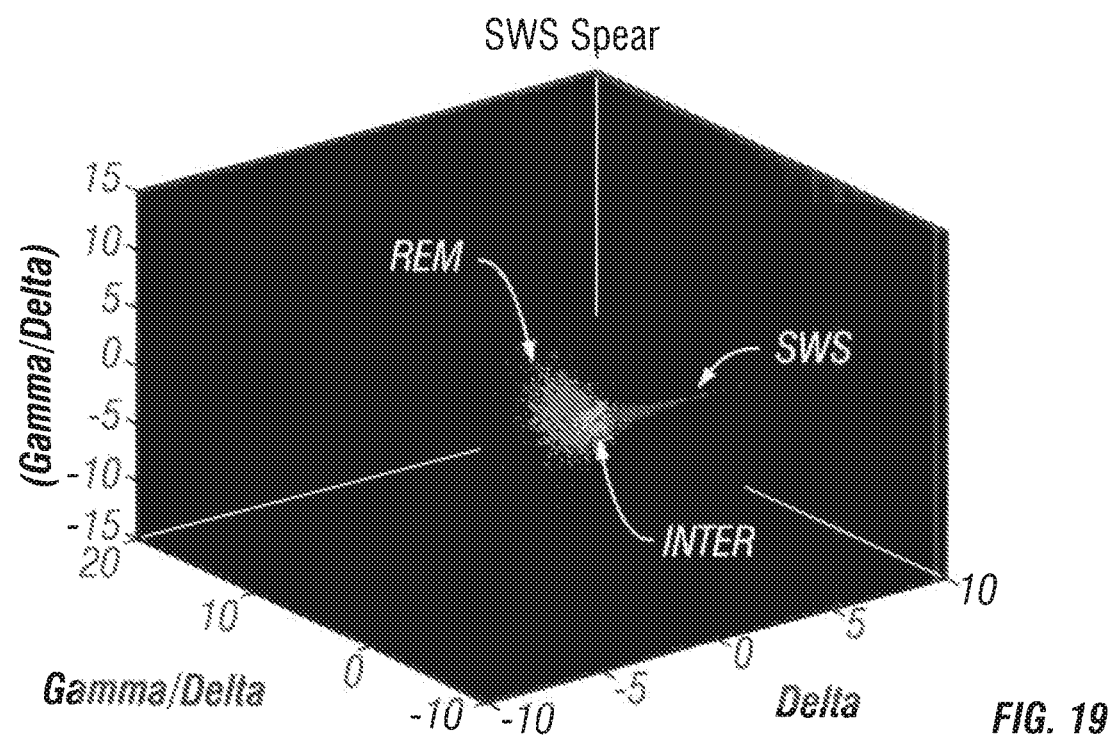
FIG. 19 is a screen shot of another exemplary visualization of classified sleep states based on EEG spectrogram data.
Figure 20:
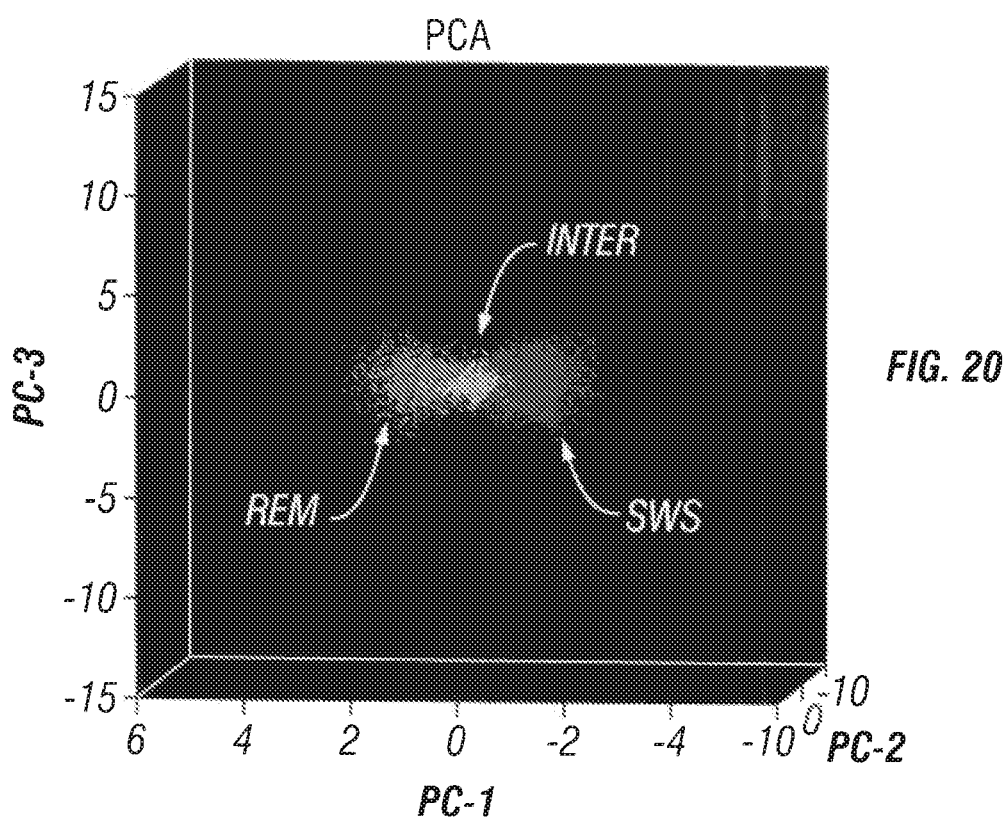
FIG. 20 is a screen shot of yet another exemplary visualization of classified sleep states based on EEG spectrogram data.
Figure 21:
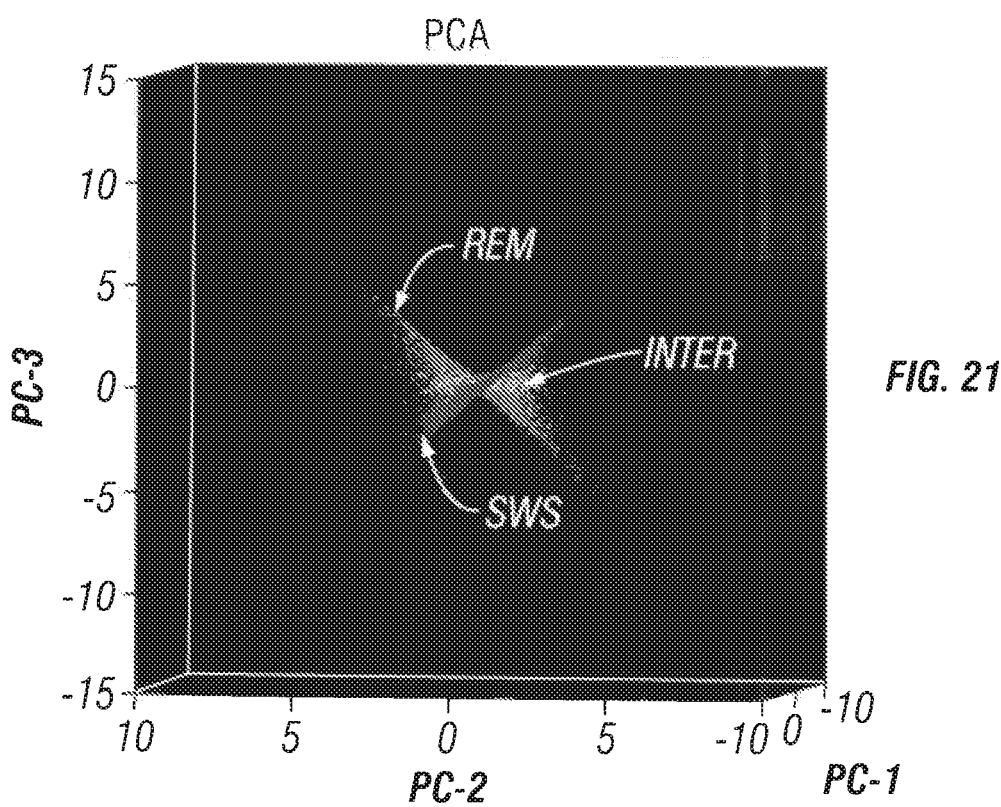
FIG. 21 is a screen shot from another vantage point of the exemplary visualization of classified sleep states based on EEG spectrogram data of FIG. 20.
Figure 22:
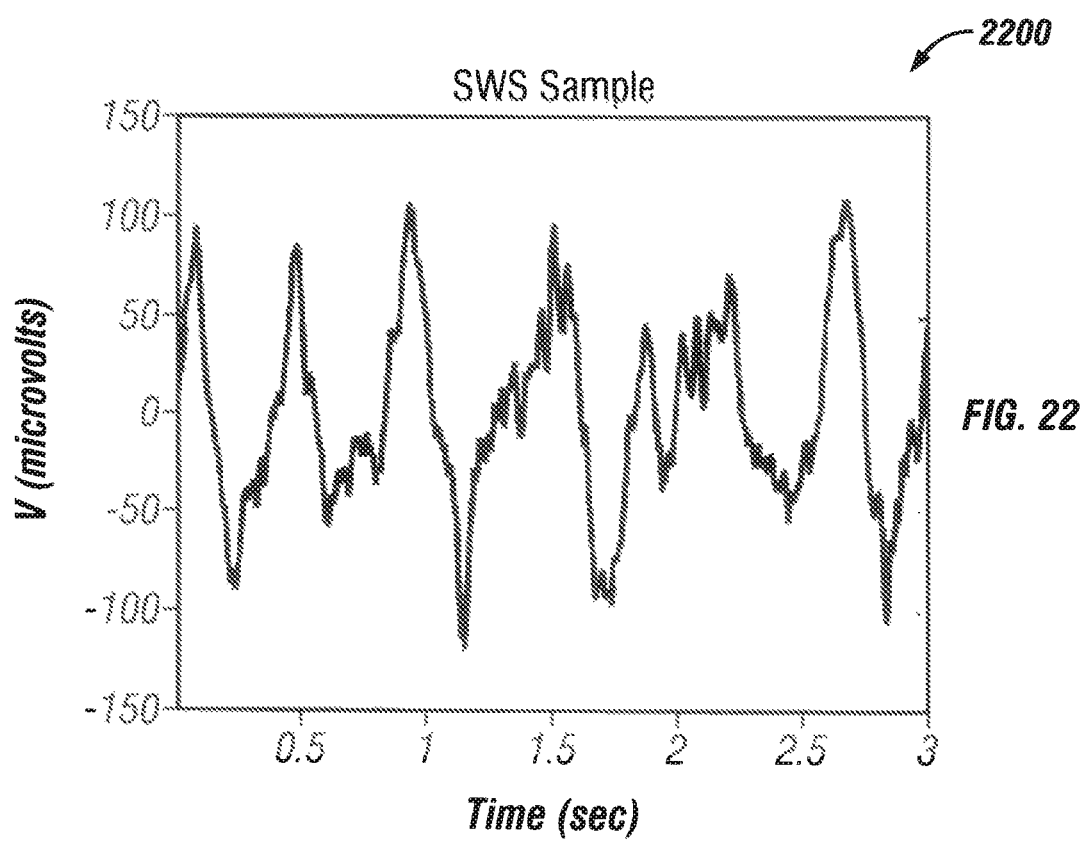
FIGS. 22, 23, 24 and 25 are screen shots of canonical spectra representative of frequency weighted epochs designated as distinct sleep states in a subject for a period of time.
Figure 23:
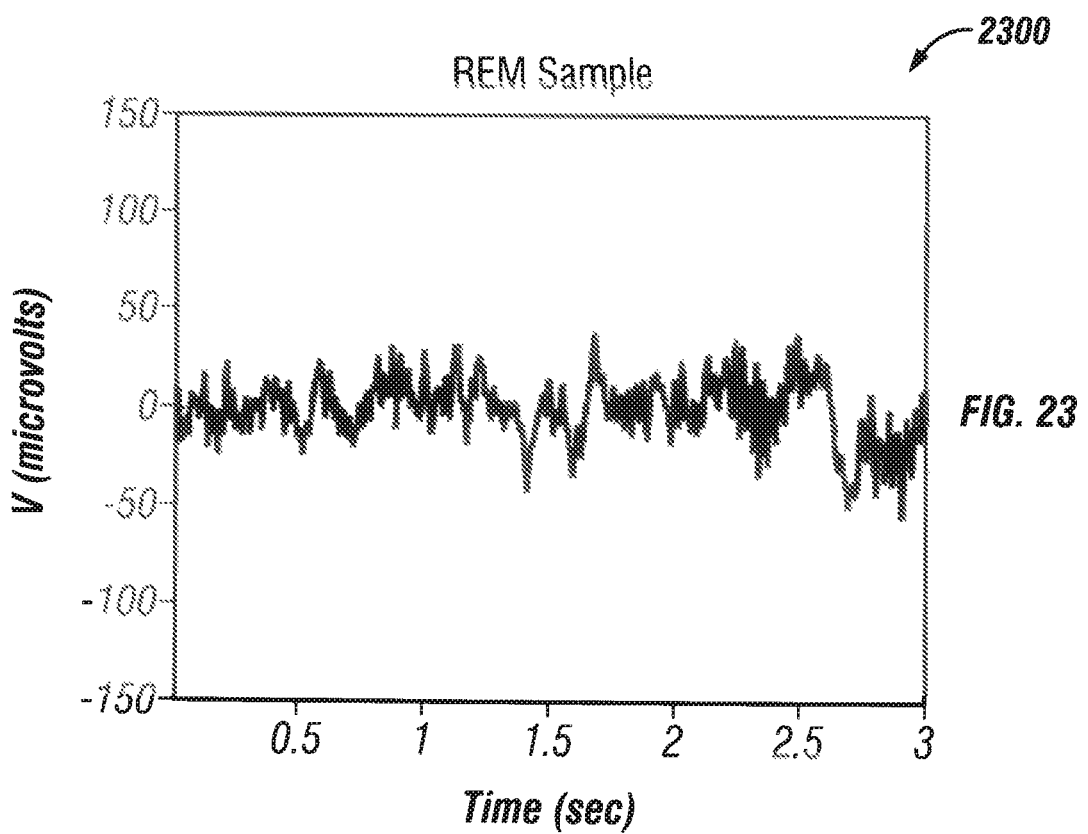

At 704, the one or more frequency weighted epochs are clustered. For example, the one or more frequency weighted epochs can be clustered by any variety of clustering techniques including k-means clustering. The clustering can be done on information calculated from the epochs (e.g., Delta power, Gamma power, standard deviation, maximum amplitude (Gamma/Delta), time derivative of Delta, time derivative of Gamma/Delta, and the sort). Exemplary visualizations of clustered sleep states are shown in FIGS. 18 and 19. FIG. 18 shows epochs clustered via Delta, Gamma/Delta, and the time derivative of Delta. In such a manner, REM-like epochs form a visual spear point shape. FIG. 19 shows epochs clustered via Delta, Gamma/Delta, and the time derivative of (Gamma/Delta). In such a manner, SWS-like epochs form a visual spear point shape. Additional exemplary visualizations of clustered sleep states are shown in FIGS. 20 and 21, in which clustering was done using parameters (e.g., variables) derived via principle component analysis.

At 706, the one or more clustered, frequency weighted epochs are assigned sleep state designations. For example, an epoch with significant relative power at low frequency can be assigned a slow wave sleep designation and an epoch with significant relative power at high frequency can be assigned a rapid eye movement sleep designation. For example, REM sleep can have higher Gamma/Delta and a higher absolute value of the time derivative of (Gamma/Delta) compared to SWS, whereas SWS can have higher delta and a higher absolute value of the time derivative of delta than REM sleep. Further, for example, standard deviation can be used in assigning sleep state designations. It is possible for the same epoch to be assigned both a slow wave sleep designation and a rapid eye movement sleep designation. In such cases, the epoch can be reassigned a new sleep state designation of outlier or intermediate stage II sleep. Alternatively, an epoch can be assigned both a non-slow wave sleep designation and a non-rapid eye movement sleep designation. In such cases, the epoch can be reassigned a new sleep state designation of intermediate sleep or intermediate stage I sleep. For example, when high frequency is expressed by dividing it by Delta and the parameter space Delta, Gamma/Delta, abs(derivative(Delta)), abs(derivative (Gamma/Delta)), and, optionally, standard deviation, then intermediate sleep designation can be the intersection between NREM and NSWS while outlier designation can be the intersection between REM and SWS. Alternatively, for example, if Delta alone or with standard deviation is used to determine SWS from NSWS and gamma alone or with abs (derivative(Delta)) alone or with standard deviation is used to determine REM from NREM, then intermediate stage I sleep designation can be the intersection between NREM and NSWS while intermediate stage II sleep designation can be the intersection between REM and SWS. Any variety of data smoothing techniques can be used during the assigning of sleep states. Artifact data can also be used during the assigning of sleep states.

Figure 29:
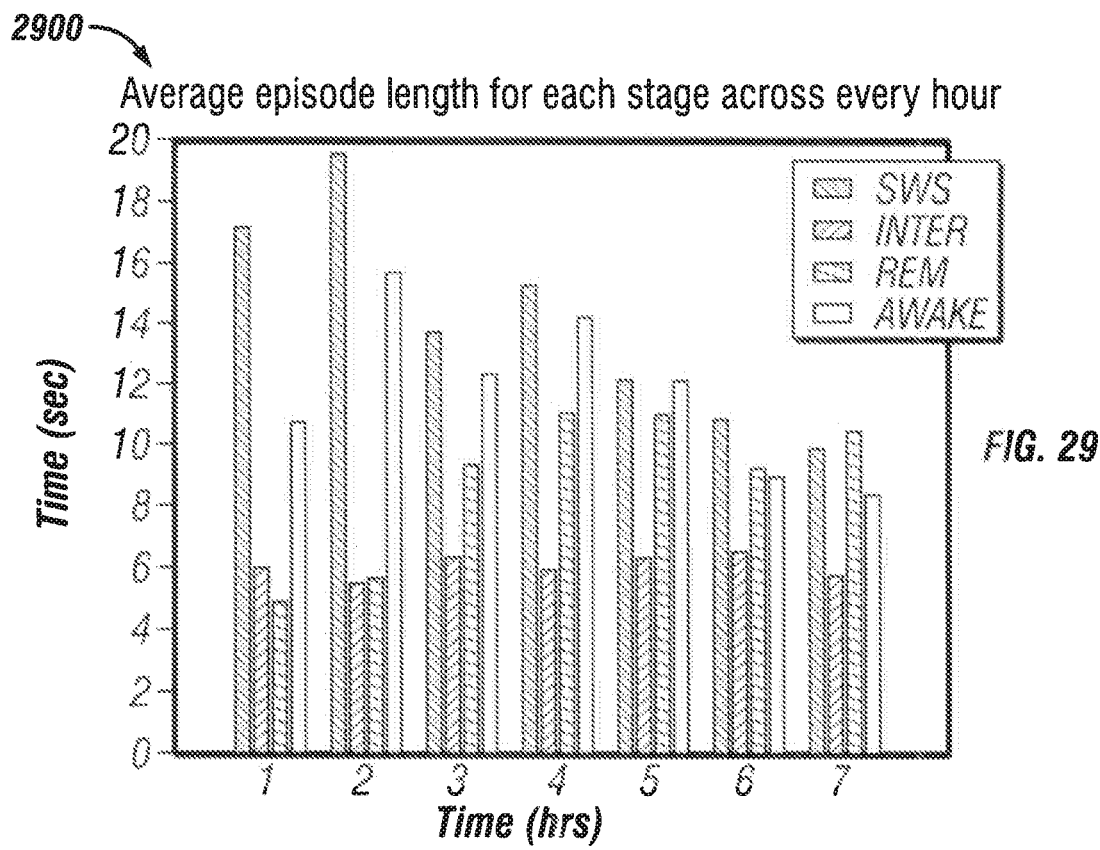
Figure 30:
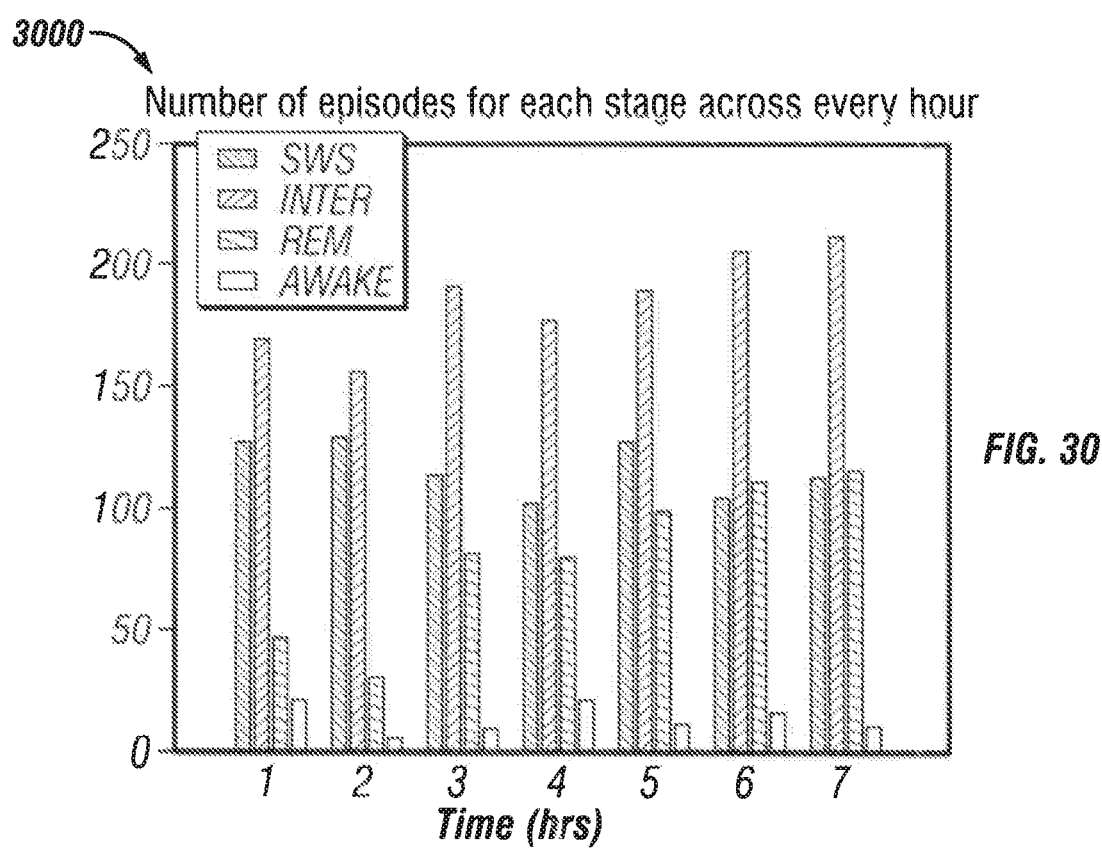
Figure 31:
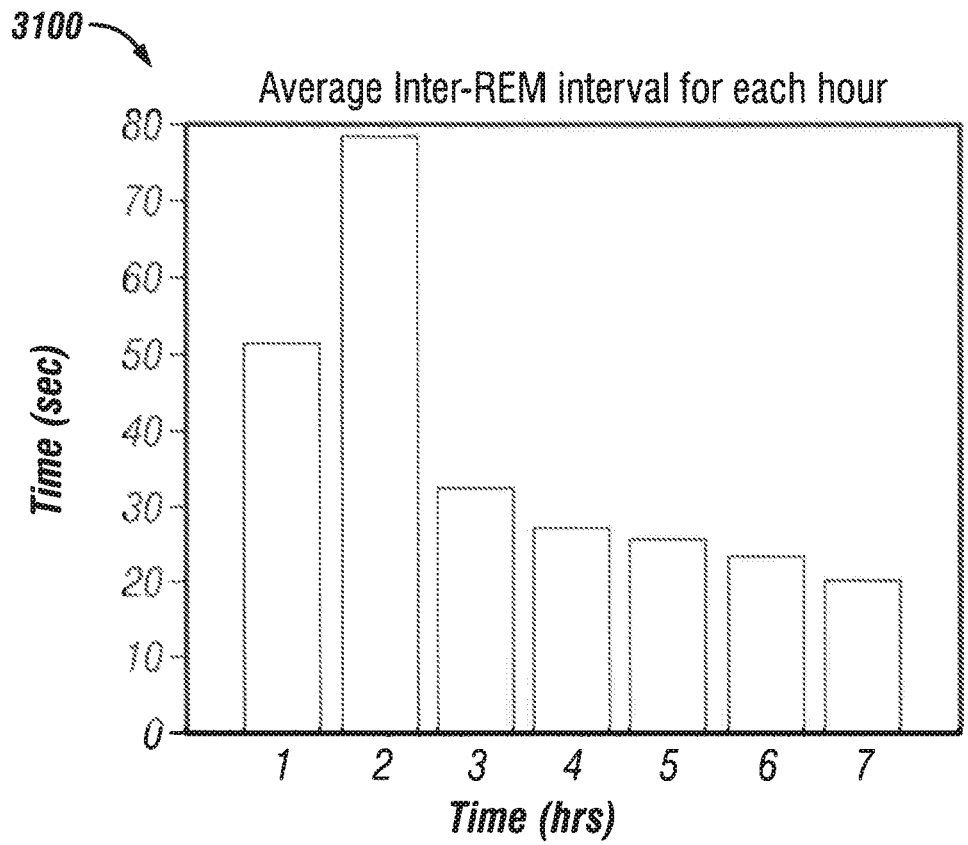
Figure 32:
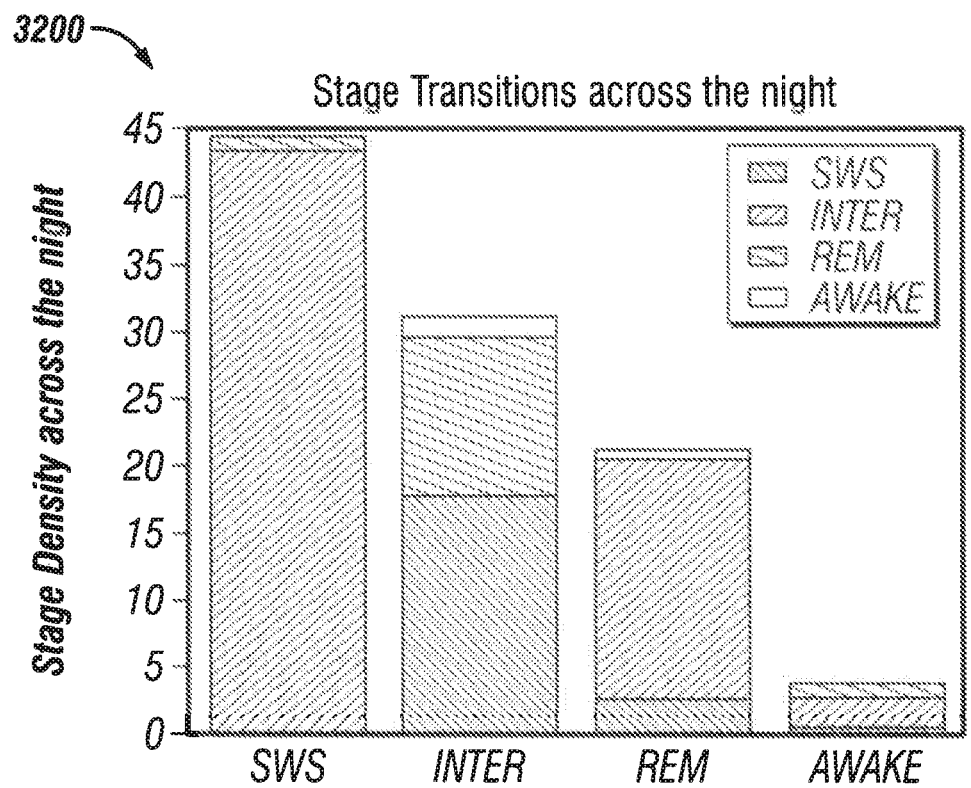

At 708, sleep state designations are presented as indicative of sleep states for the period of time represented by the one or more epochs. The sleep states can be presented in the form of sleep statistics across time. For example, FIGS. 28, 29, 30, 31, and 32 depict presentations of sleep statistics for sleep state designated epochs as a function of time. For example in FIG. 28, a screen shot 2800 depicts sleep state density as a percentage for each sleep state type per hour during a night of electroencephalography data for a subject. In FIG. 29, a screen shot 2900 depicts average episode length for each sleep stage across every hour. In FIG. 30, a screen shot 3000 depicts number of episodes for each sleep stage across every hour. In FIG. 31, a screen shot 3100 depicts average time intervals between successive REM sleep state intervals for each hour. In FIG. 32, a screen shot 3200 depicts stage transitions across the night.

Additionally, one or more frequency weighted epochs can be presented as canonical spectra representative of the sleep state in the subject for the period of time represented by the one or more epochs having similar sleep state designations. For example, an epoch within the middle of a group of epochs designated as having the same sleep state designations can be selected and its spectra presented as canonical spectra representative of the sleep state. Alternatively, an epoch having a weighted power closest to the average weighted power of one or more epochs having similar sleep state designations can be selected and its spectra presented as canonical spectra representative of the sleep state. For example, FIGS. 22, 23, 24, 25, and 26 are screen shots of exemplary visualizations of epochs for various sleep states in a subject (e.g., screen shot 2200 is SWS, screen shot 2300 is REM sleep, screen shot 2400 is Intermediate sleep, screen shot 2500 is awake, and screen shot 2600 is transient) based on EEG spectrogram data analysis.

Figure 27:
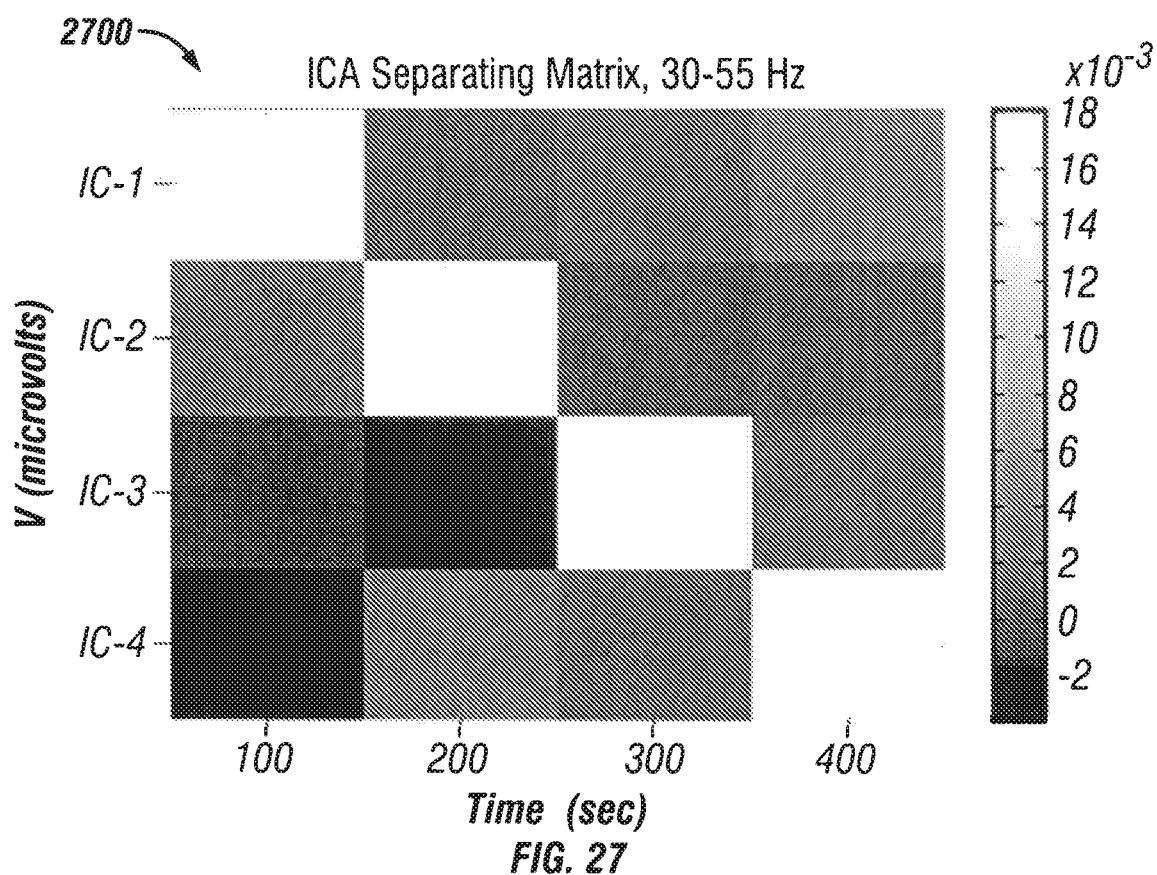
FIG. 27 is a screen shot of an exemplary visualization of the degree of sleep stager separation that distinguishes representative canonical spectra of distinct sleep state.
Figure 28:
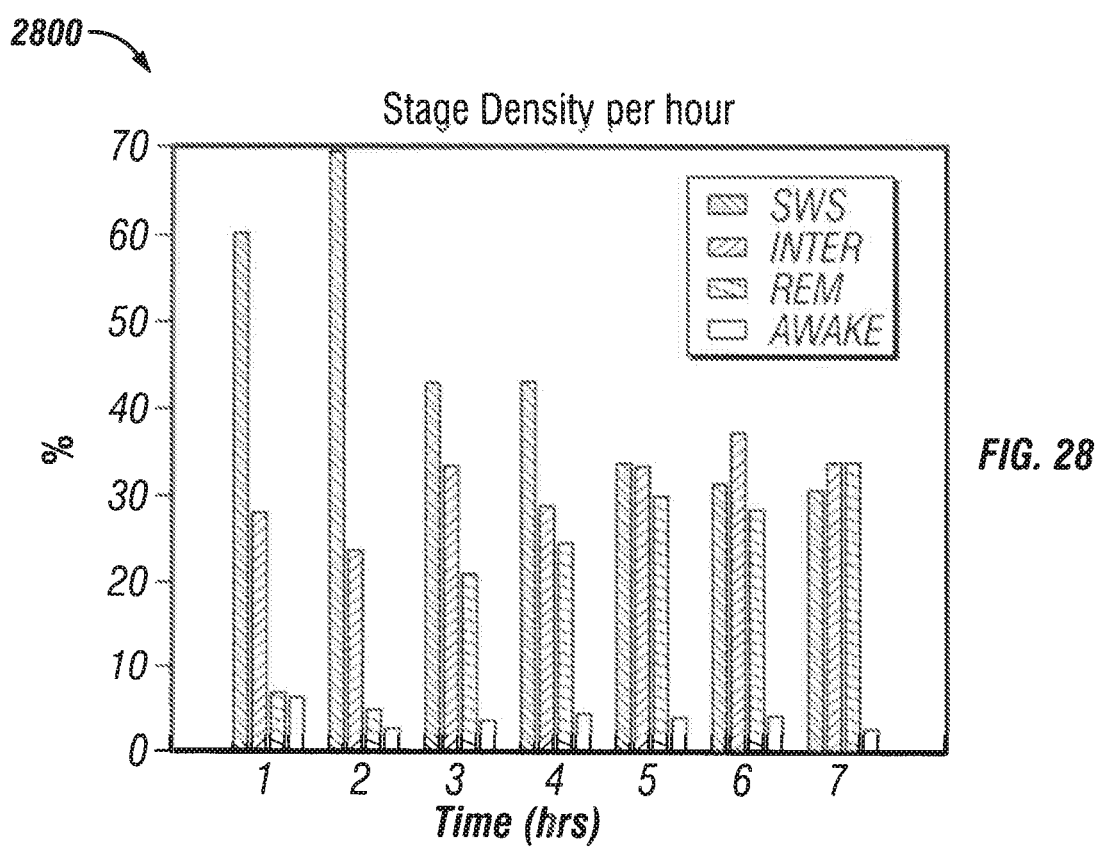
FIGS. 28, 29, 30, 31 and 32 are screen shots of exemplary visualization of sleep state statistics for a subject according to sleep state designations of one or more epochs.

Additionally, sleep state designations can be presented as a function of success versus manual scoring and quality measures can be presented (e.g., sleep state designation separation statistics including single variable and multivariable one-way ANOVAs, regression coefficients calculated for each stage for sleep densities, number of episodes, average episode length, cycle time, and the like). An exemplary visualization of presenting quality measures is shown in FIG. 27. A screen shot 2700 depicts an exemplary visualization of the degree of sleep stage separation that distinguishes representative canonical spectra of distinct sleep states. For example, independent component analysis (ICA) can be used to establish the quality of sleep stage separation in the presented sleep states by applying ICA to canonical spectra or average spectra for each sleep state presented. Any variety of classifying techniques can be used to determine the quality of initially sleep stage classification.

Figure 8:
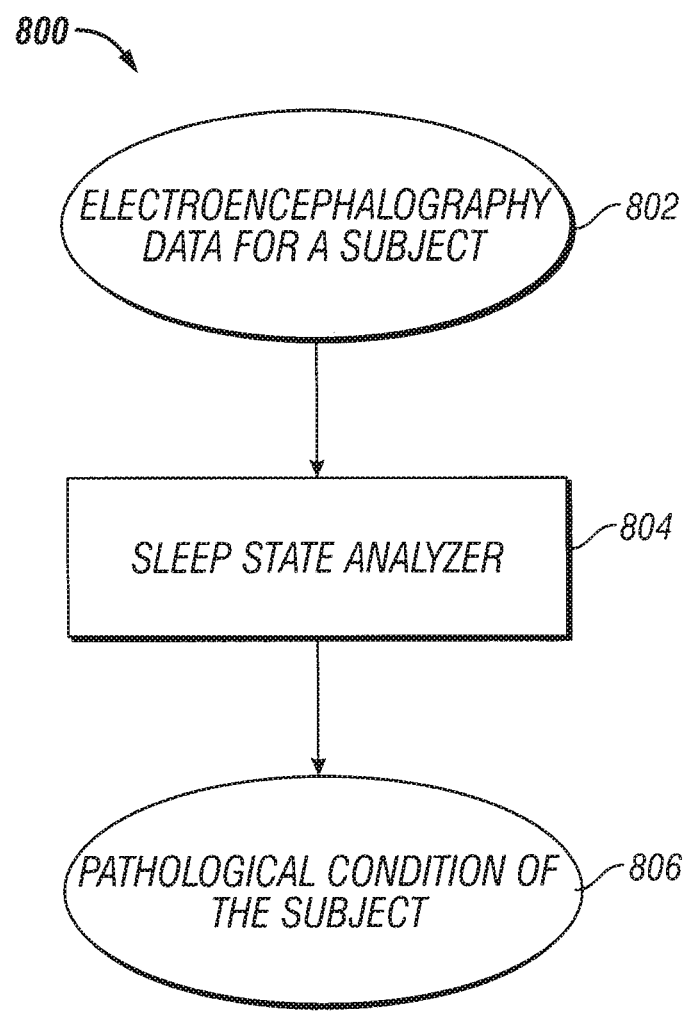
FIG. 8 is a block diagram of an exemplary system for determining a pathological condition of a subject from sleep states.

Example 12—Exemplary System for Determining a Pathological Condition of a Subject from Sleep States FIG. 8 shows an exemplary system 800 for determining a pathological condition of a subject from sleep states.

Electroencephalography data for a subject 802 is obtained and input into sleep state analyzer 804 to determine a pathological condition of the subject 806.

Methods for determining a pathological condition of a subject from sleep states exhibited by a subject, as determined from analyzing electroencephalography data, are described in detail below.

Figure 9:
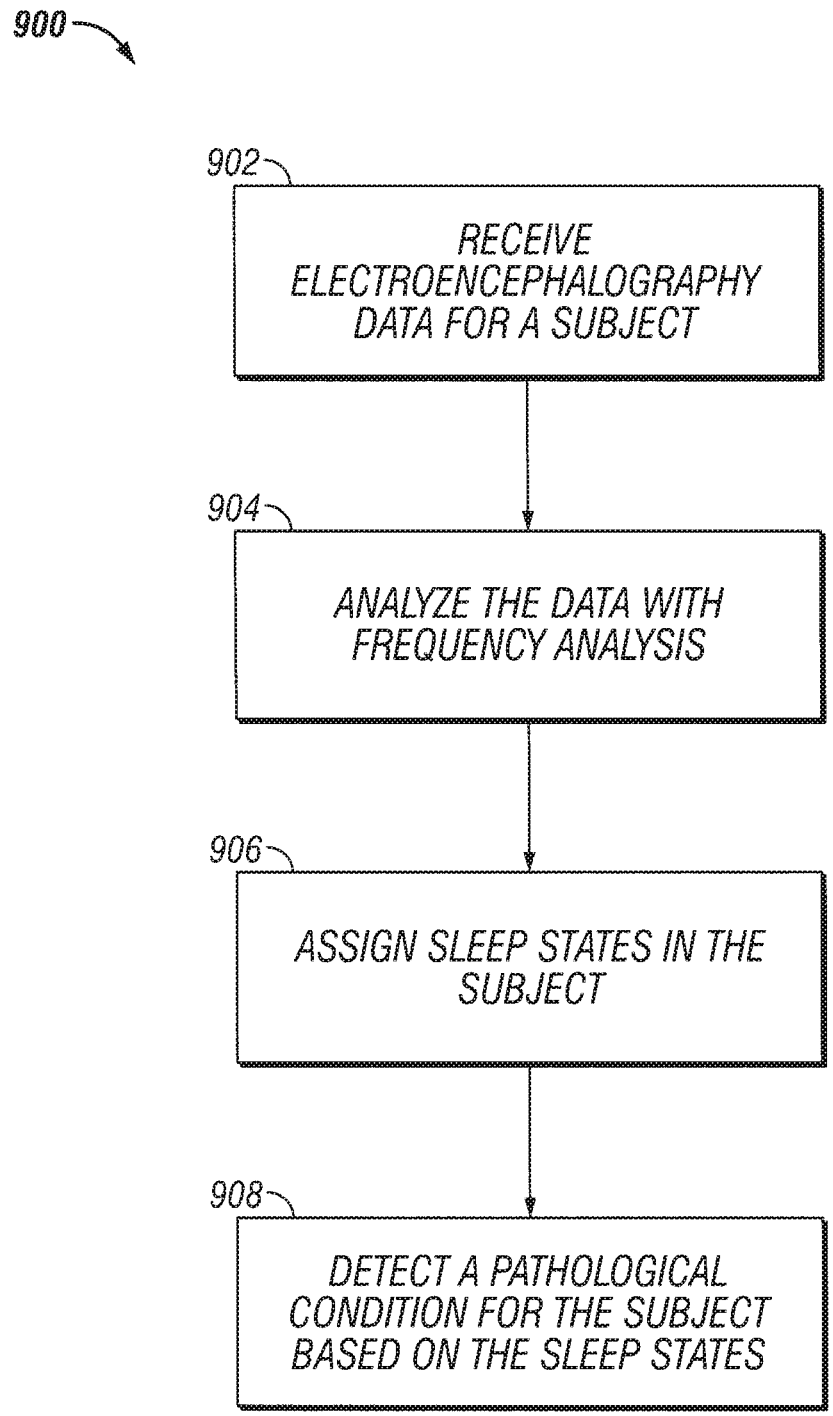
FIG. 9 is a flowchart showing an exemplary computer-implemented method for determining a pathological condition for a subject based on sleep states.

Example 13—Exemplary Computer-Implemented Method for Determining a Pathological Condition for a Subject from Sleep States FIG. 9 shows an exemplary computer-implemented method 900 for determining a pathological condition for a subject from sleep states. The computer-implemented method 900 can be utilized in system 800 of FIG. 8.

At 902, electroencephalography data for a subject is received. For example, electroencephalography data which exhibits lower dynamic range for power in at least one low power first frequency range in a frequency spectrum as compared to a second frequency range in the frequency spectrum can be received.

At 904, the electroencephalography data is analyzed with frequency analysis. For example, frequency analysis can be the adjusting 204 of method 200.

At 906, sleep states in the subject are assigned based on the frequency analysis. For example, method 700 for classifying sleep states of FIG. 7 can be used to assign sleep states in the subject.

At 908, a pathological condition can be detected in a subject based on the sleep states. For example, sleep states can be acquired for an individual and analyzed to determine whether the sleep states represent normal sleep or abnormal sleep. Abnormal sleep could indicate a pathological condition. For example, sleep states can be acquired from individuals with pathological conditions and analyzed for common attributes to generate an exemplary distinctive "pathological condition" sleep state profile and/or sleep state statistics representative of having the pathological condition. Such a profile or statistics can be compared to sleep states determined for a subject in order to detect whether the subject has the pathological condition or any early indicators of the pathological condition. Any variety of pathological conditions can be detected and/or analyzed. For example, sleep related pathological conditions can include epilepsy, Alzheimer's disease, depression, brain trauma, insomnia, restless leg syndrome, and sleep apnea. For example, polysomnographically, subjects with Alzheimer's can show decreased rapid eye movement sleep in proportion to the extent of their dementia.

Figure 10:
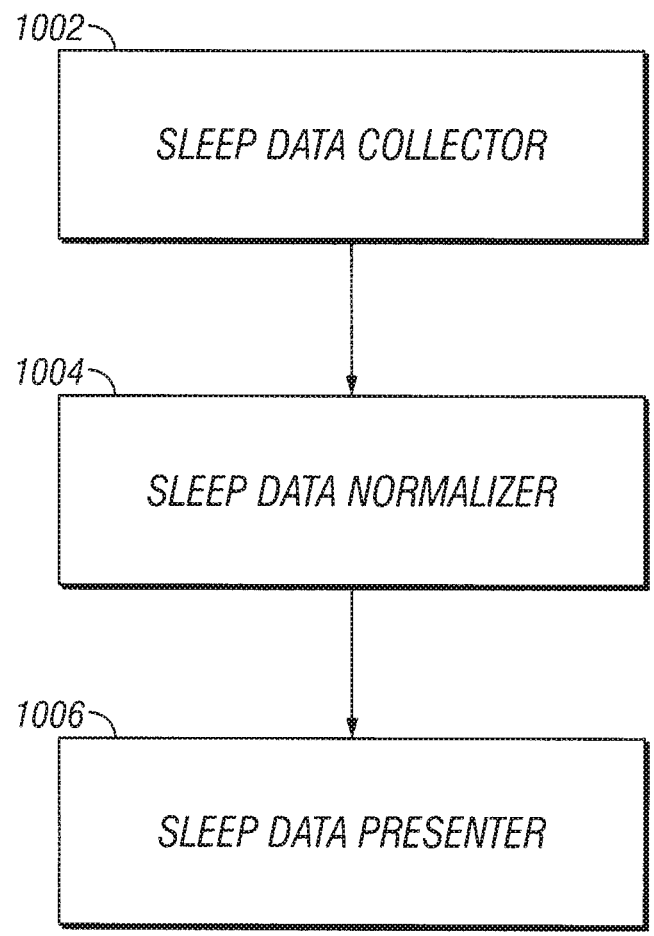
FIG. 10 is a block diagram of an exemplary system for dynamically determining customized sleep scores for a subject.

Example 14—Exemplary System for Dynamically Determining Customized Sleep Scores for a Subject FIG. 10 shows an exemplary system for dynamically determining customized sleep scores for a subject.

A data collector 1002 can obtain electroencephalography data for a subject from a period of sleep.

A data normalizer 1004 can assess the electroencephalography data to determine low power frequency information.

A data presenter 1006 can present sleep states for the subject based at least on the low power frequency information.

Methods for dynamically determining customized sleep scores for a subject are described herein, including method 500 of FIG. 5, method 600 of FIG. 6, and method 700 of FIG. 7.

Example 15—Exemplary Pathological Conditions

In any of the technologies described herein, a variety of pathological conditions can be determined from source data obtained for a subject. For example, depression, brain trauma, epilepsy, and Alzheimer's disease can be pathological conditions determined from sleep states determined from source data obtained for a subject. For example, FIG. 3 9 is a screenshot 3900 of an application of the technologies described herein to determine sleep states indicative of characterizations of Alzheimer's disease from a whole night EEG from a human subject with Alzheimer's.

Example 16—Exemplary Medications and Chemicals that can Affect Sleep

In any of the technologies described herein, the effect of medications and chemicals on sleep states of a subject can be determined via analyzing source data obtained for a subject. For example, sleep states can be modified by alcohol, nicotine, and cocaine use. Exemplary medications that affect sleep include steroids, theophylline, decongestants, benzodiazepines, antidepressants, monoamine oxidase inhibitors (e.g., Phenelzine and Moclobemide), selective serotonin reuptake inhibitors, e.g., Fluoxetine (distributed under the Prozac® name) and Sertralie (distributed under the Zoloft® name), thyroxine, oral contraceptive pills, antihypertensives, antihistamines, neuroleptics, amphetamines, barbiturates, anesthetics, and the like.

Example 17—Exemplary Sleep Statistics

In any of the technologies described herein, any variety of statistics can be generated from adjusted source data. For example, sleep statistics can be generated from adjusted source EEG data that has been classified into sleep states. Exemplary sleep statistics can include information including sleep stage densities, number of sleep stage episodes, sleep stage average duration, cycle time, interval time between sleep stages, sleep stage separation statistics, onset of sleep, rapid eye movement sleep latency, regression coefficients of trends, measures of statistical significance of trends, and the like.

Example 18—Exemplary Implementation of a Method of Determining Sleep States in a Subject Over a Period of Time Sleep is common and may be ubiquitous in all major taxa of the animal kingdom, but it is poorly understood. There is growing evidence from human studies from a variety of low-level psychophysical perceptual and motor tasks that sleep helps to remediate performance loss that is otherwise observed following task learning (Kami et al. 1994; Mednick et al. 2002; Mednick et at. 2003; Fenn et al. 2003). Animal studies have provided evidence of 'replay' during sleep, which may be a central component of the sleep process involved in consolidation of performance.

Recently, it has been shown that during sleep, robustus archistriatalis (RA) neurons of the zebra finch, *Taeniopygia guttata*, song system rehearse song patterns spontaneously and respond to playback of the bird's own song (Dave & Margoliash, 2000). During song development in zebra finches, juvenile birds start changing singing patterns the day following exposure to new vocal material from tutors (Tchernichovski et al. 2001). There is no conclusive evidence though that song learning in juveniles or song maintenance in adult birds requires or benefits from sleep.

Investigation of the possible role of sleep in song learning or maintenance is hampered by the limited knowledge of sleep states in passerine birds. Previous studies have not reported different phases of sleep in the zebra finch (Nick & Konishi, 2002; Hahnloser et al., 2002). In contrast, studies in other birds, including passerine birds (Ayala-Guerrero et al., 1988; Szymczak et al., 1993; Rattenborg et al., 2004), have reported REM sleep in this phylum. Moreover, in rat hippocampus different patterns of neuronal replay are known to take place during different phases of sleep (Buzsaki, 1989; Wilson & McNaughton, 1994; Louie & Wilson, 2001). Therefore, staging of sleep in zebra finches was investigated.

In order to determine the type, arrangement and location of electrodes, a series of acute experiments with birds anesthetized with urethane (20%, circa 90 1.11 over 1 hr) was first conducted. Optimal EEG recordings, as judged by amplitude and reliability of signals, were obtained using differentially paired thick platinum electrodes (A-M systems, WA) touching the dura mater, with an additional ground over the cerebellum. The stereotaxic coordinates for the recording and ground electrodes were respectively: (1.5 R, 3 L), (3 R, 2 L) and (0.5 C, OL).

Five birds were then anesthetized and implanted with 3 mm long L-shaped platinum electrodes at the aforementioned locations with the last 2 mm of the electrodes tangential to the dura mater along the medial-lateral axis. The electrode impedance was 0.15 Ohms. In order to assess unihemispheric sleep, three birds were implanted with bilateral EEG electrodes. Electrodes were secured at their base with dental acrylic and attached with fine copper wire (A-M systems, WA) to a head connector. Birds were given 3 days to recover from the surgery and to habituate to the recording environment.

During recordings, a light cable was attached linking the bird's head to an overhead mercury commutator (Drangonfly Inc, WV). This setup allowed the bird relative freedom of movement within the cage and is preferable to restraining the animal since restraint-induced stress is known to modify sleep architecture (Altman et al., 1972). During the dark phase of the 16:8 light/dark cycle, electrophysiological recordings with direct observation of sleeping birds were combined. Birds were bathed in infrared (IR) light and monitored with an IR camera (Ikegama, Japan). Strategically placed mirrors facilitated detection of eye, head, and body movements. EEGs were amplified by IK, sampled at 1 kHz and filtered at 1-100 Hz. In one bird, which exhibited low frequency artifacts, the data was filtered at 2-100 Hz. A 60 Hz notch filter was also used to improve the signal-to-noise ratio.

In order to establish high confidence in the data analysis, the data was scored both manually as well as automatically. Manual scoring relied on visual inspection of 3 seconds EEG epochs in parallel with scoring of overt behaviors such as eye, head and body movements. Manual scoring classified each epoch as either REM, NREM (non-REM) or awake, including the artifacts. Automated scoring was restricted to the sleep data. The Sleep Parametric EEG Automated Recognition System (SPEARS) for stage separation and quantification of single channel EEG data was used. EEGs were downsampled to 200 Hz, DC filtered, and analyzed over 3 seconds epochs using a 1 second sliding window to combine high spectral, temporal and statistical resolutions. In order to minimize spectral leakage and to increase statistical resolution in the frequency domain, EEG power spectra were computed over 2 orthogonal tapers following a standard multi-taper estimation technique (Thomson, 1982).

The 1-4 Hz (Delta) and 30-55 Hz (Gamma) frequency bands were selected for the stage classification. Delta and Gamma/Delta were respectively used to separate SWS from NSWS (Non-SWS) and REM from NREM. The separation was done with a k-means clustering algorithm and refined by the inclusion of additional variables: the standard deviation and the absolute values of the time derivative of Delta and of (Gamma/Delta). For each epoch, the time derivative was computed over the preceding and successive epochs, using the Matlab "gradient" function. The initial separation was done over the artifact free sleep data. Thereafter, sleep artifacts were attributed the same score as the first non-artifact epoch immediately following it, unless it was an awake epoch in which case the sleep artifact was given the score of the first preceding artifact free epoch (which could not be an awake epoch for otherwise the artifact would have been labeled as an awake artifact by manual scoring). This convention did not significantly reduce the agreement rate with manual scoring (TABLE 1). It was important to include the sleep artifacts since removing or not scoring them would respectively shrink or puncture sleep episodes and thereby change the calculated density, average number of epochs and length for each stage.

Following initial separation, the score of each epoch was smoothed using a 5 second window in order to minimize the score contamination by brief artifacts which might not have been isolated by manual scoring. Epochs that were scored neither as REM nor as SWS were labeled as intermediate (INTER). Conversely, any epoch that had been labeled as belonging to both REM and SWS was relabeled as an outlier. There were very few outliers in the data (TABLE 1).

The REM, SWS and intermediate epochs can be visualized in a 3-dimensional space (FIGS. 20-21) defined by the principal components of the 5 dimensional space defined by Delta, Gamma/Delta, the standard deviation and the derivatives of Delta and (Gamma/Delta) (FIGS. 16-17). In each bird, a multivariate ANOVA on the 5-dimensional clustering space yielded a P<0.001 for the separation of REM, SWS and the intermediate stage.

Using the MATLAB "silhouette" function, the most representative examples for the SWS, REM, intermediate and awake epochs were automatically generated (FIGS. 22, 23, 24, 25, and 26).

The agreement between manual and automated scoring was calculated by classifying each epoch scored as REM by only the manual or the automated scoring as an error. The general agreement rate was remarkably high given the high temporal resolution of the manual and automated scoring (TABLE 1).

Based on the automated analysis, the stage density (FIG. 28), average episode number (FIG. 30) and duration (FIG. 29), inter REM interval (FIG. 31) and stage transitions (FIG. 32) were computed (TABLE 1). All analyses were conducted in Matlab (MathWorks Inc, MA).

Table 1. Stage Statistics for 5 Nights of Sleep in 5 Birds.

Stage density, average episode duration and number and stage transitions were determined. The percentage of transitions out of each stage towards the intermediate stage and the percentage of transitions out of the intermediate stage towards the other stages are shown. For the bihemispherically implanted birds (Animals 1-3), unihemispheric sleep is reported and the other statistics were computed over the hemisphere with the most reliable data as determined by visual inspection of the EEG and video and the absence of outliers. The coefficient of regression was computed over the stage densities and inter-REM intervals for each hour and reflect the circadian distribution of SWS and REM ($*=[r^2>0.5$ and $p<0.05]$, $\S =[r^2>0.5$ and $p=0.05]$), £ for values calculated for hours 2-8, 6 for values calculated for hours 1-7). The agreement rate between automated and manual scoring was determined with and without artifact rejection.

| TAWXI | Animal 1 | Animd 2 | AniiwS3 | Animjl4 | Animt)J |
|---|---|---|---|---|---|
| Sngt OtoiSQr(%) | | | | | |
| SWS | 44.44 | 30.14 | 41.03 | 25.71 | 36.59 |
| INTER | 30% | 30J4 | 37v46 | 31.70 | 37.49 |
| REM | J1.06 | 30.51 | 1179 | 30.77 | 15.12 |
| AWAKE | 3-54 | 8.94 | 5.73 | 11.83 | 10.80 |
| UN IX EM | o.» | 0.S9 | 0.6$ | N/A | N/A |
| OUT1JER | 0.00 | 0.08 | 0.00 | 0.00 | 0.00 |
| A»injitEpliodtDunitom (»*) | | | | | |
| SWS | 14.11 | 1254 | 10.84 | 10.90 | 9.VI |
| INTER | 5.95 | 6.03 | 6.67 | 8.07 | 6A2 |
| REM | 9.84 | 10.11 | 8.53 | 16.98 | 9ai |
| AWAKB | 11.37 | 1210 | 9.30 | 16.11 | 1202 |
| UNHEM | 3JB | 3.84 | 3.59 | WA | WA |
| OUTUER | N/A | | WA | N/A | WA |
| Number of KjUodo | | | | | |
| SWS | MS | 704 | 1092 | 629 | 1073 |
| INTER | 1378 | 1482 | 1623 | 1137 | 1601 |
| REM | m | 653 | 541 | 572 | 557 |
| AWAKE | 85 | 113 | 159 | 65 | 100 |
| UN1HEM | 8 | 44 | 59 | N/A | N/A |
| CJUTUER | 0 | 9 | 0 | 0 | 0 |
| Tsrfultlosi | | | | | |
| SWS-INTER SWS | 97.57 | 8854 | 95.21 | 9393 | 9i m |
| REMHNTER REM | 8549 | 9034 | 86.06 | 92.64 | 83.75 |
| AWAKE-INTER AWAKE | 60.49 | 71.94 | 72.15 | 27.79 | 64.16 |
| OUT-INTERC %OUT | WA | 25.00 | N/A | WA | WA |
| INTER-SWSINTER) | 56.57 | 43.06 | 63.23 | 51.31 | 6M9 |
| INTERREM04INTER) | 38.55 | 49 J 3 | 29.52 | 43.T2 | 26.78 |
| [NTERAWAKJE(% INTER) | 4.$8 | 7*1 | 7.25 | 4.97 | 6.73 |
| INTER-OUT(%INTER) | NM | OJOO | N/A | N/A | WA |
| Reifrarion toffTitStivti | | | | | |
| Step; Density per boutf | | | | | |
| SWS | −6.20 | −1.11 | 0.10 | −5.46 | −2.94 |
| INTER | 1.57 | 1.93 | | 4.21 | 4J09 |
| REM | 459 | 3.16 | 2.44 | 8.03 | 4.77 |
| AWAKE | -0-25 | •3.99 | .205 | •6JS) | -5-92 |
| OUTER | N/A | 0.01 | N/A | WA | N/A |
| Avmge Episode Dtwalko per hour | | | | | |
| SWS | −1.44 | -0-37 | 039 | −6.08 | −1.11 |
| INTER | 0.05 | 0.24 | oai | U7 | 0.31 |
| REM | 0-90 | 0L80 | t06 | 277 | 043 |
| AWAKE | −0.74 | −0.89 | −0.2t | −6M | −0.92 |
| OUTER | N/A | N/A | WA | N/A | N/A |
| Number of Episodes pa hour | | | | | |
| SWS | −3.93 | −1.07 | −6.13 | −3ˆ61 | 042 |
| INTER | 8.00 | 5.29 | −8.11 | 293 | 14/46 |
| REM | 13.8 | 5.68 | 2.01 | 6.93 | 16.21 |
| AWAKE | 2 | −1.54 | −6.05 | 0.18 | −1.61 |
| OUTUER | −0.19 WA | | WA | N/A | N/A |
| Fotef-REM-tntovtl per hour | −7.56 | −266 | −721 | −0.75 | −15.10 |
| Cycle Time p«hour | 10.45 | 2IJ0 | 4.88 | 93.J1 | us |
| Anrtemem Rale (%) | 89.94 | 76.75 | 90.52 | 73.23 | BM4 |
| AatttmaA Pjfbt - No anificts (%) | 90.08 | 76.93 | 91.52 | 73.91 | 88.28 |

Figure 24:
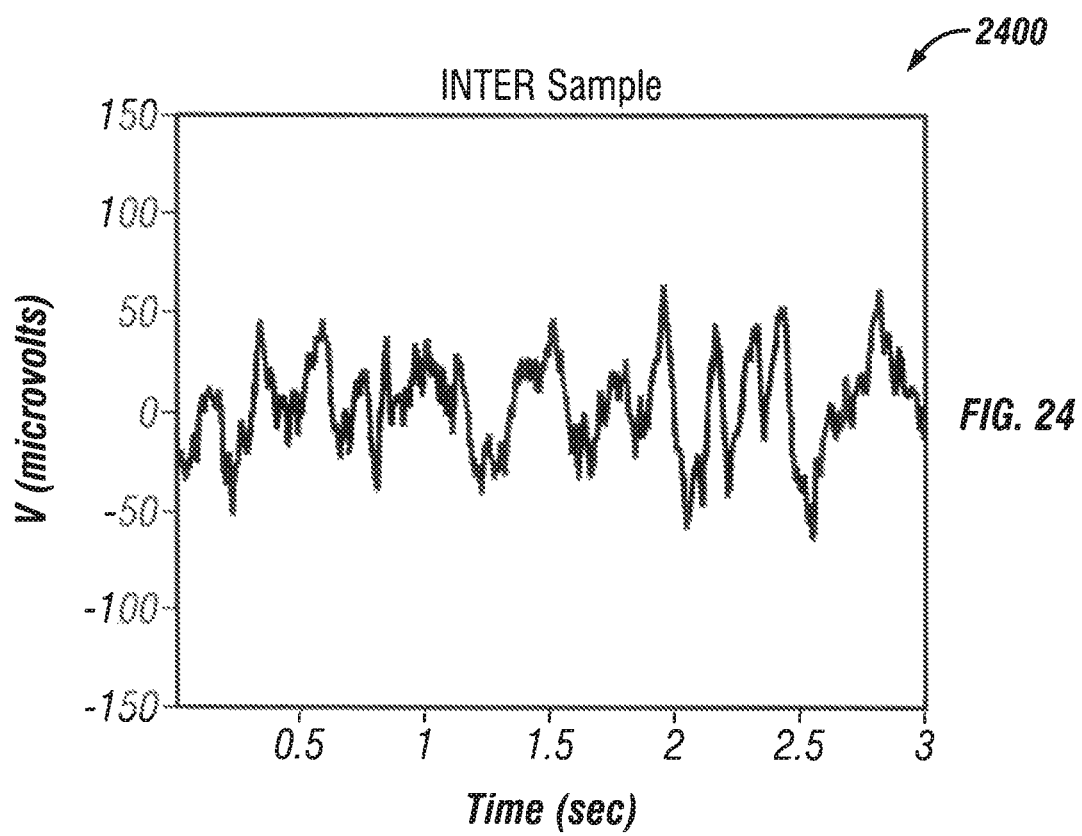
Figure 25:
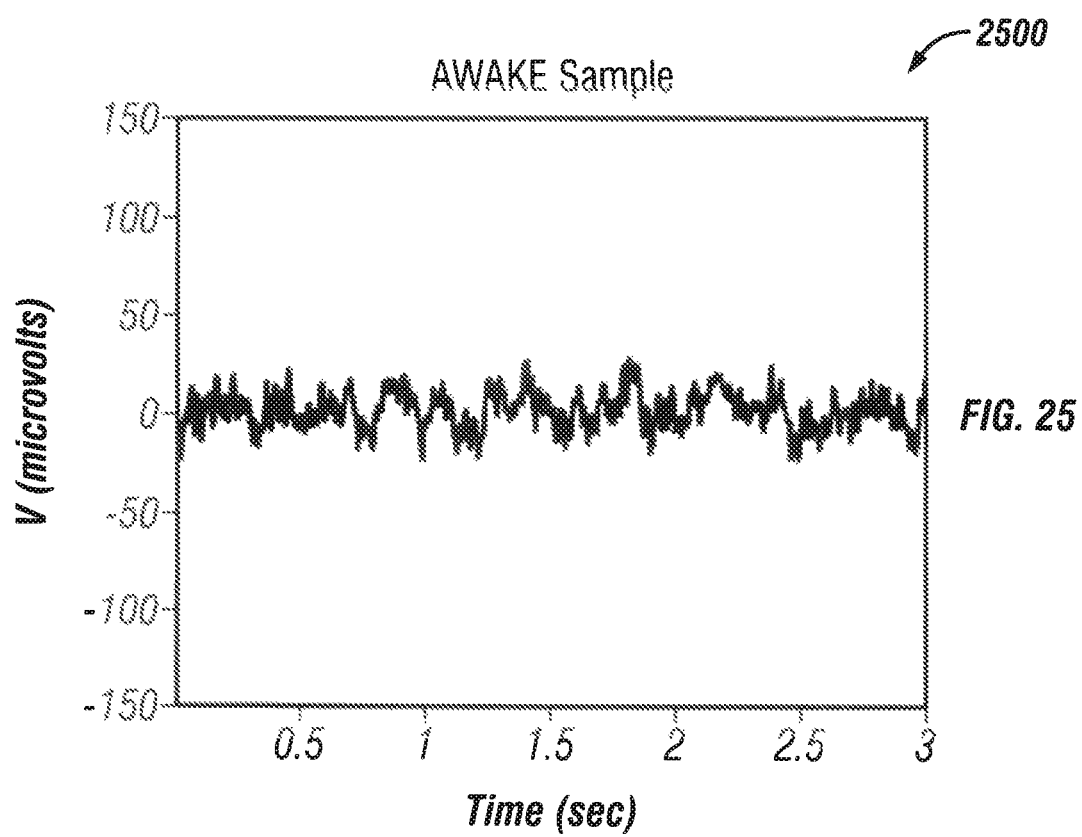

The analysis of the recordings indicate that zebra finches exhibit at least three distinct phases of sleep: SWS, REM and intermediate sleep. SWS had a high amplitude EEG signal with significant power in the Delta range (FIGS. 14-17). REM was characterized by a very low amplitude "awake-like" EEG signal (FIG. 23), typically about ±30 µV with higher power in Gamma (FIGS. 14 and 15) than NREM, a feature that up to now had only been detected in mammals (Maloney et al., 1997; Cantero et al., 2004). The intermediate epochs had highly variable amplitudes, centered around ±50 uV and did not have significant power in either the Delta or Gamma ranges (FIGS. 14, 15 and 24). The intermediate stage has previously only been observed in mammals (Gottesmann et al., 1984; Glin et al., 1991; Kirov & Moyanova, 2002). Both birds on normal circadian patterns and shifted circadian schedules displayed these three sleep stages.

SWS epochs were longer than REM and intermediate episodes early in the night and would, following a mammalian like distribution, decrease in duration (FIG. 29) throughout the night, leading to an overall decrease in stage density (FIG. 28) (TABLE 1).

During NREM birds breathe slowly and regularly; eye and head movements do not follow a stereotypical pattern and are quite distinct from those in REM. We observed several instances when one eye was open and the other was closed. The hemisphere contralateral to the open eye displayed a low amplitude and high frequency EEG while the hemisphere contralateral to the closed eye displayed SWS oscillations. These instances of unihemispheric sleep would usually account for less than 5% of the dark cycle (TABLE 1) and were more frequent in the light cycle. Such patterns of unihemispheric sleep have been previously detected in other species of birds, cetaceans and other marine mammals (Mukhametov et al., 1984; Mukhametov, 1987; Szymczak et al., 1996; Rattenborg et al., 1999; Lyamin et al., 2002).

REM episodes were typically brief early in the night and would become longer throughout the night (FIG. 29) as the number of episodes would increase as well (FIG. 30), leading the Inter-REM intervals to exhibit a downward "mammalian-like" trend throughout the night (FIG. 31) (TABLE 1). REM occurred reliably in conjunction with eye and subtle twitching head movements, as seen in other species (Siegel et al., 1999). The eye movements were on the order of one saccade per second. The head movements were not as reliable, but tended to follow the directional movement of the eyes when present. Head movements were not the result of displacement of the head by the weight of the attached cable during REM neck muscle atonia because the head movements were observed in conjunction with eye movements in intact, un-tethered animals.

The intermediate epochs were brief and numerous. The intermediate state was usually more stable throughout the night, in term of density (FIG. 28), average epoch duration (FIG. 29) and average number of episodes per hour (FIG. 30) than REM and SWS. As is the case in mammals, the intermediate stage consistently acted as—but was not limited to—a transition phase between SWS and REM (FIG. 32) (TABLE 1).

Figure 26:
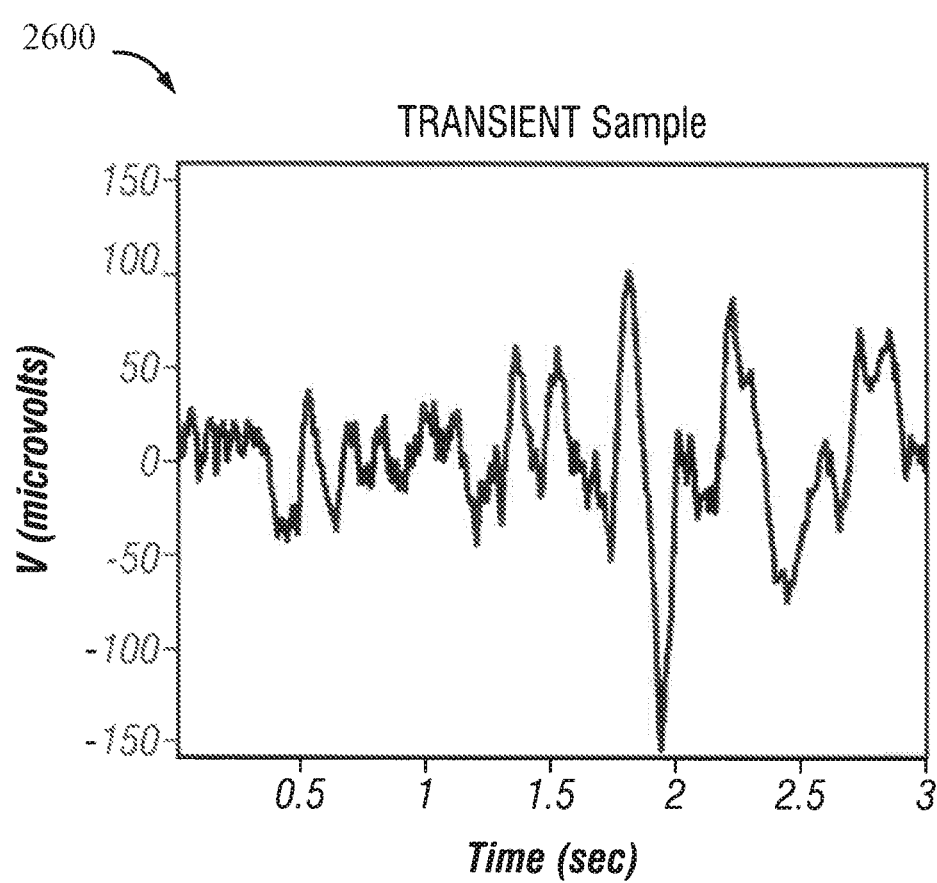
FIG. 26 is a screen shot of a canonical spectra representative of a frequency weighted epoch that displays a transient sleep state having characteristics of more than one sleep state.

In all birds, large peak-to-peak EEG transients lasting approximately 500 milliseconds were detected in NREM (FIG. 26). These signals are reminiscent of the description of mammalian K-complexes (Rowan & Tolunsky, 2003). K-complexes have likely never been previously observed in a non-mammalian species.

In previous studies of zebra finch sleep EEG, only SWS has been reported. In addition to finding a suitable location over which to implant EEG electrodes, this study was successful in detecting NSWS (REM and the intermediate stage) presumably because the nature of the chronic recording setup did not restrain the animals and obviated the need of pharmacological agents such as melatonin to induce sleep. In one study (Mintz et al., 1998), infusion of melatonin was shown to induce SWS in pigeons. It is possible that melatonin might have a similar effect in zebra finches, thus reducing the amount of observable NSWS at night (Hahnloser et al. 2002).

The data analysis technique enabled resolving changes in power at the lower power, high frequencies, which was a key differentiating factor for REM sleep detection. Moreover, the automated analysis restricted manual scoring to the awake state and artifacts, which are easily detectable to a human scorer. Additionally, automated EEG scoring relied on whole night statistics (Gervasoni et al.) rather than on arbitrarily defined threshold, maximum likelihood methods or supervised nonlinear classifiers all of which tend to reflect and impose a human bias on the data analysis.

The results imply that mammalian-like sleep features have evolved in parallel in both mammals and birds. The basic pattern of interdigitation between Delta and Gamma power activation described herein (FIGS. 14 and 15) is highly similar to the one observed in the mammalian cortex during sleep (Destexhe, Contreras & Steriade, 1999). Furthermore, some of the signals we have observed have been specifically attributed to the mammalian cortex (Amzica & Steriade, 1998). Birds are however devoid of a large laminar cortex, raising the possibility that the cortex might be at best sufficient but not necessary for the development of mammalian-like sleep features. Conversely, it is conceivable that birds do indeed possess a mammalian cortex homolog in a non-laminar form (Karten, 1997). Future work at the cellular and molecular levels will be needed to assess which of these highly intriguing possibilities proves to be correct.

References Cited:

Altman et al. Psychon. Sci. 26 (1972), pp. 152-154. Amzica & Steriade. Neuroscience. 1998 February; 82(3):671-86. Ayala-Guerrero et al. Physiol Behay. 1988; 43 (5): 585-9. Buzsaki. Neuroscience. 1989; 31 (3): 551-70.

Cantero et al. Neuroimage. 2004 July; 22(3):1271-80.

Dave & Margoliash. Science. 2000 Oct. 27; 290 (5492): 812-6. Destexhe, Contreras & Steriade. 1999 Jun. 1; 19 (11): 4595-608. Fenn et al. Nature. 2003 ° Oct. 9; 425 (6958): 614-6. Gervasoni et al. J Neurosci. 2004 Dec. 8; 24 (49) : 11137-47. Glin et al. Physiol Behay. 1991 November; 50(5): 951-3. Gottesmann et al. J Physiol (Paris). 1984; 79 (5): 365-72.

Hahnloser et al. Nature. 2002 Sep. 5; 419 (6902): 65-70. Kami et al. Science. 1994 Jul. 29; 265 (5172): 679-682

Karten. Proc Natl Acad Sci USA. 1997 Apr. 1; 94 (7): 2800-4. Khazipov et al. Society for Neuroscience Abstracts 2004. Kirov & Moyanova. Neurosci Lett. 2002 Apr. 5; 322(2): 134-6. Louie & Wilson. Neuron. 2001 January; 29(1): 145-56. Lyamin et al. Behav Brain Res. 2002 Feb. 1; 129(1-2): 125-9 Maloney et al. Neuroscience. 1997 Jan.; 76(2): 541-55. Mednick et al. Nat Neurosci. 2002 July; 5(7): 677-81 Mednick et al. Nat Neurosci. 2003 July; 6(7):697-8. Mintz et al. Neurosci Lett. 1998 Dec. 18; 258(2): 61-4.

Mukhametov et al. Zh Vyssh New Deiat Im I P Pavlova. 1984 March-April; 34(2):259-64.

Mukhametov. Neurosci Lett. 1987 Aug. 18; 79(1-2): 128-32.
Nick & Konishi. Proc Natl Acad Sci USA. 2001 Nov. 20; 98(24):14012-6.
Rattenborg et al. Behav Brain Res. 1999 Nov. 15; 105 (2): 163-72. Rattenborg et al. PLoS Biol. 2004 July; 2(7): E212.
Rowan & Tolusnky. "Primer of EEG". Butterworth Heinemann.
Elsevier Science 2003
Siegel et al. Neuroscience. 1999; 91(1):391-400.
Szymczak et al. Physiol Behay. 1993 June; 53(6):1201-10. Szymczak et al. Physiol Behay. 1996 October; 60 (4): 1115-20. Tchernichovski et al. Science. 2001 Mar. 30; 291 (5513): 2564-9. Thomson, Proceedings of the IEEE, Vol. 70 (1982), pp. 1055-1096. Wilson & McNaughton. Science. 1993 Aug. 20; 261 (5124): 1055-8

Figure 35:
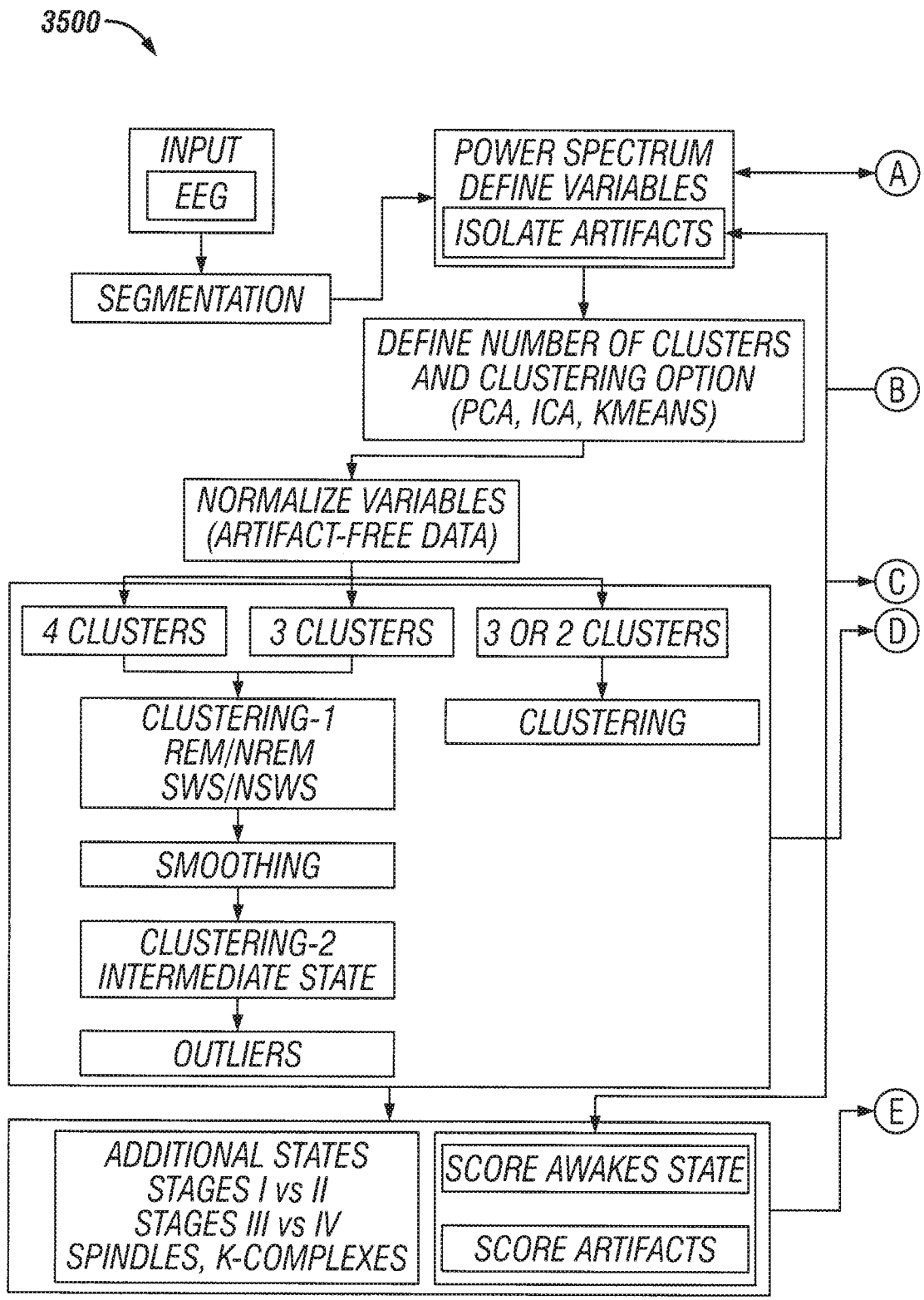
FIG. 35 is a flowchart showing yet another exemplary method for classifying sleep states in a subject that can be implemented with the described technologies.
Figure 35:
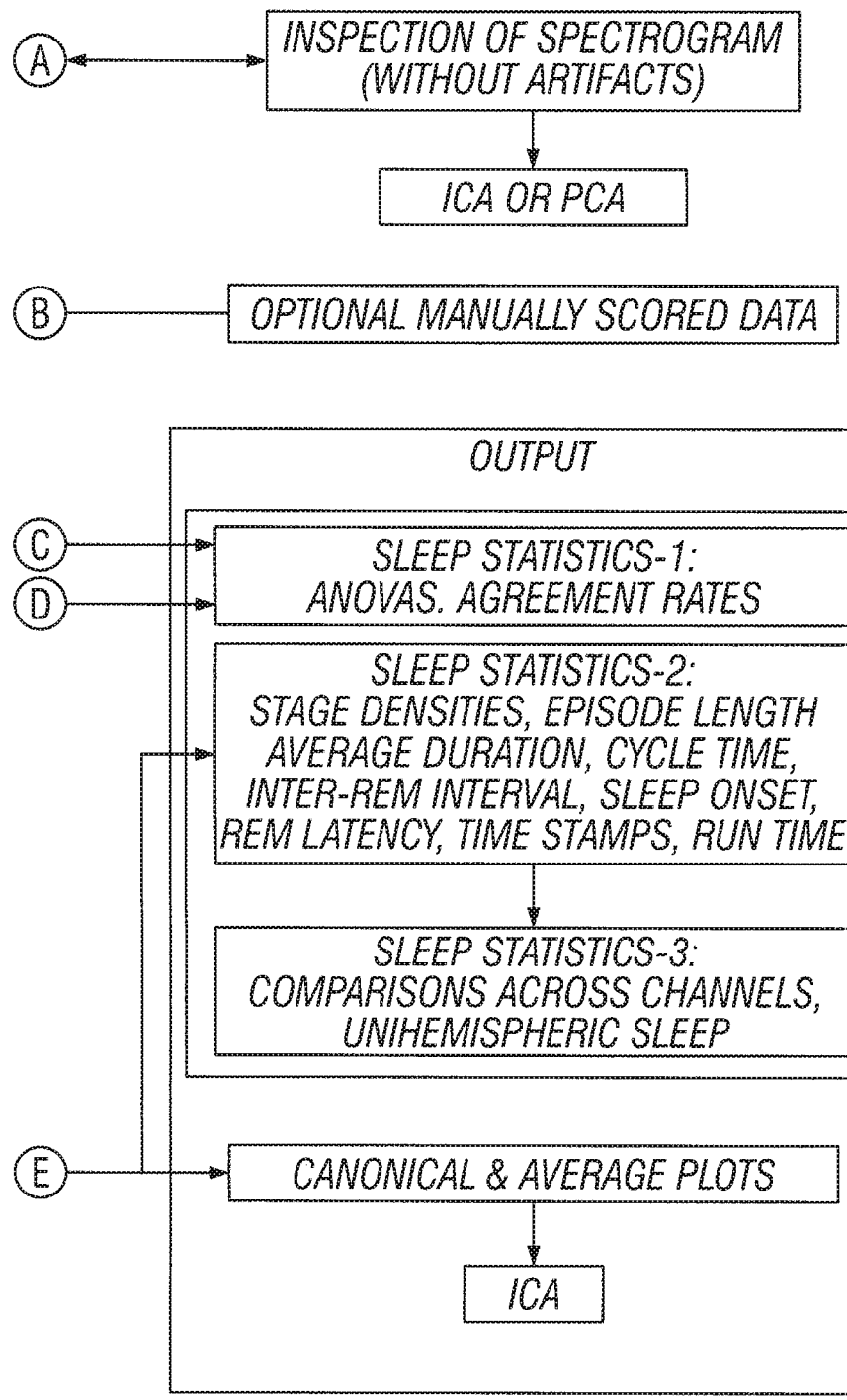

Example 19—Exemplary Method for Determining Sleep States in a Subject Over a Period of Time FIG. 35 shows yet another exemplary method 3500 for determining sleep states in a subject over a period of time. The method 3500 incorporates a wide variety of techniques described herein.

Example 20—Exemplary Transformation Techniques

There are a wide variety of data transformation methods used in signal processing to determine power for a variety of frequencies in time series data. As described herein, transformation methods can include multi-taper transform, Fourier transform, wavelet transform. Any other transformation method for measuring power for a variety of frequencies represented in a plurality of time series or epochs in a source signal can be used.

Example 21—Exemplary Computational Methods for Differentiating Groups of Data There are a wide variety of clustering and classification methods used in computational signal processing to differentiate data into distinct classes. As described herein, the clustering method used is k-means clustering but any computational signal processing method for differentiating groups of data could be used. Similarly, classification methods such as component analysis (e.g., principle and independent component analysis) are used as described herein. An overview of computational methods is provided below.

Clustering (or cluster analysis) is unsupervised learning where the classes are unknown a priori and the goal is to discover these classes from data. For example, the identification of new tumor classes using gene expression profiles is a form of unsupervised learning.

Classification (or class prediction) is a supervised learning method where the classes are predefined and the goal is to understand the basis for the classification from a set of labeled objects and build a predictor for future unlabeled observations. For example, the classification of malignancies into known classes is a form of supervised learning.
Clustering:
Clustering involves several distinct steps:
Defusing a suitable distance between objects;
Selecting and applying a clustering algorithm.
Clustering procedures commonly fall into two categories: hierarchical methods and partitioning methods. Hierarchical methods can be either divisive (top-down) or agglomerative (bottom-up). Hierarchical clustering methods produce a tree or dendrogram. Hierarchical methods provide a hierarchy of clusters, from the smallest, where all objects are in one cluster, through to the largest set, where each observation is in its own cluster Partitioning methods usually require the specification of the number of clusters. Then, a mechanism for apportioning objects to clusters must be determined. These methods partition the data into a prespecified number k of mutually exclusive and exhaustive groups. The method iteratively reallocates the observations to clusters until some criterion is met (e.g. minimize within-cluster sums of-squares). Examples of partitioning methods include k-means clustering, Partitioning around medoids (PAM), self organizing maps (SOM), and model-based clustering.

Most methods used in practice are agglomerative hierarchical methods, in a large part due to the availability of efficient exact algorithms. However both clustering methods have their advantages and disadvantages. Hierarchical advantages include fast computation, at least for agglomerative clustering, and disadvantages include that they are rigid and cannot be corrected later for erroneous decisions made earlier in the method. Partitioning advantages include that such methods can provide clusters that (approximately) satisfy an optimality criterion, and disadvantages include that one needs an initial k and the methods can take long computation time.

In summary, clustering is a more difficult problem than classifying for a variety of reasons including the following:
there is no learning set of labeled observations;
the number of groups is usually unknown;
implicitly, one must have already selected both the relevant features and distance measures used in clustering methods.
Classification:

Techniques involving statistics, machine learning, and psychometrics can be used. Examples of classifiers include logistic regression, discriminant analysis (linear and quadratic), principle component analysis (PCA), nearest neighbor classifiers (k-nearest neighbor), classification and regression trees (CART), prediction analysis for microarrays, neural networks and multinomial log-linear models, support vector machines, aggregated classifiers (bagging, boosting, forests), and evolutionary algorithms.
Logistic Regression:

Logistic regression is a variation of linear regression which is used when the dependent (response) variable is a dichotomous variable (i.e., it takes only two values, which usually represent the occurrence or non-occurrence of some outcome event, usually coded as 0 or 1) and the independent (input) variables are continuous, categorical, or both. For example, in a medical study, the patient survives or dies, or a clinical sample is positive or negative for a certain viral antibody.

Unlike ordinary regression, logistic regression does not directly model a dependent variable as a linear combination of dependent variables, nor does it assume that the dependent variable is normally distributed. Logistic regression instead models a function of the probability of event occurrence as a linear combination of the explanatory variables. For logistic regression, the function relating the probabilities to the explanatory variables in this way is the logistic function, which has a sigmoid or S shape when plotted against the values of the linear combination of the explanatory variables.

Logistic regression is used in classification by fitting the logistic regression model to data and classifying the various explanatory variable patterns based on their fitted probabilities. Classifications of subsequent data are then based on their covariate patterns and estimated probabilities.

Discriminant Analysis:

In summary discriminant analysis represents samples as points in space and then classifies the points. Linear discriminant analysis (LDA) finds an optimal plane surface that best separates points that belong to two classes. Quadratic discriminant analysis (QDA) finds an optimal curved (quadratic) surface instead. Both methods seek to minimize some form of classification error.

Fisher Linear Discriminant Analysis (FLDA or LDA):

LDA finds linear combinations (discriminant variables) of data with large ratios of between-groups to within-groups sums of squares and predicts the class of an observation x by the class whose mean vector is closest to x in terms of the discriminant variables. Advantages of LDA include that it is simple and intuitive where the predicted class of a test case is the class with the closest mean and it is easy to implement with a good performance in practice. Disadvantages of LDA include the following:

linear discriminant boundaries may not be flexible enough;

features may have different distributions, within classes;

in the case of too many features, performance may degrade rapidly due to over parameterization and high variance of parameter estimates.

Nearest Neighbor Classifiers:

Nearest neighbor methods are based on a measure of distance between observations, such as the Euclidean distance or one minus the correlation between two data sets. K-nearest neighbor classifiers work by classifying an observation x as follows:

find the k observations in the learning set that are closest to x;

predict the class of x by majority vote, i.e., choose the class that is most common among these k neighbors. Simple classifiers with k=1 can generally be quite successful. A large number of irrelevant or noise variables with little or no relevance can substantially degrade the performance of a nearest neighbor classifier.

Classification Trees:

Classification trees can be used, for example, to split a sample into two sub-samples according to some rule (feature variable threshold). Each sub-sample can be further split, and so on. Binary tree structured classifiers are constructed by repeated splits of subsets (nodes) into two descendant subsets. Each terminal subset of the tree is assigned a class label and the resulting partition corresponds to the classifier. The three main aspects of tree construction include selection of splits (at each node, the split that maximize the decrease in impurity is chosen), decision to declare a node terminal or to continue splitting (to grow a large tree, the tree is selectively pruned upwards getting a decreasing sequence of subtrees), and assignment of each terminal node to a class (the class the minimizes the resubstitution estimate of the misclassification probability is chosen for each terminal node).

Prediction Analysis for Microarrays:

These methods utilize nearest shrunken centroid methodology. First, a standardized centroid for each class is computed. Then each class centroid is shrunk toward the overall centroid for all classes by the so-called threshold (chosen by the user). Shrinkage consists of moving the centroid towards zero by threshold, setting it equal to zero if it hits zero.

Artificial Neural Networks:

The key element of the artificial neural network (ANN) model is the novel structure of the information processing system. It is composed of many highly interconnected processing elements that are analogous to neurons and are tied together with weighted connections that are analogous to synapses. As with all classification methods, once the ANN is trained on known samples, it will be able to predict samples automatically.

Support Vector Machines:

Support Vector Machines are learning machines that can perform binary classification (pattern recognition) and real valued function approximation (regression estimation) tasks. Support Vector Machines non-linearly map their n-dimensional input space into a higher dimensional feature space. In this high dimensional feature space a linear classifier is constructed.

Aggregating Classifiers:

This method works by aggregating predictors built from perturbed versions of a learning set. In classification, the multiple versions of the predictor are aggregated by voting. Bootstrapping is the simplest form of bagging in which perturbed learning sets of the same size as the original learning set are non-parametric bootstrap replicates of the learning set, i.e., drawn at random with replacement from the learning set. Parametric bootstrapping involves perturbed learning sets that are generated according to a mixture of multivariate Gaussian distributions. Random Foresting is a combination of tree classifiers (or other), where each tree depends on the value of a random vector for all trees in the forest. In boosting, classifiers are constructed on weighted version the training set, which are dependent on previous classification results. Initially, all objects have equal weights, and the first classifier is constructed on this data set. Then, weights are changed according to the performance of the classifier. Erroneously classified objects get larger weights, and the next classifier is boosted on the reweighted training set. In this way, a sequence of training sets and classifiers is obtained, which is then combined by simple majority voting or by weighted majority voting in the decision.

Example 22—Exemplary Sleep Data Presenter

In any of the examples herein, an electronic or paper-based report based on sleep state data can be presented. Such reports can include customized sleep state information, sleep state statistics, pathological conditions, medication and/or chemical effects on sleep, and the like for a subject. Recommendations for screening tests, behavioral changes, and the like can also be presented. Although particular sleep data and low frequency information results are shown in some examples, other sleep data presenters and visualizations of data can be used.

Example 23—Exemplary Sleep State Information for Subjects

Figure 33:
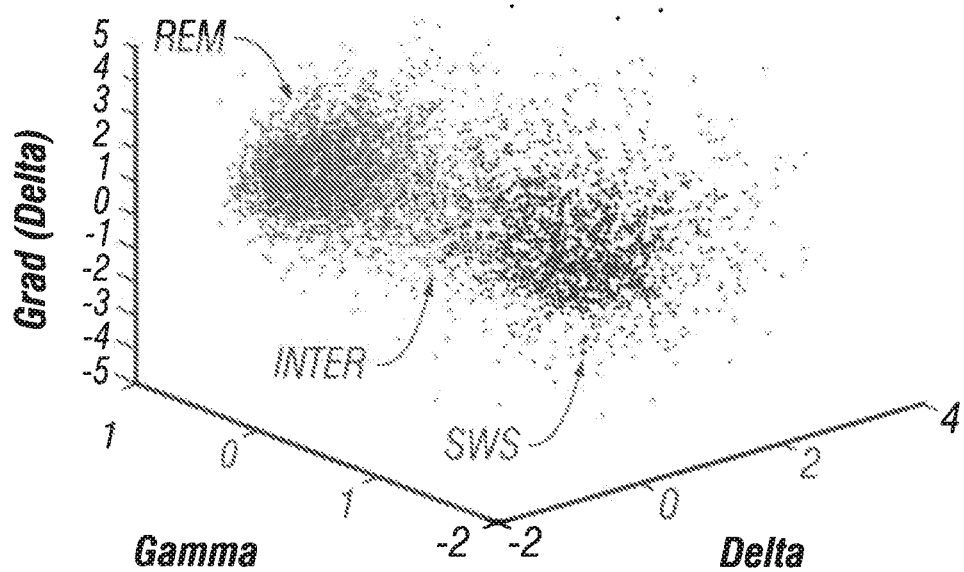
FIG. 33 is a screen shot of an exemplary visualization of classified anesthesia states of an anesthetized cat based on EEG spectrogram data.
Figure 34:
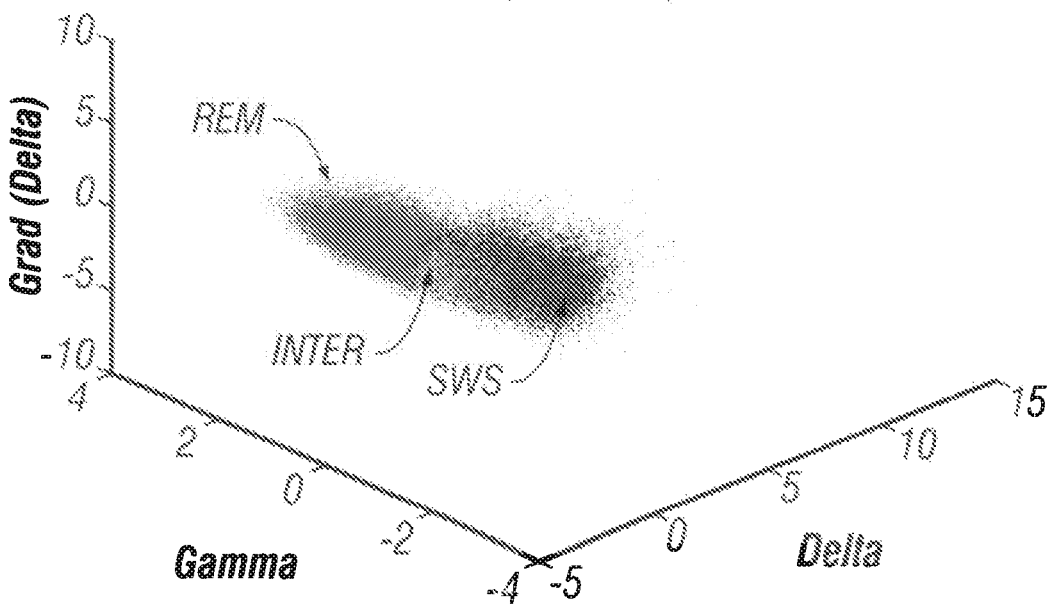
FIG. 34 is a screen shot of an exemplary visualization of classified sleep states of a human subject based on EEG spectrogram data.

Exemplary sleep state information can be obtained from a variety of subjects using any of the technologies described herein. FIG. 33 includes a screenshot 3300 of an exemplary visualization of classified anesthetized states of an anesthetized cat based on analyzed EEG spectrogram data. For example, in screenshot 3300, a SWS classification corresponds to a deep anesthetized state, a REM sleep classification corresponds to a light anesthetized state, and an INTER sleep classification corresponds to an intermediate anesthetized state. In such a manner, the technologies described herein can be utilized to determine anesthetized states in a human or other mammalian subject. FIG. 34 includes a screenshot 3400 of an exemplary visualization of classified sleep states of a human subject based on analyzed EEG spectrogram data.

Example 24—Exemplary Advantages and Applications of Technologies

The speed at which this data analysis can be performed, the customized and unsupervised nature of analysis, and the ability to extract previously disregarded or unanalyzed low power frequency information make this methodology particularly attractive to a variety of fields of study. The technology can be highly adaptable using a variable number of states, a variable number of identification rules, adaptable calibration, variable time resolution, and variable spectral resolution. Adjusting source data to generate adjusted source data can be especially applicable to analyzing animal signal data in testing for pathological conditions and medication and chemical effects. In any of the examples herein, low amplitude but highly variable frequency data can be extracted and analyzed (e.g., discovering temporal patterns in data). Applications can include diverse uses from analyzing stock market data (e.g., analyzing fluctuations in penny stocks to determine common variability otherwise disregarded due to small price changes) to accessing encoded data (e.g., Morse code data stored in low power, very high or very low frequencies within sound waves) to analyzing visual images with several spatial frequencies. Similarly, the technologies described herein can be used to determine customized sleep quality determinations for a subject via sleep state information generated.

Figure 40:
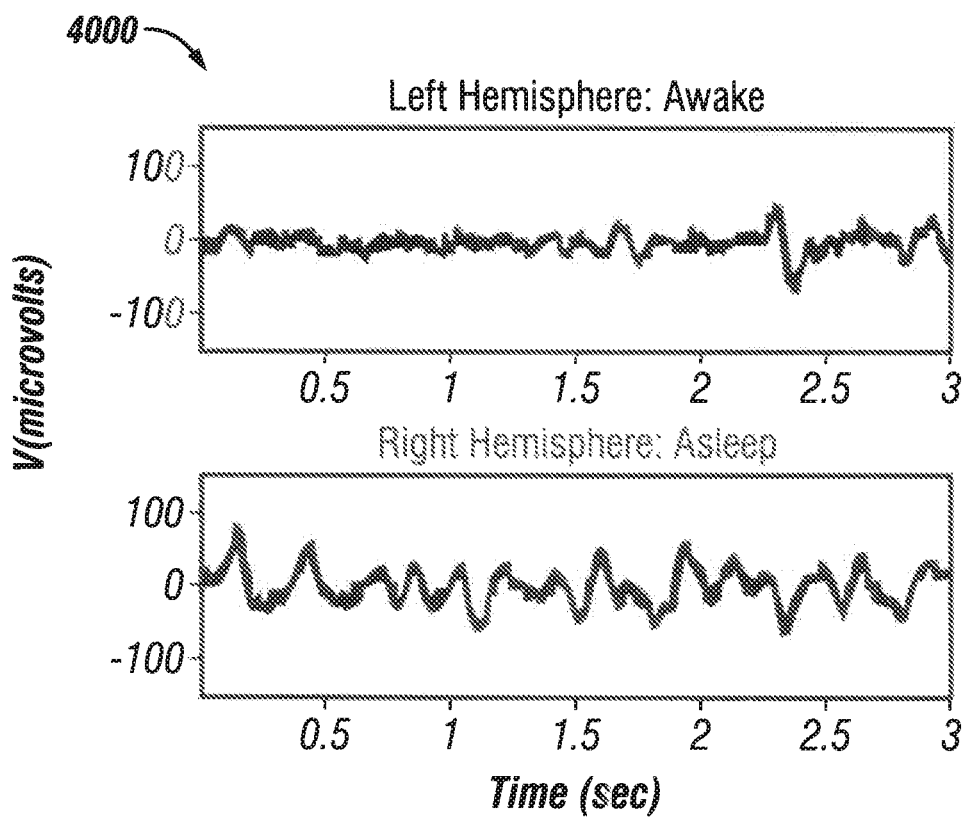
FIG. 40 is a screen shot of an exemplary visualization of classified unihemispheric sleep from a bird.

In any of the examples herein, the methods can be applied to source data received from one channel or multiple channels. The methods can be applied independently to source data from multiple channels with comparison made between the channels. For example, unihemispheric sleep can be determined from independent EEG channel data received from each hemisphere of a brain. FIG. 40 shows a screen shot 4000 of unihemispheric sleep determined from independent EEG channel data received from each hemisphere of a bird's brain. Alternatively, the methods can be simultaneously applied to source data from multiple channels, thereby analyzing combined multiple channel source data. For example, EEG channel data and EMG channel data for a subject can be simultaneously analyzed to determine awake versus REM sleep states whereby a REM designated sleep state from analysis of EEG data can be reassigned as an awake sleep state if the EMG data falls into a high amplitude cluster.

Further, in any of the examples herein, methods such as denoising source separation (dss) and the like can be used in combination with the methods described herein to determine sleep states. For example, dss can use low frequency information to determine REM sleep.

While the techniques described herein can be particularly valuable for analyzing low power frequency information they can also be applied to clustering and determining sleep stages from any variety of signals including signals wherein the high and low frequencies have the same power distributions. Additionally, techniques pertaining to spectrogram analysis, stage classification and confidence, measures can be used independently of one another.

Example 25—Exemplary Visualizations of Data

In any of the techniques described herein, exemplary visualizations of data can utilize colors to depict different aspects of that data. For example, classified data (e.g., sleep state classifications such as REM, SWS, and INTER) can be color coded for each classification state for visualization of the classified data. Alternatively, greyscale can be used to code for each classification state for visualization of the classified data.

Example 26—Exemplary Computer System for Conducting Analysis

Figure 36:
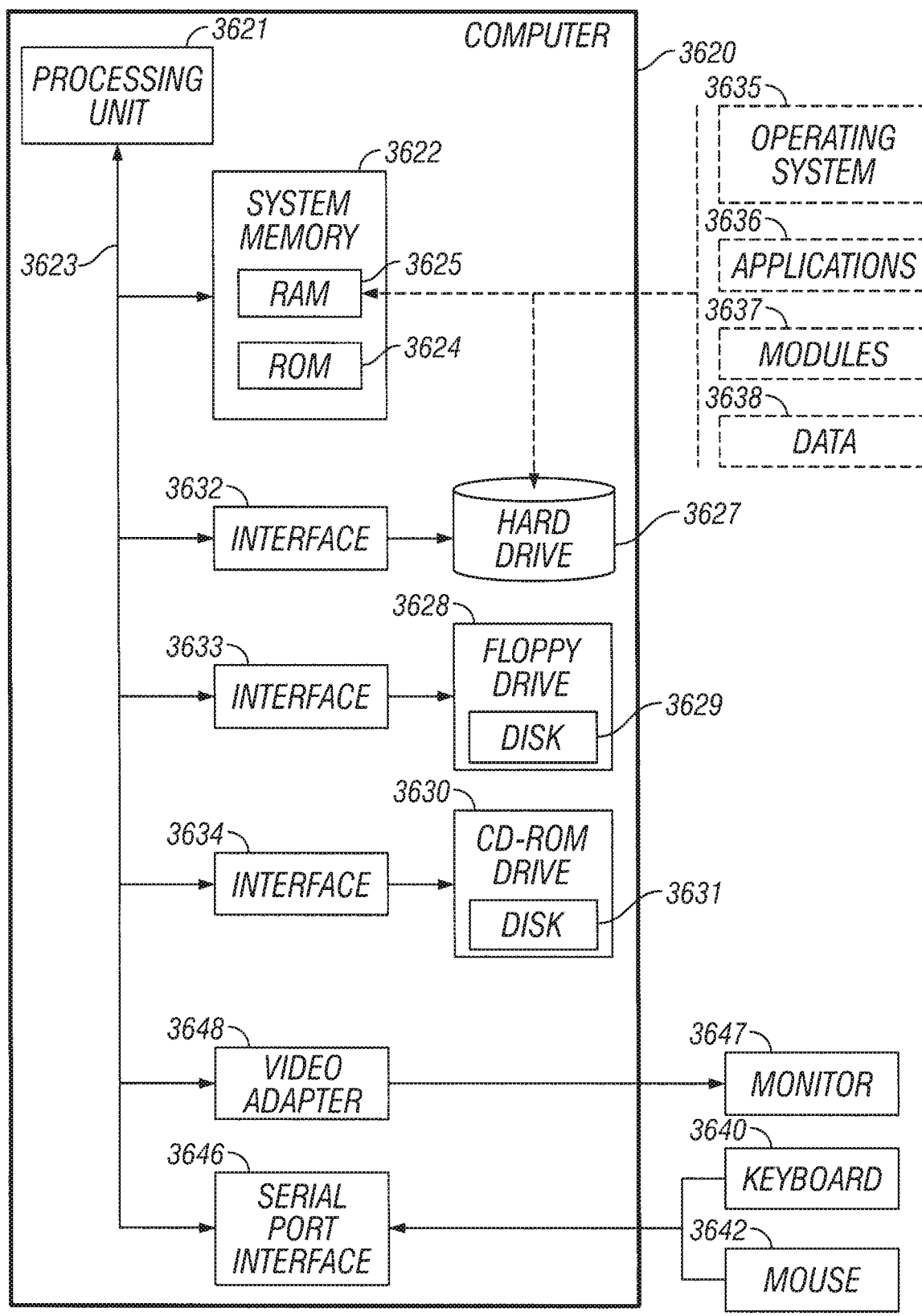
FIG. 36 is an exemplary computer system that can be implemented with the described technologies.

FIG. 36 and the following discussion provide a brief, general description of a suitable computing environment for the software (for example, computer programs) described above. The methods described above can be implemented in computer-executable instructions (for example, organized in program modules). The program-modules can include the routines, programs, objects, components, and data structures that perform the tasks and implement the data types for implementing the techniques described above.

While FIG. 36 shows a typical configuration of a desktop computer, the technologies may be implemented in other computer system configurations, including multiprocessor systems, microprocessor-based or programmable consumer electronics, minicomputers, mainframe computers, and the like. The technologies may also be used in distributed computing environments where tasks are performed in parallel by processing devices to enhance performance. For example, tasks can be performed simultaneously on multiple computers, multiple processors in a single computer, or both. In a distributed computing environment, program modules may be located in both local and remote memory storage devices. For example, code can be stored on a local machine/server for access through the Internet, whereby data from assays can be uploaded and processed by the local machine/server and the results provided for printing and/or downloading.

The computer system shown in FIG. 36 is suitable for implementing the technologies described herein and includes a computer 3620, with a processing unit 3621, a system memory 3622, and a system bus 3623 that interconnects various system components, including the system memory to the processing unit 3621. The system bus may comprise any of several types of bus structures including a memory bus or memory controller, a peripheral bus, and a local bus using a bus architecture. The system memory includes read only memory (ROM) 3624 and random access memory (RAM) 3625. A nonvolatile system (for example, BIOS) can be stored in ROM 3624 and contains the basic routines for transferring information between elements within the personal computer 3620, such as during start-up. The personal computer 3620 can further include a hard disk drive 3627, a magnetic disk drive 3628, for example, to read from or write to a removable disk 3629, and an optical disk drive 3630, for example, for reading a CD-ROM disk 3631 or to read from or write to other optical media. The hard disk drive 3627, magnetic disk drive 3628, and optical disk 3630 are connected to the system bus 3623 by a hard disk drive interface 3632, a magnetic disk drive interface 3633, and an optical drive interface 3634, respectively. The drives and their associated computer-readable media provide nonvolatile storage of data, data structures, computer-executable instructions (including program code such as dynamic link libraries and executable files), and the like for the personal computer 3620. Although the description of computer-readable media above refers to a hard disk, a removable magnetic disk, and a CD, it can also include other types of media that are readable by a computer, such as magnetic cassettes, flash memory cards, DVDs, and the like.

A number of program modules may be stored in the drives and RAM 3625, including an operating system 3635, one or more application programs 3636, other program modules 3637, and program data 3638. A user may enter commands and information into the personal computer 3620 through a keyboard 3640 and pointing device, such as a mouse 3642. Other input devices (not shown) may include a microphone, joystick, game pad, satellite dish, scanner, or the like. These and other input devices are often connected to the processing unit 3621 through a serial port interface 3646 that is coupled to the system bus, but may be connected by other interfaces, such as a parallel port, game port, or a universal serial bus (USB). A monitor 3647 or other type of display device is also connected to the system bus 3623 via an interface, such as a display controller or video adapter 3648. In addition to the monitor, personal computers typically include other peripheral output devices (not shown), such as speakers and printers.

The above computer system is provided merely as an example. The technologies can be implemented in a wide variety of other configurations. Further, a wide variety of approaches for collecting and analyzing source data are possible. For example, the data can be collected and analyzed, and the results presented on different computer systems as appropriate. In addition, various software aspects can be implemented in hardware, and vice versa. Further, paper-based approaches to the technologies are possible, including, for example, purely paper-based approaches that utilize instructions for interpretation of algorithms, as well as partially paper-based approaches that utilize scanning technologies and data analysis software.

Example 27—Exemplary Computer-Implemented Methods

Any of the computer-implemented methods described herein can be performed by software executed by software in an automated system (for example, a computer system). Fully-automatic (for example, without human intervention) or semiautomatic operation (for example, computer processing assisted by human intervention) can be supported. User intervention may be desired in some cases, such as to adjust parameters or consider results.

Such software can be stored on one or more computer-readable media comprising computer-executable instructions for performing the described actions. Such media can be tangible (e.g., physical) media.

Having illustrated and described the principles of the invention in exemplary embodiments, it should be apparent to those skilled in the art that the described examples are illustrative embodiments and can be modified in arrangement and detail without departing from such principles. Techniques from any of the examples can be incorporated into one or more of any of the other examples.

Another embodiment uses a dual normalization for even further dynamic range increase. This embodiment explains, and relies on, data from human sleep subjects, rather than birds as in some of the previous embodiments. Moreover, any of the applications described above for the previous embodiments are equally applicable for this embodiment, as are the techniques of normalization and clustering.

This embodiment uses many of the characteristics of the previous embodiments and also adds some refinements. The embodiment operates to analyze brain wave activities. The signals from a brainwave, e.g., an EEG, typically follow the characteristic where the amount of power in the brain wave is related to, e.g., proportional to 1/f, where f is the frequency of the brain wave: The amount of power is inversely proportional to the frequency. As explained with reference to previous embodiments, this 1/f spectral distribution has tended to obscure the higher frequency portions of the signal, since those higher frequency portions of the signals had smaller voltage amplitudes.

Human observers who observed the waves representing the EEGs have historically been unable to ascertain any substantial information relative to the higher frequency. Many reasons for this have been postulated by the inventors. One reason is that higher frequencies of brainwave activities have been more filtered from the skull, because the physical structure of the skull acts as a low pass filter.

Previous embodiments have shown how normalization, for example using Z scoring, allowed analysis of more information from the brainwave signal. The analysis which was previously carried out normalized power information across frequencies. The normalization preferably used Z scoring, but any other kind of data normalization can be used. The normalization which is used is preferably unitless, like Z scoring. As well known in the art, z scoring can be used to normalize a distribution without changing a shape of the envelope of the distribution. The z scores are essentially changed to units of standard deviation. Each z score normalized unit reflects the amount of power in the signal, relative to the average of the signal. The scores are converted into mean deviation form, by subtracting the mean from each score. The scores are then normalized relative to standard deviation. All of the z scored normalized units have standard deviations that are equal to unity.

While the above describes normalization using Z scores, it should be understood that other normalizations can also be carried out, including T scoring, and others.

The above embodiments describe normalizing the power at every frequency within a specified range. The range may be from 0 to 100 hz, or to 128 hz, or to 500 hz. The range of frequencies is only restricted by the sampling rate. With an exemplary sampling rate of 30 KHz, an analysis up to 15 KHz can be done.

According to the present embodiment, an additional normalization is carried out which normalizes the power across time for each frequency. This results in information which has been normalized across frequencies and across time being used to create a doubly normalized spectrogram.

This embodiment can obtain additional information from brainwave data, and the embodiment describes automatically detecting different periods of sleep from the analyzed data. The periods of sleep that can be detected can include, but are not limited to, short wave sleep (SWS), rapid eye movement sleep (REM), intermediate sleep (IIS) and wakefulness. According to an important feature, a single channel of brainwave activity (that is obtained from a single location on the human skull) is used for the analysis.

Figure 41:
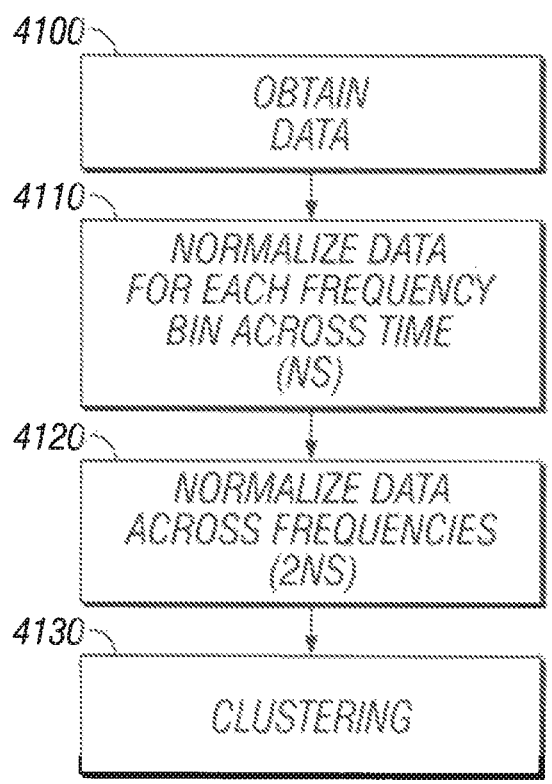
FIG. 41 illustrates a flowchart of operation of another embodiment which uses a double normalization.

The operation is carried out according to the flowchart of FIG. 41, which may be executed in any of the computer devices described herein, or may be executed across a network or in any other known way. At 4100, data is obtained. As described above, the obtained data can be one channel of EEG information from a human or other subject. The EEG data as obtained can be collected, for example, using a 256 Hz sampling rate, or can be sampled at a higher rate. The data is divided into epochs, for example 30 second epochs, and characterized according to frequency.

At 4110, a first frequency normalization is carried out. The power information is normalized using a z scoring technique on each frequency bin. In the embodiment, the bins may extend from one to 100 Hz and 30 bins per hertz. The normalization occurs across time. This creates a normalized spectrogram or NS, in which each frequency band from the signal has substantially the same weight. In the embodiment, each 30 second epoch is represented by a "preferred frequency" which is the frequency with the largest z score within that epoch.

Figure 42A:
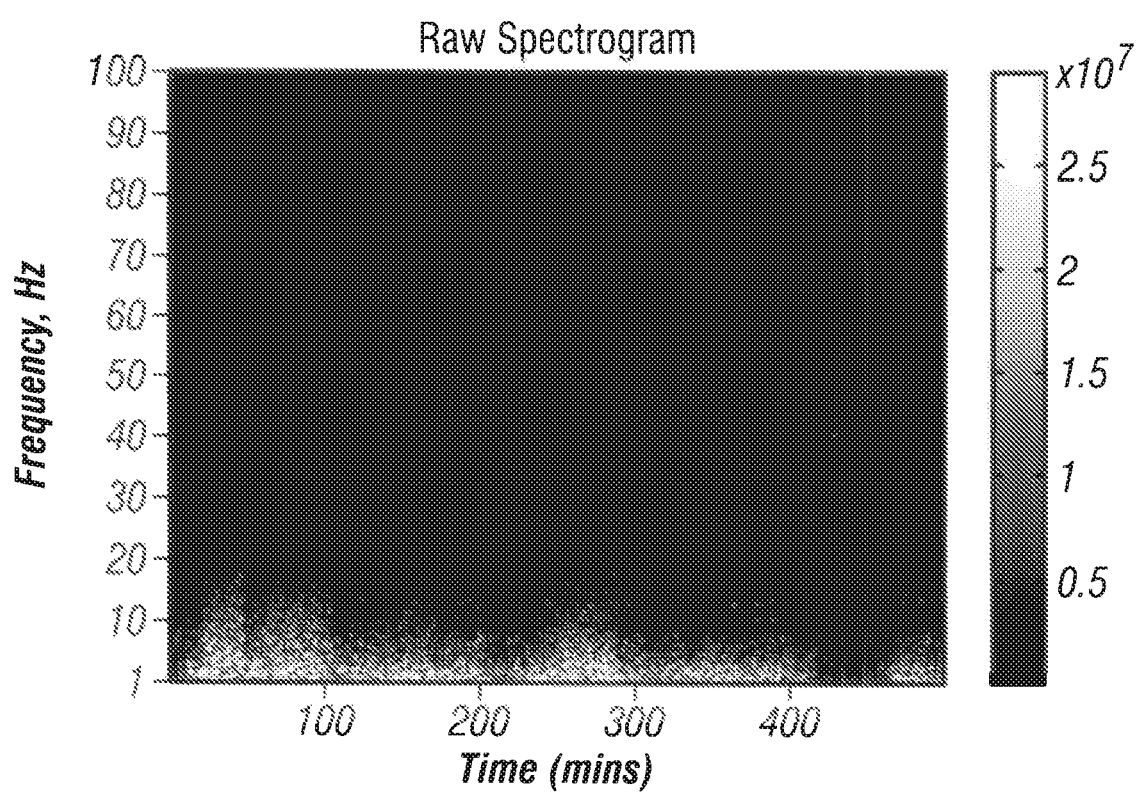
FIGS. 42a-42c show the raw spectrogram, single normalized spectrogram, and double normalized spectrogram respectively.
Figure 42B:
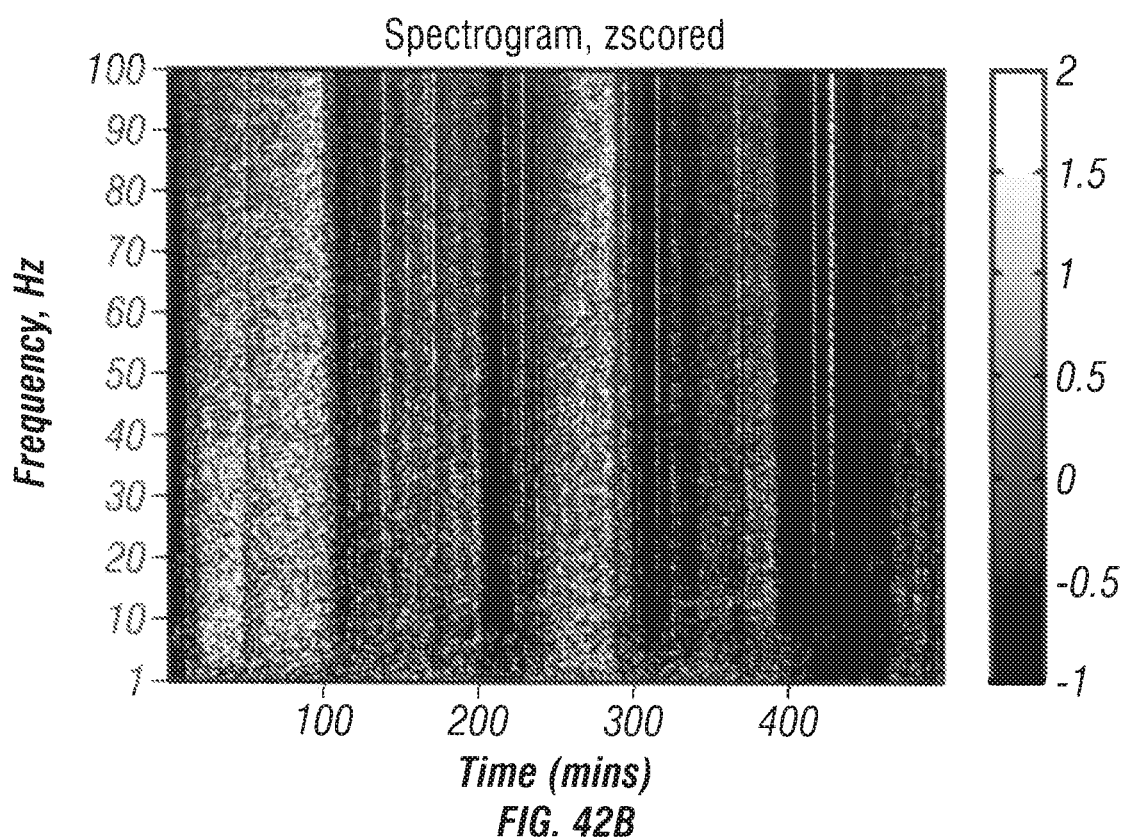
Figure 43:
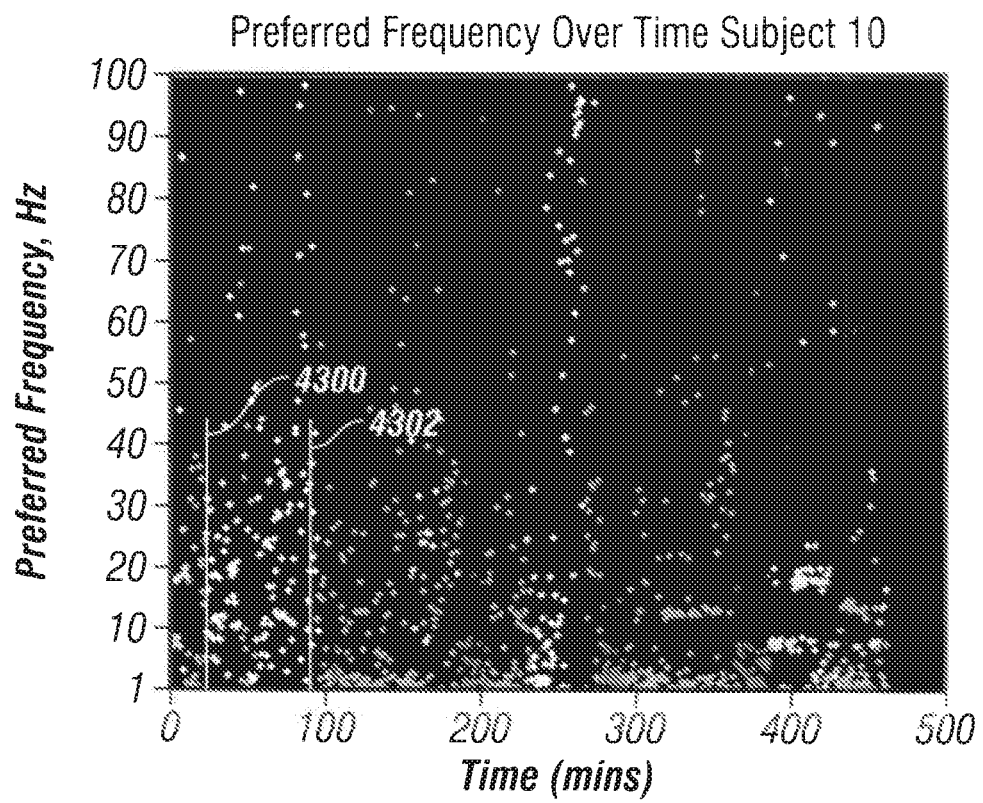
FIG. 43 shows the preferred frequency over time.
Figure 44:
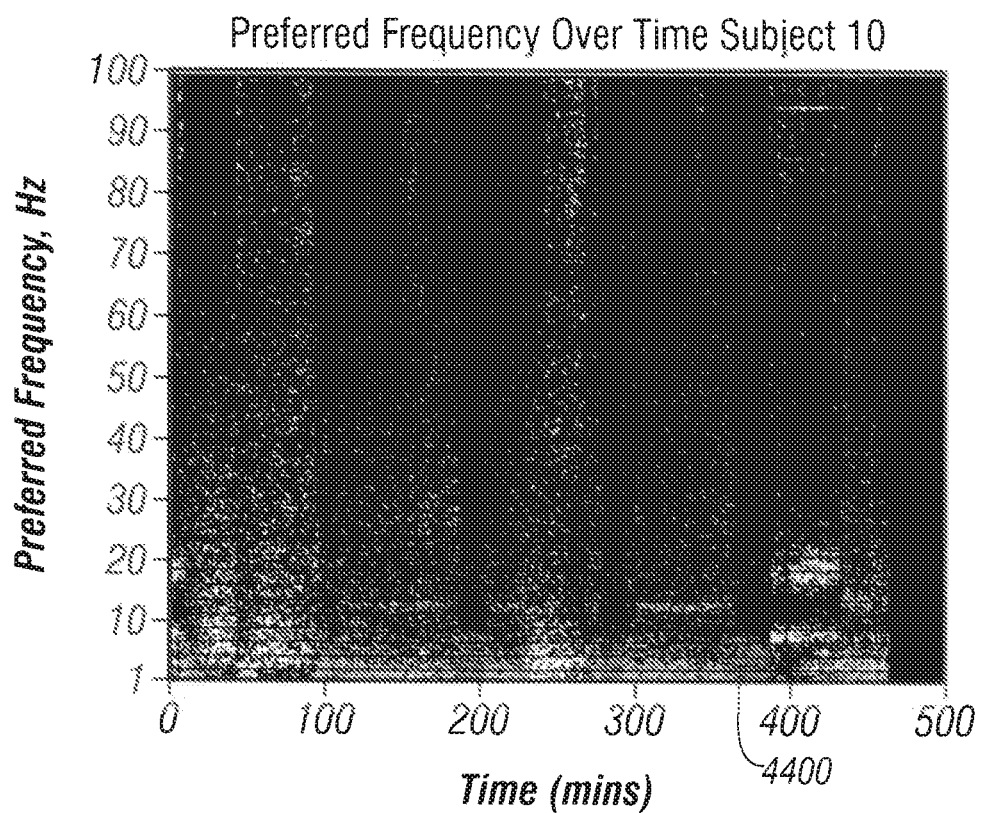
FIG. 44 shows a diagram of these frequencies.

This creates a special frequency space called the preferred frequency space. FIG. 42A illustrates the raw spectrogram, and FIG. 42B illustrates the normalized spectrum. Each epoch, e.g., a 30 second segment in FIG. 43, or a 1 second sliding window epoch in FIG. 44, is represented by the frequency with the largest z score. FIG. 44 illustrates how this broadly separates into different patterns.

Analysis of how those patterns are formed and allow analysis of the characteristics of the patterns. For example, the W or wakefulness state has been found by analysis to be characterized by a band in the alpha band, or 7 to 12 Hz and sometimes by a band in the beta (15 to 25 Hz).

Intermediate states display Delta values in the 1 to 4 Hz range, and the spindle frequencies in 12 to 15 Hz. These also show activity of the higher frequencies and the gamma range 3-90 Hz. Surprisingly, REM state defines compact bands at Delta and Theta frequencies, and short wave sleep was dominated by diffuse broad-spectrum activity.

Different sleep states, therefore, can be defined according to a discrimination function, where the discrimination function looks for certain activity in certain areas, and non-activity in other areas. The function may evaluate sleep states according to which of the frequency at areas have activity and which do not have activity.

More generally, however, any form of dynamic spectral scoring can be carried out on the compensated data. The discrimination function may require specific values, or may simply require a certain amount of activity to be present or not present, in each of a plurality of frequency ranges. The discrimination function may simply match envelopes of frequency response. The discrimination function may also look at spectral fragmentation and temporal fragmentation.

Figure 42C:
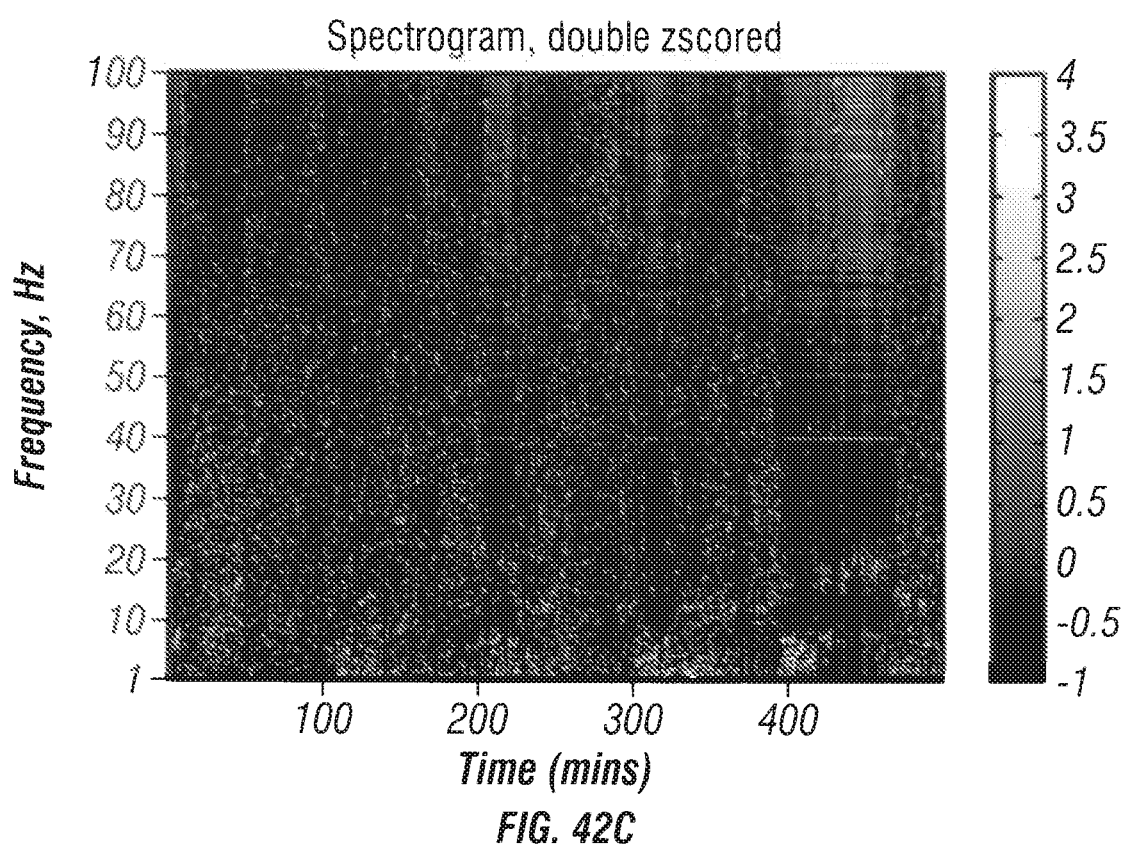

4120 illustrates a second normalization which is carried out across frequencies. The second normalization at 4120 produces a doubly normalized spectrogram. This produces a new frequency space, in which the bands become even more apparent. The second normalization is shown as FIG. 42C, where bands show as lighter values, representing the positive values, while darker regions will tend to have negative values.

The doubly normalized spectrogram values can be used to form filters that maximally separate the values within the space. FIG. 43 illustrates a graph of preferred frequency as a function of time, showing the different clusters of frequencies.

4130 illustrates a clustering technique which is carried out on the doubly normalized frequency. For example, the clustering technique may be a K means technique as described in the previous embodiments. The clusters form groups, as shown in FIG. 43. FIG. 44 illustrates how the areas between different states, such as boundary 4400, form multiple different clusters. Each cluster can represent a sleep state.

Figure 45:
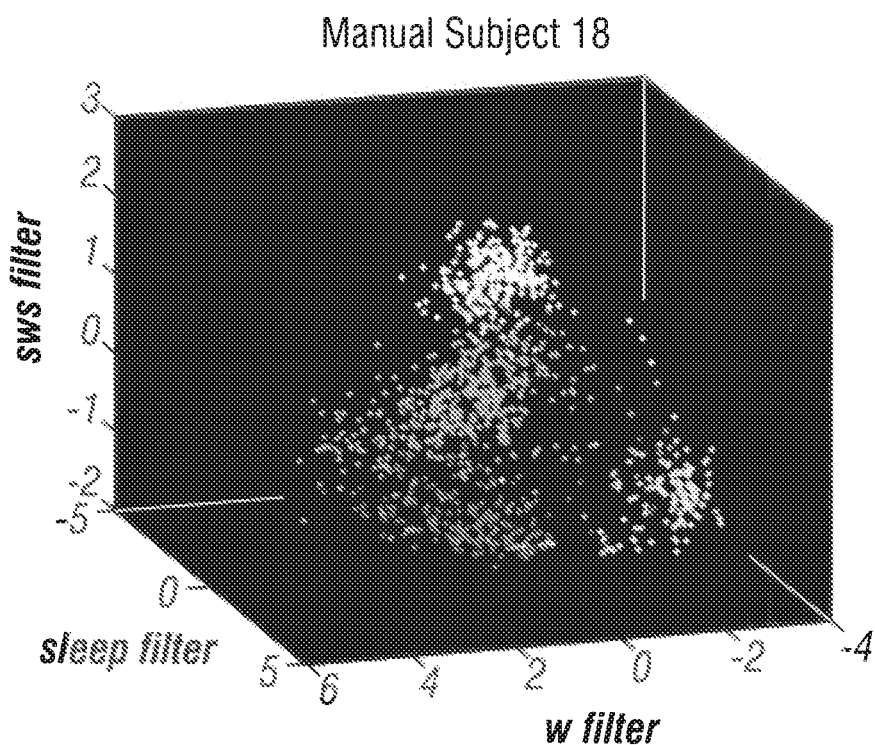
FIG. 45 shows a three-dimensional view of the data.

The clusters are actually multi-dimensional clusters, which can themselves be graphed to find additional information, as shown in FIG. 45. The number of dimensions can depend on the number of clustering variables. This illustrates how the doubly normalized spectrogram also allows many more measurement characteristics. FIG. 45 is actually a three-dimensional graph of different characteristics and can allow detection of the different states. The analysis, however, reveals that slow wave sleep is more unstable and time and frequency than rapid eye movement sleep or wakefulness. Intermediate sleep often forms a bridge to and from the short wave sleep.

Figure 46:
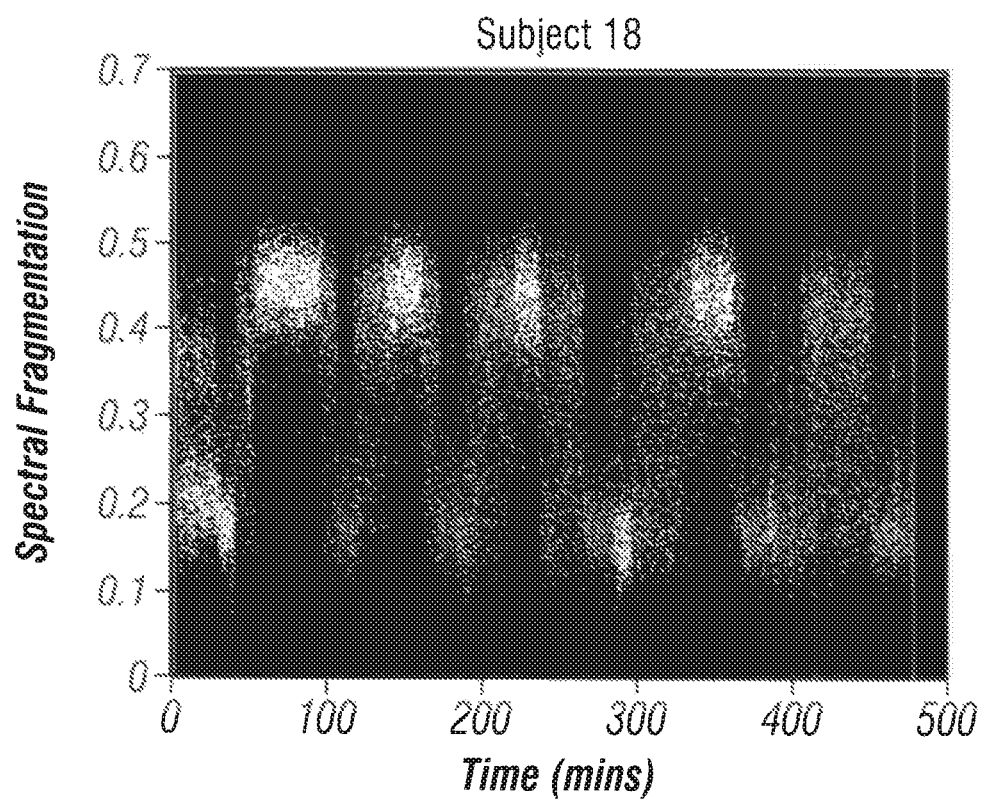
FIG. 46 shows a graph of spectral fragmentation for the frequencies.

Measurement of the average spread in normalized power across frequency which illustrates the spectral fragmentation is also possible, as shown in FIG. 46 illustrates the spectral fragmentation. Fragmentation values can alternatively be based on temporal fragmentation for the different states may also be used as part of the discrimination function. For example:

Using Z and ZZ to correspond to the NS and 2 NS values respectively:

$$W\_filter=mean(ZZ(12\text{-}15Hz))+mean(ZZ(1\text{-}4Hz))+mean(ZZ(4\text{-}7Hz));$$

$$N\ rem\_filter=mean(ZZ(60\text{-}100Hz))+mean(ZZ(4\text{-}7Hz))-[mean(ZZ(12\text{-}15Hz))+mean(ZZ(25\text{-}60Hz))+mean(ZZ(15\text{-}25Hz))];$$

$$sws\_filter=mean(Z(4\text{-}7Hz))+mean(Z(7\text{-}12Hz)).$$

The fragmentation values are as follows:

$$Spectral\_frag=mean(abs(grad\_f(ZZ(1\text{-}100Hz))));$$

$$Spectral\_temp=mean(abs(grad\_t(ZZ(1\text{-}100Hz))));$$

Where $grad\_f$ and $grad\_t$ correspond to the two-dimensional nearest neighbor gradients of ZZ.

These two functions are evaluated on the doubly normalized spectrum, relying on homogeneous increases in gain at all frequencies as caused movement artifacts in NREM sleep and W would lead to abnormally elevated fragmentation values in the singly normalized spectrum.

These fragmentation values may be used as part of the discrimination function. Importantly, and as described above, this discrimination function is typically not apparent from any previous analysis technique, including manual techniques.

The computation may be characterized by segmenting, or may use overlapping windows or a sliding window, to increase the temporal registration. This enables many techniques that have never been possible before. By characterizing on-the-fly, this enables distinguishing using the dynamic spectral scoring, between sleep states and awake states using the brainwave signature alone.

Another aspect includes a machine which automatically obtains EEG information, and includes a computer that analyzes the EEG information to determine information about the sleep state. For example, the information may include the actual sleep state, or other parts of the sleep state. The computer may also include nonvolatile memory therein to store the information indicative of the sleep state, and may include, for example, a wireless network connection to allow sending the information indicative of the sleep state to a remote device. The user can wear the machine, or an electrode that is connected to the machine, in order to characterize his or her sleep.

The above has described how information can be used to determine sleep states. These techniques may also be used for other applications including characterizing sleep states, and other techniques. Applications may include determination of whether a patient has taken certain kinds of drugs based on their sleep state, and based on variables that were previously determined as changing in brain function based on those sleep states. Another application can analyze brain wave signals to determine alcohol consumption, e.g., forming a system that can be used as a "breathalyzer".

The general structure and techniques, and more specific embodiments which can be used to effect different ways of carrying out the more general goals are described herein.

Although only a few embodiments have been disclosed in detail above, other embodiments are possible and the inventors intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art. For example, other applications are possible and other forms of discrimination functions and characterization is possible. While the above extensively described characterizing the frequency in terms of its "preferred frequency", it should be understood that more rigorous characterization of the information may be possible. Also, while the above only refers to determining sleep states from the EEG data, and refers to only a few different kinds of determination of sleep states, it should be understood that other applications are contemplated.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

The computers described herein may be any kind of computer, either general purpose, or some specific purpose computer such as a workstation. The computer may be a Pentium class computer, running Windows XP or Linux, or may be a Macintosh computer. The computer may also be a handheld computer, such as a PDA, cell phone, or laptop.

The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

What is claimed is:

1. An apparatus comprising:
an electrode and a computing device, the electrode being in operable connection to the computing device, the computing device having one or more data processors and a non-transitory computer readable storage medium containing instructions which, when executed on the one or more data processors, cause the one or more data processors to perform actions including:
accessing, from the electrode, signal data indicative of brain activity of a subject over a particular time period;
generating, based on the signal data, spectrogram data comprising a power estimated for each frequency band of a set of frequency bands;
generating normalized spectrogram data by processing the spectrogram data using a first normalization function, wherein the first normalization function is configured to:
for each frequency band of the set of frequency bands:
generate a first normalization parameter based on powers in the spectrogram for the frequency band across a set of time bins in the particular time period; and
normalize the powers of the frequency band in the spectrogram using the first normalization parameter;
generating a doubly normalized spectrogram data by processing the normalized spectrogram data using a second normalization function, wherein the second normalization function is configured to:
for each time bin of the set of time bins:
generate a second normalization parameter based on powers in the normalized spectrogram for the time bin across the set of frequency bands; and
normalize the powers of the time bin in the normalized spectrogram using the second normalization parameter;
generating at least one parameter indicative of sleep stage based on the doubly normalized spectrogram data; and
determining that the at least one parameter is consistent with a classification of pathological condition of the subject, wherein the determination is based on comparing
the at least one parameter to one or more reference parameters indicative of sleep stages associated with other subjects with known classifications of the pathological condition, wherein the pathological condition includes one of epilepsy, Alzheimer's disease, depression, brain trauma, insomnia, restless leg syndrome, or sleep apnea.

2. The apparatus of claim 1, wherein the actions further include applying a discrimination function to the at least one parameter to generate the sleep stage.

3. The apparatus of claim 1, wherein the at least one parameter further indicates a level of attentiveness or a level of alertness of the subject.

4. The apparatus of claim 1, wherein the actions further include predicting, based on the at least one parameter, medication and chemical effects attributed to a drug consumption of the subject.

5. The apparatus of claim 1, wherein the signal data corresponds to signals obtained from a single channel of the electrode.

6. A method comprising:
accessing, from an electrode being in operable connection to a computing device, signal data indicative of brain activity of a subject over a particular time period;
generating, based on the signal data and by one or more data processors, spectrogram data comprising a power estimated for each frequency band of a set of frequency bands;
generating, by the one or more data processors, normalized spectrogram data by processing the spectrogram data using a first normalization function, wherein the first normalization function is configured to:
for each frequency band of the set of frequency bands:
generate a first normalization parameter based on powers in the spectrogram for the frequency band across a set of time bins in the particular time period; and normalize the powers of the frequency band in the spectrogram using the first normalization parameter;

generating, by the one or more data processors, a doubly normalized spectrogram data by processing the normalized spectrogram data using a second normalization function, wherein the second normalization function is configured to:

for each time bin of the set of time bins:

generate a second normalization parameter based on powers in the normalized spectrogram for the time bin across the set of frequency bands; and normalize the powers of the time bin in the normalized spectrogram using the second normalization parameter;

generating, by the one or more data processors, at least one parameter indicative of sleep stage based on the doubly normalized spectrogram data; and determining, by the one or more data processors, a classification of pathological condition of the subject by comparing the at least one parameter to one or more reference parameters indicative of sleep stages associated with other subjects with known classifications of the pathological condition, wherein the pathological condition includes one of epilepsy, Alzheimer's disease, depression, brain trauma, insomnia, restless leg syndrome, or sleep apnea.

7. The method of claim 6, further comprising applying a discrimination function to the at least one parameter to generate the sleep stage.

8. The method of claim 6, wherein the at least one parameter further indicates a level of attentiveness or a level of alertness of the subject.

9. The method of claim 6, further comprising predicting, based on the at least one parameter, medication and chemical effects attributed to a drug consumption of the subject.

10. The method of claim 6, wherein the signal data corresponds to signals obtained from a single channel of the electrode.

11. A computer-program product tangibly embodied in a non-transitory machine-readable storage medium, including instructions configured to cause one or more data processors to perform operations comprising:

accessing, from an electrode being in operable connection to a computing device, signal data indicative of brain activity of a subject over a particular time period;

generating, based on the signal data, spectrogram data comprising a power estimated for each frequency band of a set of frequency bands;

generating normalized spectrogram data by processing the spectrogram data using a first normalization function, wherein the first normalization function is configured to:

for each frequency band of the set of frequency bands:

generate a first normalization parameter based on powers in the spectrogram for the frequency band across a set of time bins in the particular time period; and normalize the powers of the frequency band in the spectrogram using the first normalization parameter;

generating a doubly normalized spectrogram data by processing the normalized spectrogram data using a second normalization function, wherein the second normalization function is configured to:

for each time bin of the set of time bins:

generate a second normalization parameter based on powers in the normalized spectrogram for the time bin across the set of frequency bands; and normalize the powers of the time bin in the normalized spectrogram using the second normalization parameter;

generating at least one parameter indicative of sleep stage based on the doubly normalized spectrogram data; and determining that the at least one parameter is consistent with a classification of pathological condition of the subject, wherein the determination is based on comparing the at least one parameter to one or more reference parameters indicative of sleep stages associated with other subjects with known classifications of the pathological condition, wherein the pathological condition includes one of epilepsy, Alzheimer's disease, depression, brain trauma, insomnia, restless leg syndrome, or sleep apnea.

12. The computer-program product of claim 11, wherein the operations further include applying a discrimination function to the at least one parameter to generate the sleep stage.

13. The computer-program product of claim 11, wherein the at least one parameter further indicates a level of attentiveness or a level of alertness of the subject.

14. The computer-program product of claim 11, wherein the operations further include predicting, based on the at least one parameter, medication and chemical effects attributed to a drug consumption of the subject.

15. The computer-program product of claim 11, wherein the signal data corresponds to signals obtained from a single channel of the electrode.

* * * * *